US012637480B2

(12) United States Patent
Li et al.

(10) Patent No.: US 12,637,480 B2
(45) Date of Patent: May 26, 2026

(54) HETEROCYCLIC COMPOUNDS AS STING MODULATORS

(71) Applicant: BEIGENE, LTD., Camana Bay (KY)

(72) Inventors: Jing Li, Beijing (CN); Sanjia Xu, Beijing (CN); Zhiwei Wang, Beijing (CN); Guoliang Zhang, Beijing (CN); Ce Wang, Beijing (CN); Jianzhuang Miao, Beijing (CN); Lina Gu, Beijing (CN); Gang Chen, Beijing (CN); Xiaosong Yu, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 599 days.

(21) Appl. No.: 17/925,854

(22) PCT Filed: May 27, 2021

(86) PCT No.: PCT/CN2021/096510
§ 371 (c)(1),
(2) Date: Nov. 17, 2022

(87) PCT Pub. No.: WO2021/239068
PCT Pub. Date: Dec. 2, 2021

(65) Prior Publication Data

US 2023/0212192 A1 Jul. 6, 2023

(30) Foreign Application Priority Data

May 28, 2020 (WO) ................ PCT/CN2020/092949

(51) Int. Cl.
*C07D 519/00* (2006.01)

(52) U.S. Cl.
CPC .................................. *C07D 519/00* (2013.01)

(58) Field of Classification Search
CPC .................................................... C07D 519/00
See application file for complete search history.

(56) References Cited

U.S. PATENT DOCUMENTS

| | | | |
|---|---|---|---|
| 2015/0343056 | A1 | 12/2015 | Chen |
| 2017/0296655 | A1 | 10/2017 | Chen |
| 2018/0064745 | A1 | 3/2018 | Katibah |
| 2019/0263851 | A1 | 8/2019 | Chen |
| 2020/0102342 | A1 | 4/2020 | Chen |
| 2020/0140477 | A1 | 5/2020 | Chen |
| 2020/0179431 | A1 | 6/2020 | Katibah |
| 2020/0308216 | A1 | 10/2020 | Chen |
| 2022/0251135 | A1 | 8/2022 | Li |
| 2022/0289768 | A1 | 9/2022 | Li |

FOREIGN PATENT DOCUMENTS

| | | | |
|---|---|---|---|
| CN | 105120902 | A | 12/2015 |
| CN | 107530415 | A | 1/2018 |
| CN | 110742893 | | 2/2020 |
| CN | 112778336 | | 5/2021 |
| EP | 3505527 | | 7/2019 |
| WO | 2014099824 | A1 | 6/2014 |
| WO | 2014189805 | A1 | 11/2014 |
| WO | 2015077354 | A1 | 5/2015 |
| WO | 2016096174 | A1 | 6/2016 |
| WO | 2016145102 | A1 | 9/2016 |
| WO | 2017175147 | A1 | 10/2017 |
| WO | 2017175156 | A1 | 10/2017 |
| WO | 2019023459 | A1 | 1/2019 |
| WO | 2019046498 | A1 | 3/2019 |
| WO | 2019046500 | A1 | 3/2019 |
| WO | 2019074887 | A1 | 4/2019 |
| WO | 2019079261 | A1 | 4/2019 |
| WO | 2019227007 | A1 | 11/2019 |
| WO | 2020020097 | A1 | 1/2020 |
| WO | 2020028565 | A1 | 2/2020 |
| WO | 2020146237 | A1 | 7/2020 |
| WO | 2021013234 | A1 | 1/2021 |
| WO | 2021068866 | A1 | 4/2021 |
| WO | 2021083383 | | 5/2021 |

OTHER PUBLICATIONS

H.-K. Han. AAPS Pharmsci. (2000) 2(1), article 6, pp. 1-11 (Year: 2000).*

P. Ettmayer et al. J. Med. Chem. (2004) 47(10), pp. 2393-2404 (Year: 2004).*

B. Testa. Biochem. Pharm. (2004) 68, pp. 2097-2106 (Year: 2004).*

Crow, Y. J. et al., "Mutations in the gene encoding the 3'-5' DNA exonuclease TREX1 cause Aicardi-Goutières syndrome at the AGS1 locus," Nat. Genet., 38(8):917-920, 2006.

Diner, E. J. et al., "The Innate Immune DNA Sensor cGAS Produces a Noncanonical Cyclic Dinucleotide that Activates Human STING," Cell Reports, 3(5): 1355-1361, 2013.

Liu, J., International Search Report and Written Opinion issued in International Patent Application No. PCT/CN2020/103987, mailed Oct. 27, 2020.

Lochmuller, C. H. et al., "Chromatographic resolution of enantiomers," Journal of Chromatography, 113:283-302, 1975.

Stetson, D. B. et al., "Trexl prevents cell-intrinsic initiation of autoimmunity," Cell, vol. 134, No. 4, Aug. 2008, pp. 587-598.

Wang, D., International Search Report and Written Opinion issued in International Patent Application No. PCT/CN2021/096510, dated Aug. 26, 2021.

Wu, T., International Search Report and Written Opinion issued in International Patent Application No. PCT/CN2020/119871, mailed Jan. 11, 2021.

Zhang, X. et al., "Cyclic GMP-AMP Containing Mixed Phosphodiester Linkages Is An Endogenous High-Affinity Ligand for STING," Molecular Cell, 51(2):226-235, 2013.

* cited by examiner (Continued)

*Primary Examiner* — Andrew D Kosar
(74) *Attorney, Agent, or Firm* — McNeill PLLC

(57) ABSTRACT

Disclosed herein are heterocyclic compounds that may be used as STING modulators, the process for synthesis and to the use of such compounds in treatment of various diseases including cancers.

15 Claims, No Drawings

HETEROCYCLIC COMPOUNDS AS STING MODULATORS

CROSS-REFERENCE TO RELATED APPLICATIONS

This application is a U.S. National Stage Application under 35 U.S.C. § 371 of International Application No. PCT/CN2021/096510, filed May 27, 2021, which claims priority to Patent Application No. PCT/CN2020/092949 (CN), filed May 28, 2020.

FIELD OF THE INVENTION

The present disclosure relates to heterocyclic compounds and derivatives thereof useful as STING modulators. The present disclosure also relates to the process for synthesis and to the use of such compounds in the treatment of various diseases including cancers.

BACKGROUND OF THE INVENTION

The innate immune system is specialized to act quickly against different danger signals. It provides the first line of defense against bacteria, viruses, parasites and other infectious threats by the production of soluble bioactive molecules such as cytokines or chemokines. By responding to these damage-associated molecular patterns (DAMPs) or pathogen-associated molecular patterns (PAMPs) described above, the innate immune system is able to provide protection against a wide range of threats to the host.

It has recently been demonstrated that the main sensor for cytosolic DNA is the cyclic GMP-AMP synthase (cGAS). cGAS catalyzes the generation of the cyclic-dinucleotide 2'-3'-cGAMP, an atypical second messenger that strongly binds to the ER-transmembrane adaptor protein STING (STimulator of INterferon Genes). cGAMP-bound STING goes through a conformational change, translocates to a perinuclear compartment and induces the activation of critical transcription factors IRF-3 and NF-kB. This leads to a strong induction of type I interferons and production of pro-inflammatory cytokines such as IL-6, TNF-alpha and IFN-gamma.

The type I interferons and pro-inflammatory cytokines can strongly potentiate T cell activation by enhancing the ability of dendritic cells and macrophages to uptake, process, present and cross-present antigens to T cells. Compounds that can induce type I interferon production are used in vaccines, where they act as adjuvants, enhancing specific immune responses to antigens. Compounds that can induce interferon production have potential use in the treatment of human cancers.

In contrast, excessive type I interferon production is found among patients with various forms of autoimmune disease. Genetic evidence in humans and support from studies in animal models substantiates the hypothesis, that inhibition of STING results in reduced amount of type I interferon that is responsible for autoimmune diseases (Cow Y J, et al., *Nat, Genet.* 2006, 38, 917-920; Stetson D B, et al., *Cell* 2008, 134, 587-598). Therefore, inhibitors of STING provide a treatment to patients with chronic type I interferon and proinflammatory cytokine production associated with infections or complex autoimmune diseases. Compounds that bind to STING may act as antagonists and could be useful in the treatment, for example of autoimmune diseases.

It is envisaged that targeting STING with activation or inhibiting agents may be a promising approach for treating diseases and conditions in which modulation for the type I IFN pathway is beneficial, including inflammatory, allergic and autoimmune diseases, infectious diseases, cancer, pre-cancerous syndromes and as immunogenic composition or vaccine adjuvants.

The compounds of this invention modulate the activity of STING, and accordingly, may provide a therapeutic impact in treatment of diseases, disorders and/or conditions in which modulation of STING is beneficial, for example for inflammation, allergic and autoimmune diseases, infectious diseases, cancer, pre-cancerous syndromes and as vaccine adjuvants.

SUMMARY OF THE INVENTION

One objective of the present invention is to provide compounds and derivatives thereof useful as STING modulators.

Aspect 1: A compound of formula (I), (I)

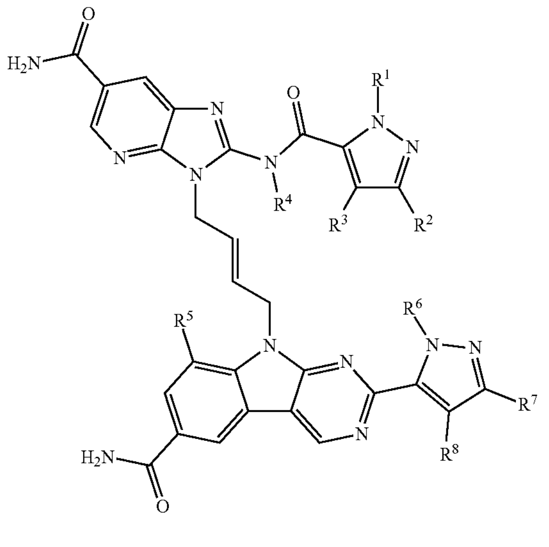

or a pharmaceutically acceptable salt, stereoisomer, tautomer or prodrug thereof, wherein:

$R^1$, $R^2$, $R^3$, $R^4$, $R^6$, $R^7$ and $R^8$ which may be the same or different, each are independently selected from hydrogen, halogen, $-C_{1-8}$alkyl, $-C_{2-8}$alkenyl, $-C_{2-8}$alkynyl, cycloalkyl, heterocyclyl, aryl, heteroaryl, —CN, $-NO_2$, $-OR^a$, $-SO_2R^a$, $-C(=O)R^a$, $-C(=O)OR^a$, $-C(=O)NR^aR^b$, $-C(=NR^a)NR^bR^c$, $-NR^aR^b$, $-NR^aC(=O)R^b$, $-NR^aC(=O)NR^bR^c$, $-NR^aC(=O)OR^b$, $-NR^aSONR^bR^c$, $-NR^2SO_2NR^bR^c$, $-SO_2NR^aR^b$, or $NR^2SO_2R^b$, each of said $-C_{1-8}$alkyl, $-C_{2-8}$alkenyl, $-C_{2-8}$alkynyl, cycloalkyl, heterocyclyl, aryl, or heteroaryl is optionally substituted with $R^d$;

$R^5$ is selected from $-R^{5a}$, $-OR^{5a}$, $-SR^{5a}$ or $-NR^{5a}R^{5b}$;

$R^{5a}$ and $R^{5b}$ are independently selected from hydrogen, $-C_{1-8}$alkyl, $-C(=O)R$, $-(CH_2)_{n1}-NRR'$, $-(CH_2CH_2O)_{n1}-NRR'$, $-(OCH_2CH_2)_{n1}-NRR'$, $-(CH_2OCH_2)_{n1}-NRR'$ or

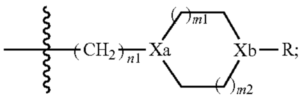

R and R' are each independently selected from hydrogen, $—C_{1-8}$alkyl, $—C(═O)OR^9$; $—C(═O)—CH_2—OR^9$, $—(CH_2)_2—OR^9$;

$R^9$ is selected from hydrogen, $—C_{1-8}$alkyl, (such as tert-butyl), or $—NR^{9a}R^{9b}$;

$R^{9a}$ and $R^{9b}$ are each independently selected from hydrogen, $—C_{1-8}$alkyl, $—C_{2-8}$alkenyl, $—C_{2-8}$alkynyl, cycloalkyl, heterocyclyl, aryl, and heteroaryl;

Xa and Xb are independently selected from N and CH;

n1 is 1, 2, 3, 4, 5, or 6;

m1 and m2 are each independently 0, 1, or 2;

$R^a$, $R^b$ and $R^c$ are each independently selected from the group consisting of hydrogen, $—C_{1-8}$alkyl, $—C(═O)OR^e$ or $—C(═O)R^e$, wherein the $—C_{1-8}$alkyl is optionally substituted with $NR^aR^b$, $—C_{3-8}$cycloalkyl or a 4-7 membered heterocycle comprising at least one heteroatom selected from N, O and S with the remaining ring atoms being carbon; and $R^d$ and $R^e$ are each independently selected from halogen, $—C_{1-8}$alkyl, —OH, $—NH_2$, —CN, $—C_{1-8}$alkoxy, and $—C_{3-8}$cycloalkyl, wherein each of the $—C_{1-8}$alkyl, $—C_{1-8}$alkoxy and $—C_{3-8}$cycloalkyl is optionally substituted with halogen, —OH, $—NH_2$, —CN, or an oxo group.

Aspect 2: The compound according to Aspect 1, $R^5$ is selected from

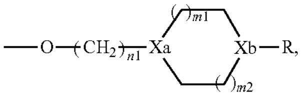

$—O—(CH_2)_{n1}—NRR'$, $—(OCH_2CH_2)_{n1}—NRR'$ or $—O—(CH_2OCH_2)_{n1}—NRR'$.

Aspect 3: The compound according to Aspect 2, wherein $R^1$, $R^2$, $R^3$, $R^1$, $R^7$ and $R^8$ are each independently selected from the group consisting of hydrogen or $—C_{1-8}$alkyl.

Aspect 4: The compound according to any one of Aspects 1-3, wherein $R^4$ is hydrogen.

Aspect 5: The compound according to Aspects 1-4, wherein $R^3$ and $R^8$ are hydrogen.

Aspect 6: The compound according to any one of Aspects 1-5, wherein $R^1$, $R^2$, $R^1$ and $R^7$ each independently selected from methyl or ethyl.

Aspect 7: The compound of any one according to Aspects 1-6, wherein $R^1$ and $R^6$ are each ethyl; and/or $R^2$ and $R^7$ are each methyl.

Aspect 8: The compound of any one according to Aspects 1-7, wherein $R^5$ is selected from

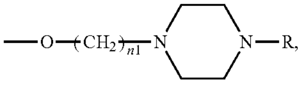

-continued

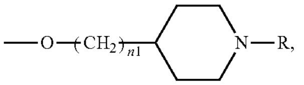

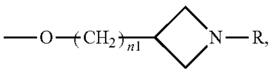

$—O—(CH_2)_{n1}—NHR$, or $—(OCH_2CH_2)_{n1}—NHR$; n1 is 2, 3 or 4; R is selected from hydrogen, $CH_3$, $—C(═O)OR^9$, or $—C(═O)—CH_2—OR^9$; $R^9$ is selected from hydrogen, $NH_2$, or $—C(CH_3)_3$.

Aspect 9: The compound of according to Aspect 8, wherein R is selected from hydrogen, —

$CH_3$,

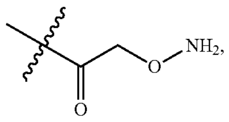

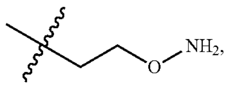

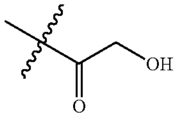

or $—C(═O)OC(CH_3)_3$.

Aspect 10: The compound of any one according to Aspects 1-9, wherein formula (I) is (II)

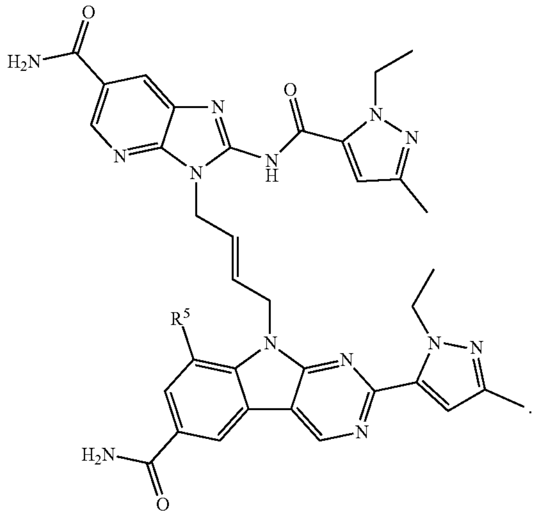

Aspect 11: The compound according to Aspect 10, wherein the formula (II) is

-continued
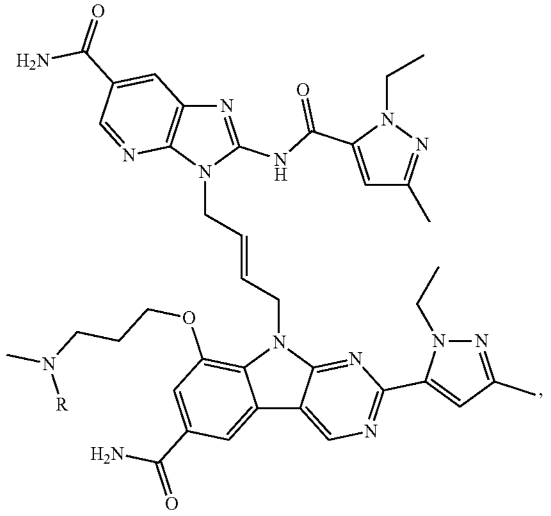
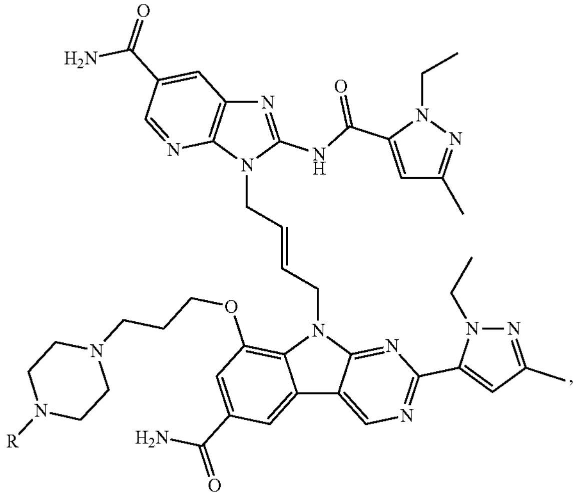
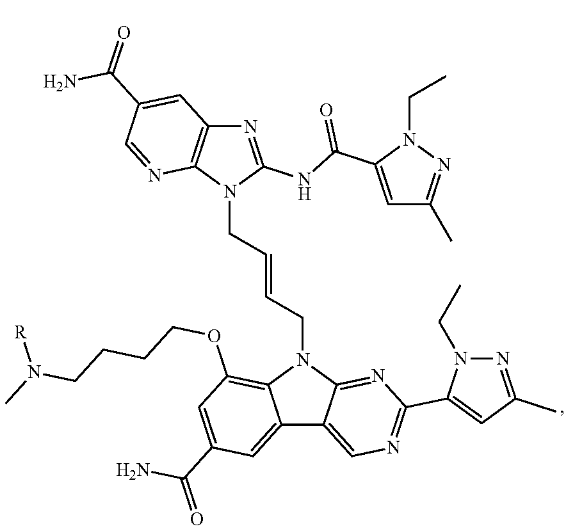
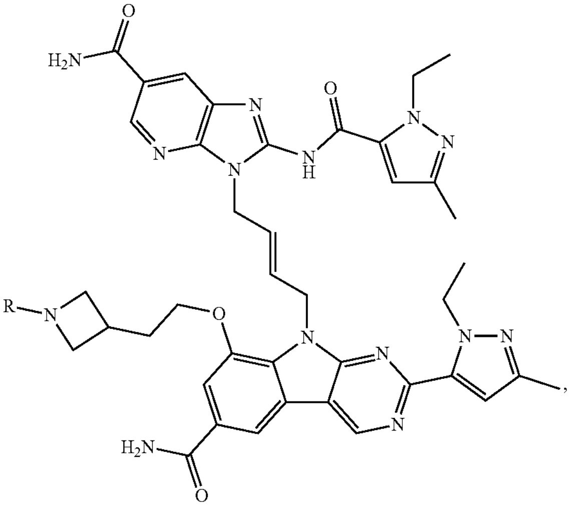
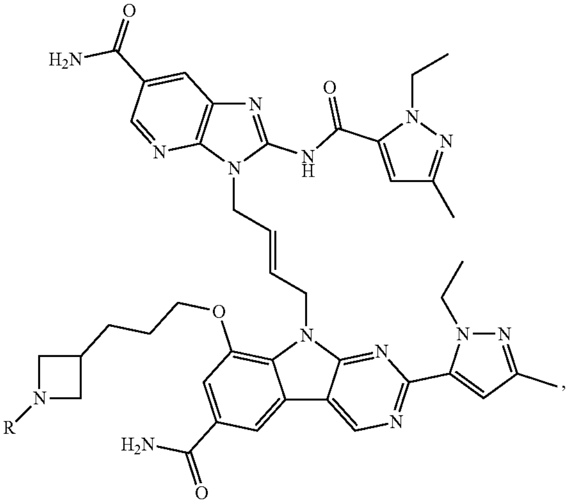
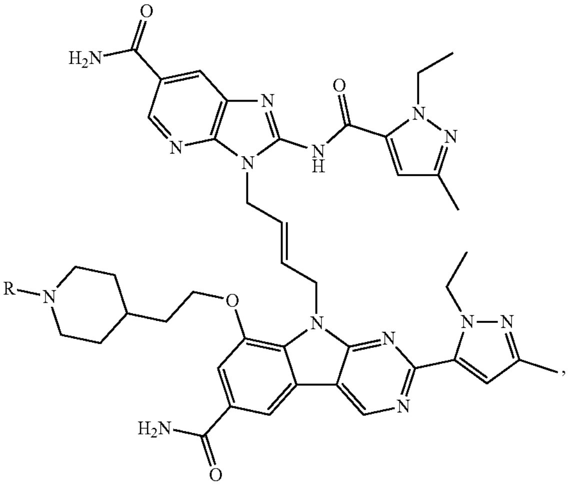

-continued
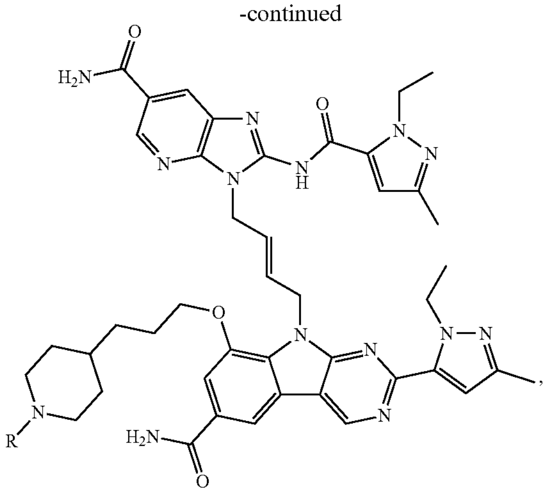
, or
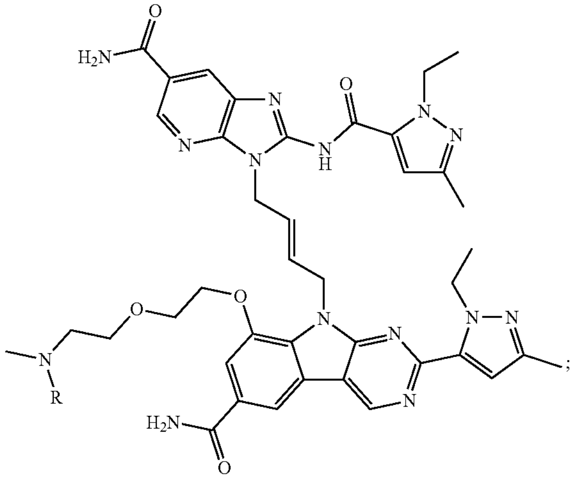
;
wherein R is selected from $CH_3$,
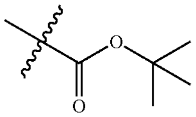
,
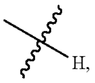
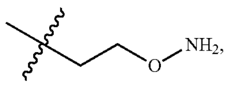
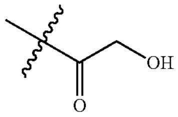
or
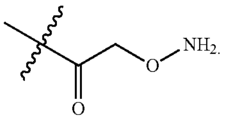
Aspect 12: The compound according to Aspect 1, wherein the compound is
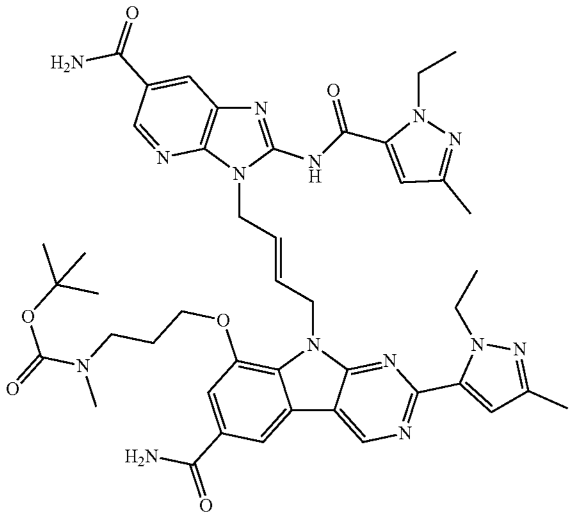 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN(C)C(=O)OC(C)(C)C)c21]

-continued
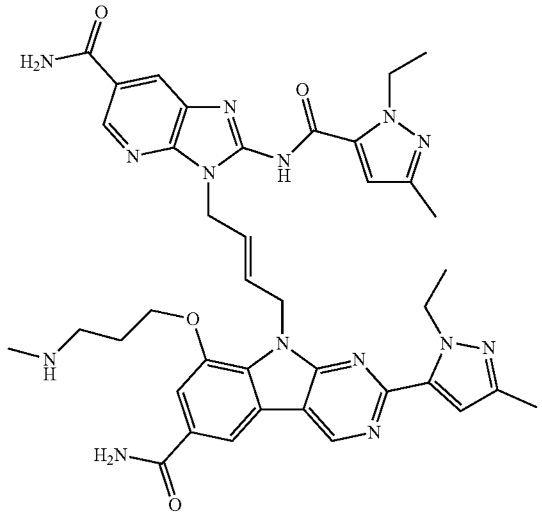
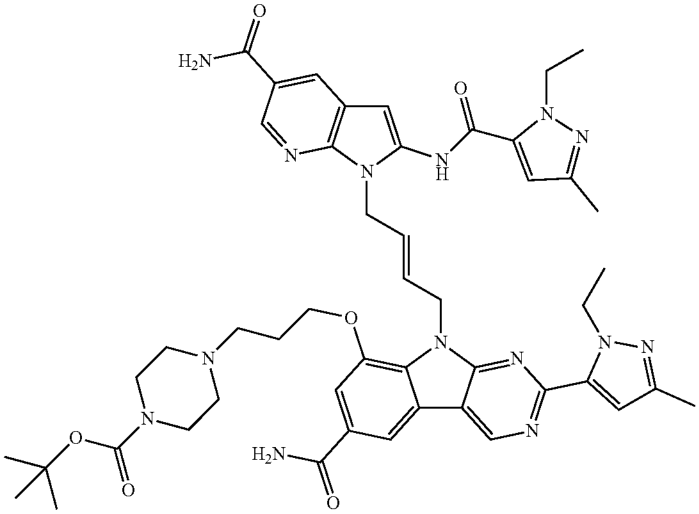 [SMILES: CCn1nc(C)cc1C(=O)Nc1cc2cc(C(N)=O)cnc2n1C/C=C/Cn1c2nc(-c3cc(C)nn3CC)ncc2c2cc(C(N)=O)cc(OCCCN3CCN(C(=O)OC(C)(C)C)CC3)c21]
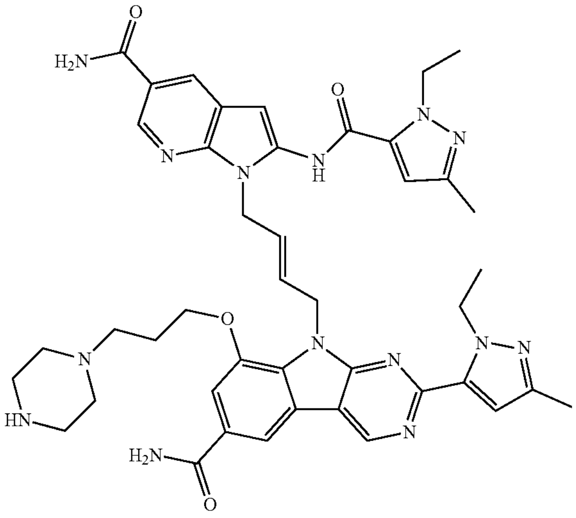 [SMILES: CCn1nc(C)cc1C(=O)Nc1cc2cc(C(N)=O)cnc2n1C/C=C/Cn1c2nc(-c3cc(C)nn3CC)ncc2c2cc(C(N)=O)cc(OCCCN3CCNCC3)c21]

-continued
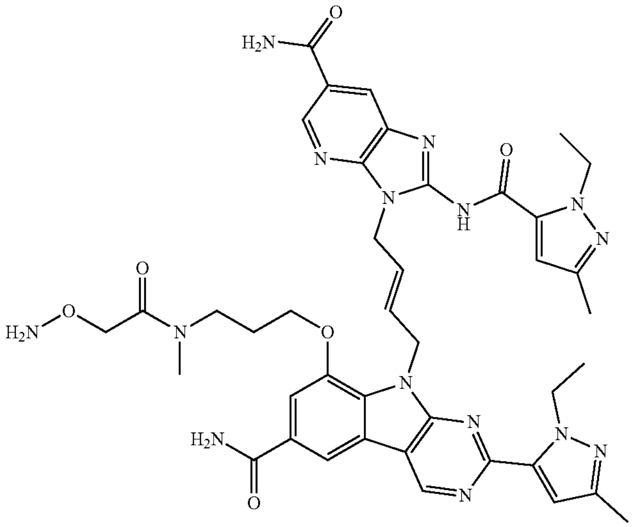 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN(C)C(=O)CON)c21]
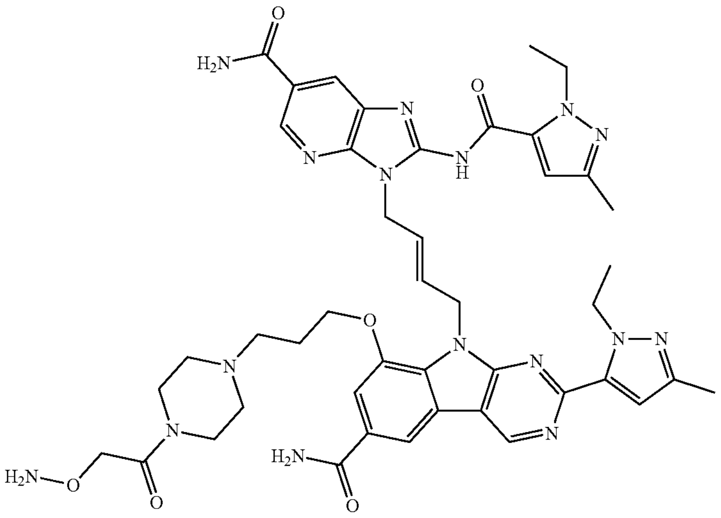 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN3CCN(C(=O)CON)CC3)c21]
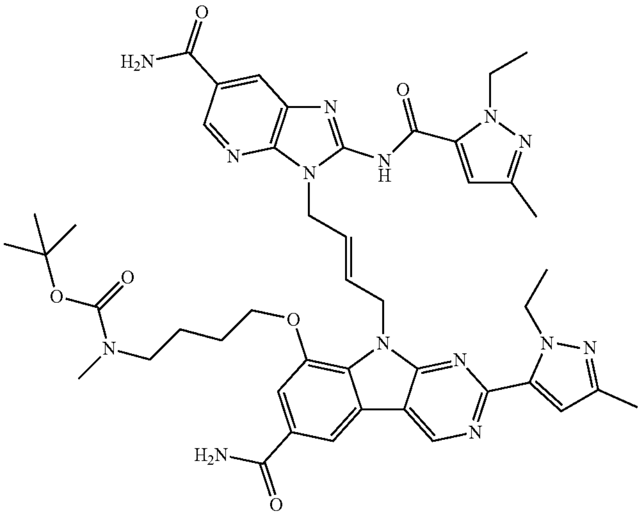 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCCN(C)C(=O)OC(C)(C)C)c21]

-continued
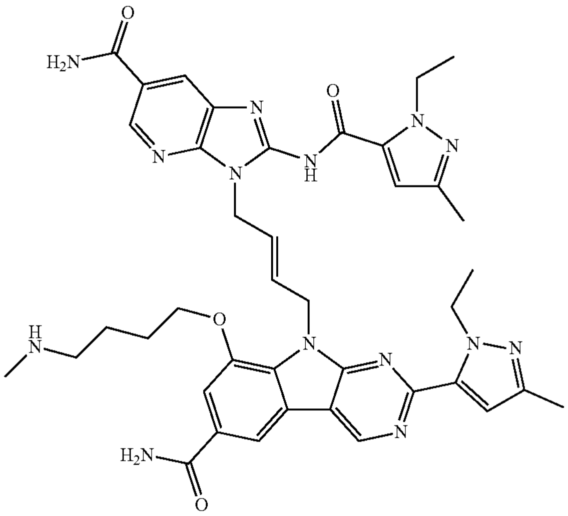
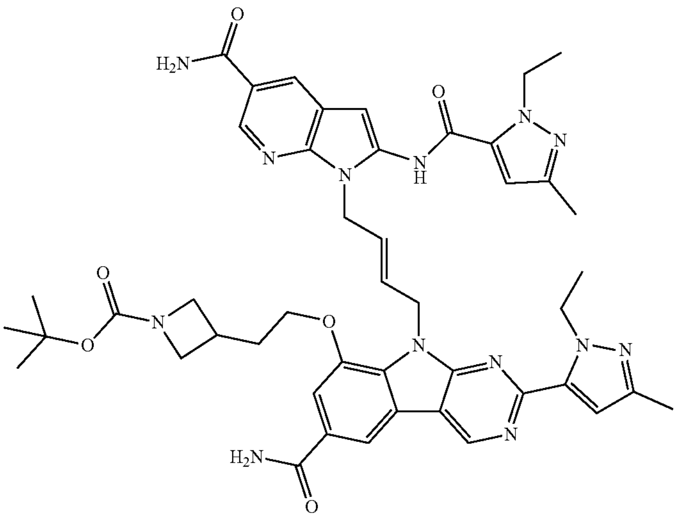 [SMILES: CCn1nc(C)cc1C(=O)Nc1cc2cc(C(N)=O)cnc2n1C/C=C/Cn1c2nc(-c3cc(C)nn3CC)ncc2c2cc(C(N)=O)cc(OCCC3CN(C(=O)OC(C)(C)C)C3)c21]
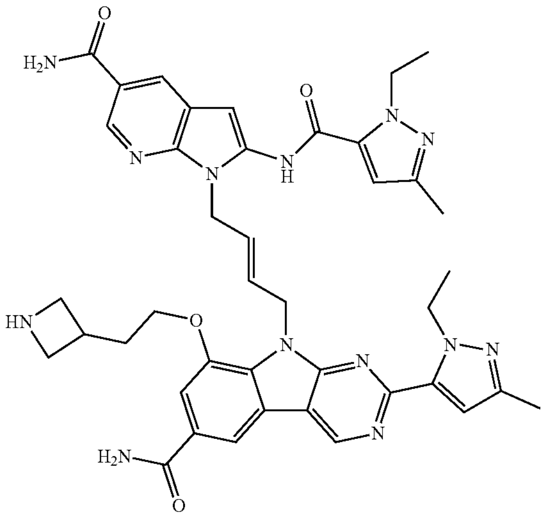 [SMILES: CCn1nc(C)cc1C(=O)Nc1cc2cc(C(N)=O)cnc2n1C/C=C/Cn1c2nc(-c3cc(C)nn3CC)ncc2c2cc(C(N)=O)cc(OCCC3CNC3)c21]

-continued
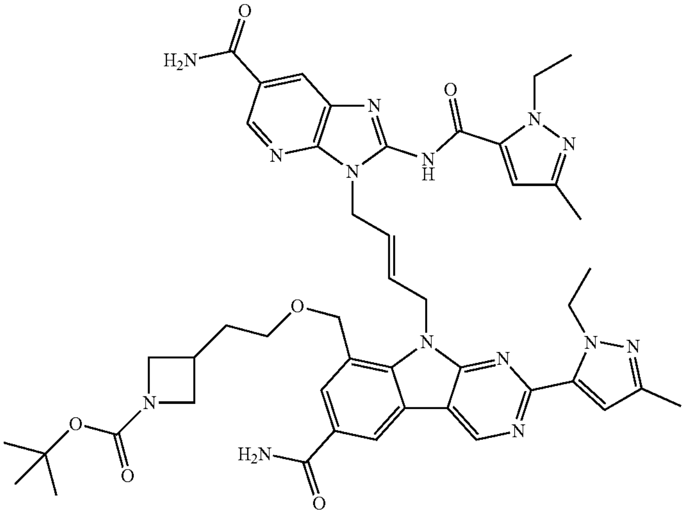 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(COCCC3CN(C(=O)OC(C)(C)C)C3)c21]
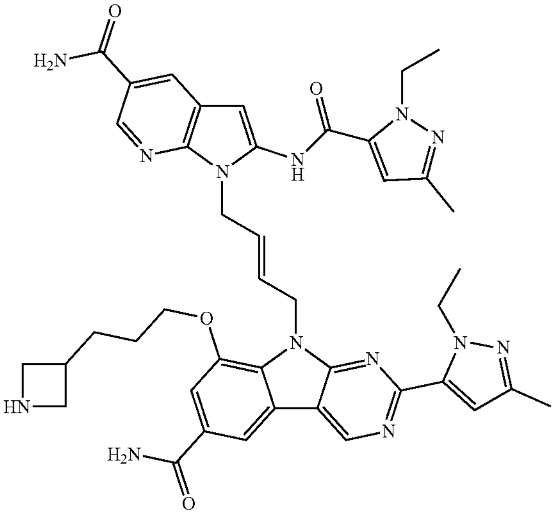 [SMILES: CCn1nc(C)cc1C(=O)Nc1cc2cc(C(N)=O)cnc2n1C/C=C/Cn1c2nc(-c3cc(C)nn3CC)ncc2c2cc(C(N)=O)cc(OCCCC3CNC3)c21]
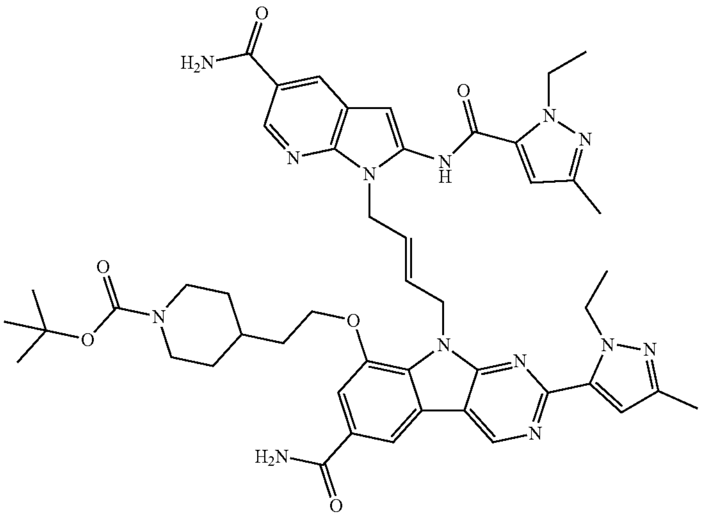 [SMILES: CCn1nc(C)cc1C(=O)Nc1cc2cc(C(N)=O)cnc2n1C/C=C/Cn1c2nc(-c3cc(C)nn3CC)ncc2c2cc(C(N)=O)cc(OCCC3CCN(C(=O)OC(C)(C)C)CC3)c21]

-continued
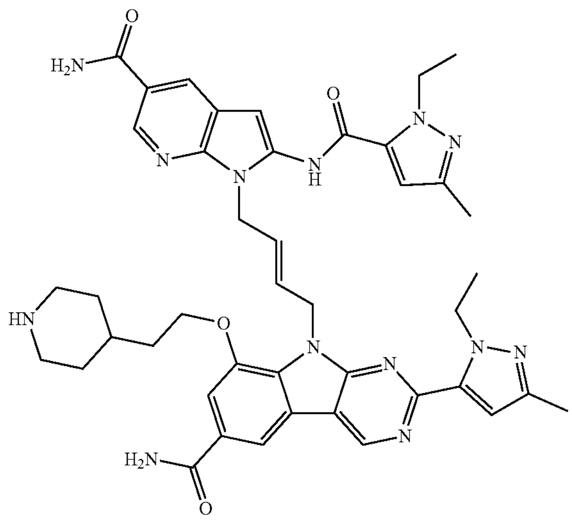 [SMILES: CCn1nc(C)cc1C(=O)Nc1cc2cc(C(N)=O)cnc2n1C/C=C/Cn1c2nc(-c3cc(C)nn3CC)ncc2c2cc(C(N)=O)cc(OCCC3CCNCC3)c21]
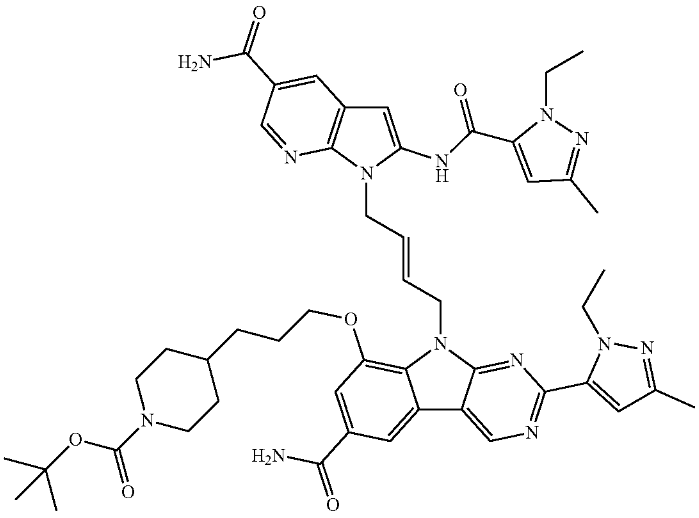 [SMILES: CCn1nc(C)cc1C(=O)Nc1cc2cc(C(N)=O)cnc2n1C/C=C/Cn1c2nc(-c3cc(C)nn3CC)ncc2c2cc(C(N)=O)cc(OCCCC3CCN(C(=O)OC(C)(C)C)CC3)c21]
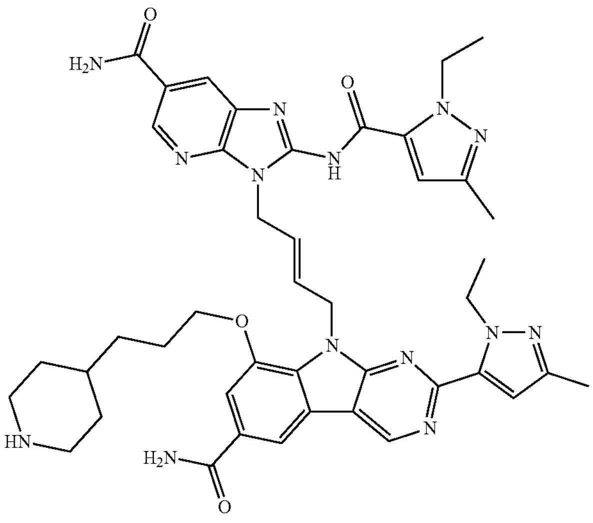 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCC3CCNCC3)c21]

-continued
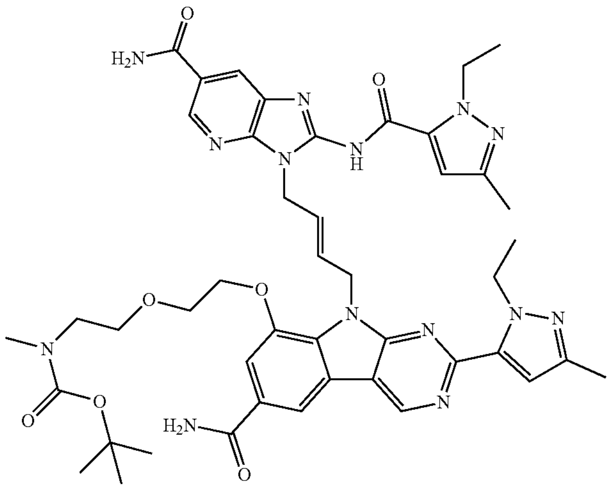
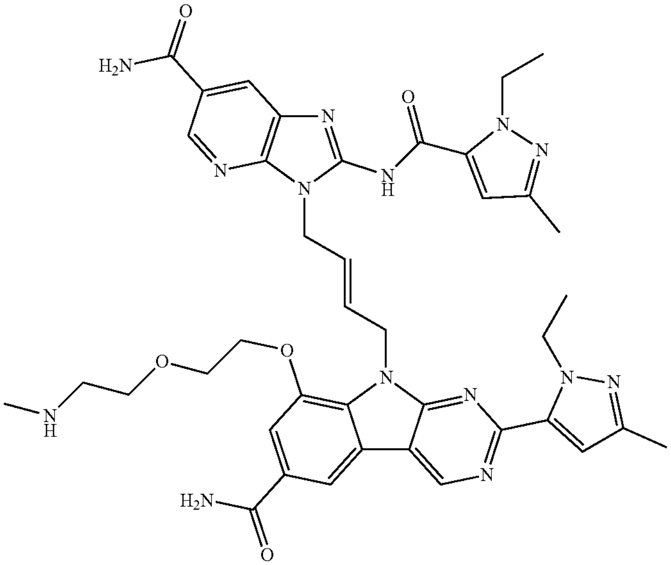
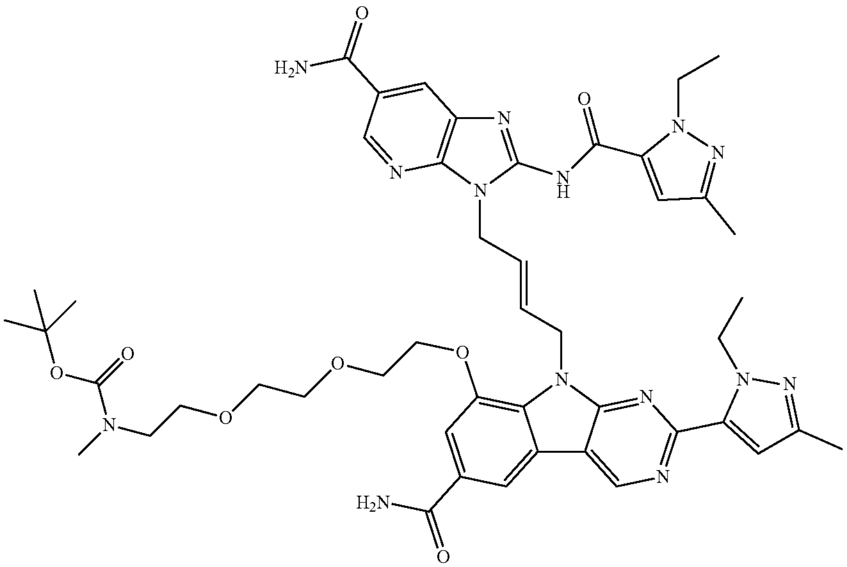 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCOCCOCCN(C)C(=O)OC(C)(C)C)c21]

-continued
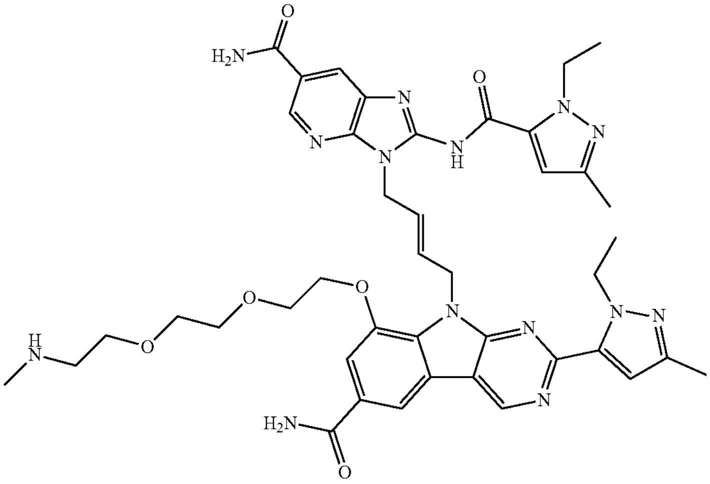
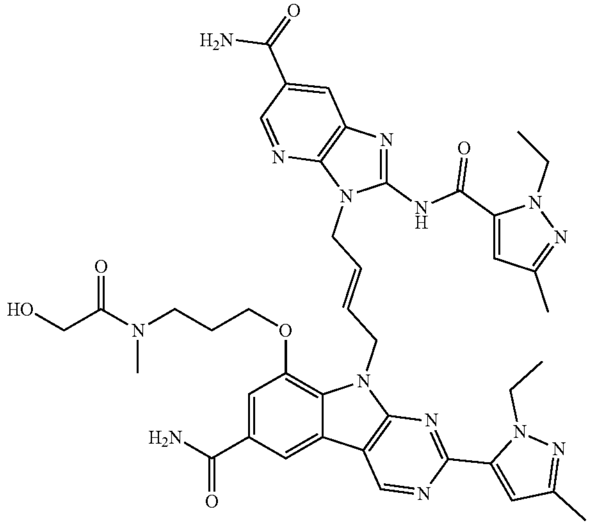 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN(C)C(=O)CO)c21]
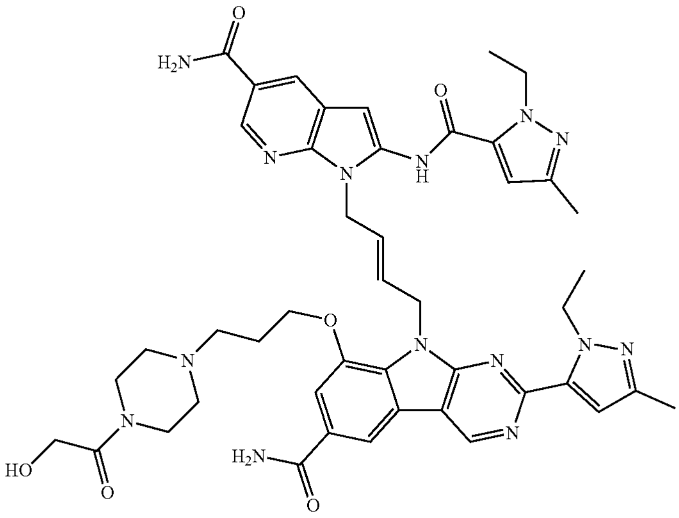 [SMILES: CCn1nc(C)cc1C(=O)Nc1cc2cc(C(N)=O)cnc2n1C/C=C/Cn1c2nc(-c3cc(C)nn3CC)ncc2c2cc(C(N)=O)cc(OCCCN3CCN(C(=O)CO)CC3)c21]

-continued

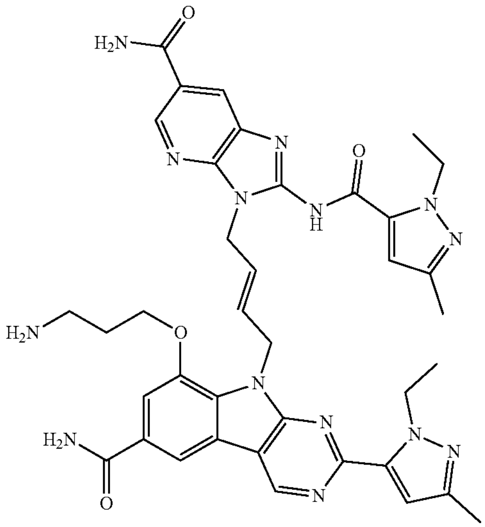 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN)c21]

or a pharmaceutically acceptable salt, stereoisomer, tautomer or prodrug thereof.

In the second aspect, disclosed herein is a pharmaceutical composition comprising the compound disclosed herein, or a pharmaceutically acceptable salt thereof, and at least one pharmaceutically acceptable carrier or excipient.

In the third aspect, disclosed herein is a method of treating a disease that can be affected by STING modulation, comprises administrating a subject in need thereof an effective amount of a compound disclosed herein or a pharmaceutically acceptable salt, stereoisomer, tautomer or prodrug thereof.

The disease is selected from inflammation, allergic and autoimmune diseases, infectious diseases, cancer, or pre-cancerous syndromes.

In the fourth aspect, disclosed herein the use of the compounds herein or a pharmaceutically acceptable salt, stereoisomer, tautomer or prodrug thereof in the preparation of a medicament for treating a disease that can be affected by STING modulation.

The disease is inflammation, allergic and autoimmune diseases, infectious diseases, cancer, or pre-cancerous syndromes.

DETAILED DESCRIPTION OF THE INVENTION

The following terms have the indicated meanings throughout the specification:

Unless specifically defined elsewhere in this document, all other technical and scientific terms used herein have the meaning commonly understood by one of ordinary skill in the art to which this invention belongs.

The following terms have the indicated meanings throughout the specification:

As used herein, including the appended claims, the singular forms of words such as "a", "an", and "the", include their corresponding plural references unless the context clearly indicates otherwise.

The term "or" is used to mean, and is used interchangeably with, the term "and/or" unless the context clearly dictates otherwise.

The term "alkyl" includes a hydrocarbon group selected from linear and branched, saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

The term "propyl" includes 1-propyl or n-propyl ("n-Pr"), 2-propyl or isopropyl ("i-Pr").

The term "butyl" includes 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu").

The term "pentyl" includes 1-pentyl, 2-pentyl, 3-pentyl, 2-methyl-2-butyl, 3-methyl-2-butyl, 3-methyl-1-butyl, 2-methyl-1-butyl.

The term "hexyl" includes 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

The term "alkylene" refers to a divalent alkyl group by removing two hydrogen atoms from an alkane. Alkylene includes but not limited to methylene, ethylene, propylene, and so on.

The term "halogen" includes fluoro (F), chloro (Cl), bromo (Br) and iodo (I).

The term "alkenyl" includes a hydrocarbon group selected from linear and branched hydrocarbon groups comprising at least one C═C double bond and from 2 to 18, such as from 2 to 8, further such as from 2 to 6, carbon atoms. Examples of the alkenyl group, e.g., $C_{2-6}$ alkenyl, include, but not limited to ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkenylene" refers to a divalent alkenyl group by removing two hydrogens from an alkene. Alkenylene includes but not limited to, vinylidene, butenylene, and so on.

The term "alkynyl" includes a hydrocarbon group selected from linear and branched hydrocarbon group, comprising at least one C≡C triple bond and from 2 to 18, such as 2 to 8, further such as from 2 to 6, carbon atoms. Examples of the alkynyl group, e.g., $C_{2-6}$ alkynyl, include, but not limited to ethynyl, 1-propynyl, 2-propynyl (propargyl), 1-butynyl, 2-butynyl, and 3-butynyl groups.

The term "alkynylene" refers to a divalent alkynyl group by removing two hydrogens from an alkyne. Alkenylene includes but not limited to ethynylene and so on.

The term "cycloalkyl" includes a hydrocarbon group selected from saturated cyclic hydrocarbon groups, comprising monocyclic and polycyclic (e.g., bicyclic and tricyclic) groups including fused, bridged or spiro cycloalkyl.

For example, the cycloalkyl group may comprise from 3 to 12, such as from 3 to 10, further such as 3 to 8, further such as 3 to 6, 3 to 5, or 3 to 4 carbon atoms. Even further for example, the cycloalkyl group may be selected from a monocyclic group comprising from 3 to 12, such as from 3 to 10, further such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. In particular, examples of the saturated monocyclic cycloalkyl group, e.g., $C_{3-8}$cycloalkyl, include, but not limited to cyclopropyl, cyclobutyl, cyclopentyl, cyclohexyl, cycloheptyl, and cyclooctyl groups. In a preferred embodiment, the cycloalkyl is a monocyclic ring comprising 3 to 6 carbon atoms (abbreviated as $C_{3-6}$ cycloalkyl), including but not limited to, cyclopropyl, cyclobutyl, cyclopentyl, and cyclohexyl. Examples of the bicyclic cycloalkyl groups include those having from 7 to 12 ring atoms arranged as a fused bicyclic ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. Further Examples of the bicyclic cycloalkyl groups include those arranged as a bicyclic ring selected from [5,6] and [6,6] ring systems.

The term "spiro cycloalkyl" includes a cyclic structure which contains carbon atoms and is formed by at least two rings sharing one atom.

The term "fused cycloalkyl" includes a bicyclic cycloalkyl group as defined herein which is saturated and is formed by two or more rings sharing two adjacent atoms.

The term "bridged cycloalkyl" includes a cyclic structure which contains carbon atoms and is formed by two rings sharing two atoms which are not adjacent to each other. The term "7 to 10 membered bridged cycloalkyl" includes a cyclic structure which contains 7 to 12 carbon atoms and is formed by two rings sharing two atoms which are not adjacent to each other.

Examples of fused cycloalkyl, fused cycloalkenyl, or fused cycloalkynyl include but are not limited to bicyclo[1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$cycloalkenyl, 2,3-dihydro-1H-indenyl, 1H-indenyl, 1, 2, 3,4-tetralyl, 1,4-dihydronaphthyl, etc. Preferred embodiments are 8 to 9 membered fused rings, which refer to cyclic structures containing 8 to 9 ring atoms within the above examples.

The term "aryl" used alone or in combination with other terms includes a group selected from:

(a) 5- and 6-membered carbocyclic aromatic rings, e.g., phenyl;

(b) bicyclic ring systems such as 7 to 12 membered bicyclic ring systems, wherein at least one ring is carbocyclic and aromatic, e.g., naphthyl and indanyl; and, (c) tricyclic ring systems such as 10 to 15 membered tricyclic ring systems wherein at least one ring is carbocyclic and aromatic, e.g., fluorenyl.

The terms "aromatic hydrocarbon ring" and "aryl" are used interchangeably throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring include, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

Specifically, the term "bicyclic fused aryl" includes a bicyclic aryl ring as defined herein. The typical bicyclic fused aryl is naphthalene.

The term "heteroaryl" includes a group selected from:

(a) 5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;

(b) 7- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and (c) 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides.

Specifically, the term "bicyclic fused heteroaryl" includes a 7- to 12-membered, preferably 7- to 10-membered, more preferably 9- or 10-membered fused bicyclic heteroaryl ring as defined herein. Typically, a bicyclic fused heteroaryl is 5-membered/5-membered, 5-membered/6-membered, 6-membered/6-membered, or 6-membered/7-membered bicyclic. The group can be attached to the remainder of the molecule through either ring.

"Heterocyclyl", "heterocycle" or "heterocyclic" are interchangeable and include a non-aromatic heterocyclyl group comprising one or more heteroatoms selected from nitrogen, oxygen or optionally oxidized sulfur as ring members, with the remaining ring members being carbon, including monocyclic, fused, bridged, and spiro ring, i.e., containing monocyclic heterocyclyl, bridged heterocyclyl, spiro heterocyclyl, and fused heterocyclic groups.

The term "at least one substituent" disclosed herein includes, for example, from 1 to 4, such as from 1 to 3, further as 1 or 2, substituents, provided that the theory of valence is met. For example, "at least one substituent F" disclosed herein includes from 1 to 4, such as from 1 to 3, further as 1 or 2, substituents F.

The term "divalent" refers to a linking group capable of forming covalent bonds with two other moieties. For example, "a divalent cycloalkyl group" refers to a cycloalkyl group obtained by removing two hydrogens from the corresponding cycloalkane to form a linking group. the term "divalent aryl group", "divalent heterocyclyl group" or "divalent heteroaryl group" should be understood in a similar manner.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, a reference to one isomer applies to any of the possible isomers. Whenever the isomeric composition is unspecified, all possible isomers are included.

When compounds disclosed herein contain olefinic double bonds, unless specified otherwise, such double bonds are meant to include both E and Z geometric isomers.

When compounds disclosed herein contain a di-substituted cyclic ring system, substituents found on such a ring system may adopt cis and trans formations. Cis formation means that both substituents are found on the upper side of the 2 substituent placements on the carbon, while trans would mean that they were on opposing sides. For example, the di-substituted cyclic ring system may be cyclohexyl or cyclobutyl ring.

It may be advantageous to separate reaction products from one another and/or from starting materials. The desired products of each step or series of steps are separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art could select and apply the techniques most likely to achieve the desired separation.

"Diastereomers" refer to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "*Chromatographic resolution of enantiomers: Selective review.*" *J. Chromatogr.,* 113(3) (1975): pp. 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., Ed. *Drug Stereochemistry: Analytical Methods and Pharmacology*. New York: Marcel Dekker, Inc., 1993.

Some of the compounds disclosed herein may exist with different points of attachment of hydrogen, referred to as tautomers. For example, compounds including carbonyl $—CH_2C(O)—$ groups (keto forms) may undergo tautomerism to form hydroxyl $—CH{=}C(OH)—$ groups (enol forms). Both keto and enol forms, individually as well as mixtures thereof, are also intended to be included where applicable.

"Prodrug" refers to a derivative of an active agent that requires a transformation within the body to release the active agent. In some embodiments, the transformation is an enzymatic transformation. Prodrugs are frequently, although not necessarily, pharmacologically inactive until converted to the active agent.

"Pharmaceutically acceptable salts" refer to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base. The term also includes salts of the stereoisomers (such as enantiomers and/or diastereomers), tautomers and prodrugs of the compound of the invention.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as a compound that, when administered to a subject for treating a disease, or at least one of the clinical symptoms of a disease or disorder, is sufficient to affect such treatment for the disease, disorder, or symptom. The term "therapeutically effective amount" can vary with the compound, the disease, disorder, and/or symptoms of the disease or disorder, the severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer, tautomer or prodrug thereof, and/or at least one pharmaceutically acceptable salt thereof disclosed herein effective to "treat" as defined herein, a disease or disorder in a subject. In the case of combination therapy, the term "therapeutically effective amount" refers to the total amount of the combination objects for the effective treatment of a disease, a disorder or a condition.

The term "disease" refers to any disease, discomfort, illness, symptoms or indications, and can be interchangeable with the term "disorder" or "condition".

Throughout this specification and the claims which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the claims which follow, the term "$C_{n-m}$" indicates a range which includes the endpoints, wherein n and m are integers and indicate the number of carbons. Examples include $C_{1-8}$, $C_{1-6}$, and the like.

Unless specifically defined elsewhere in this document, all other technical and scientific terms used herein have the meaning commonly understood by one of ordinary skill in the art to which this invention belongs.

General Synthesis

Compounds disclosed herein, including salts thereof, can be prepared using known organic synthesis techniques and can be synthesized according to any of numerous possible synthetic routes.

The reaction for preparing compounds disclosed herein can be carried out in suitable solvents which can be readily selected by one of skill in the art of organic synthesis. Suitable solvents can be substantially non-reactive with the starting materials, the intermediates, or products at the temperatures at which the reactions are carried out, e.g., temperatures which can range from the solvent's boiling temperature. A given reaction can be carried out in one solvent or mixture of solvents.

The selection of an appropriate protecting group can be readily determined by one skilled in the art.

Reactions can be monitored according to any suitable method known in the art, such as NMR, UV, HPLC, LC-MS and TLC. Compounds can be purified by a variety of methods, including HPLC and normal phase silica chromatography.

Chiral analytic HPLC was used for the retention time analysis of different chiral examples, the conditions were divided into the methods as below according to the column, mobile phase, solvent ratio used.

Scheme I

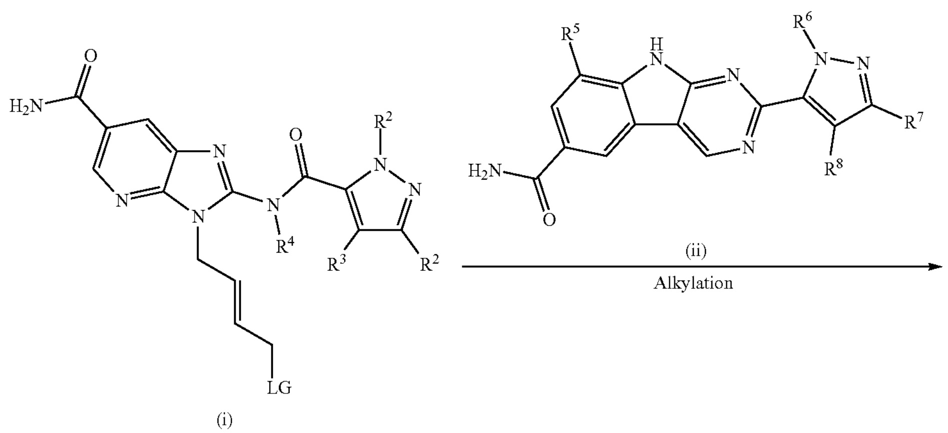

-continued
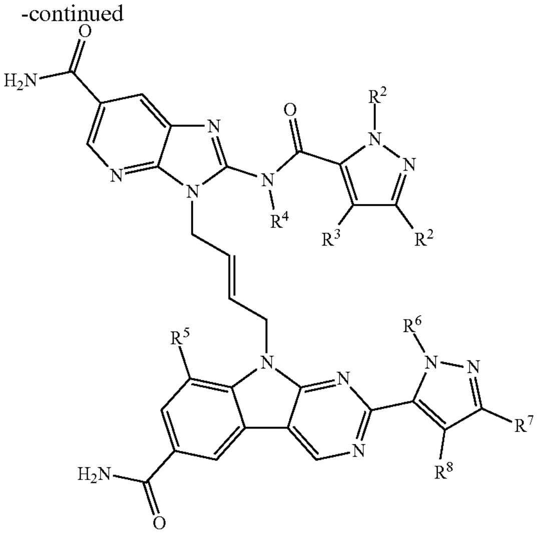
(iii)
Formula (I)
LG is a suitable leaving group that is selected from halogens or pseudohalogens.
For example, compounds of Formula (I) can be formed as shown in Scheme I. Compound (ii) can be alkylated with compound (i) to give compound (iii) [i.e., Formula (I)], wherein $R^1$, $R^2$, $R^3$, $R^4$, $R^5$, $R^6$, $R^7$ and $R^8$ are defined as described herein.
Scheme II
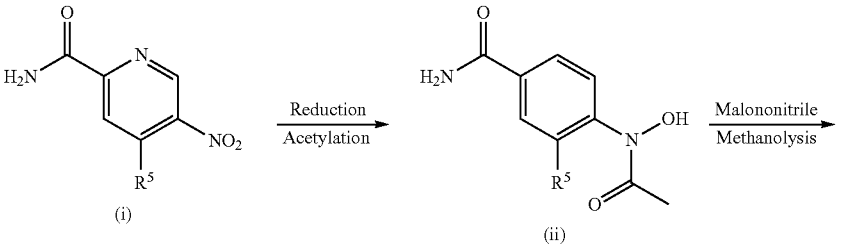
(i) (ii)
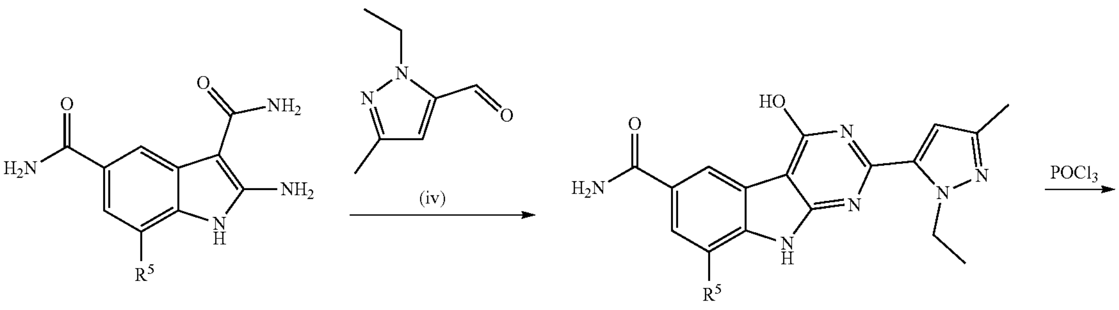
(iii) (v)

-continued
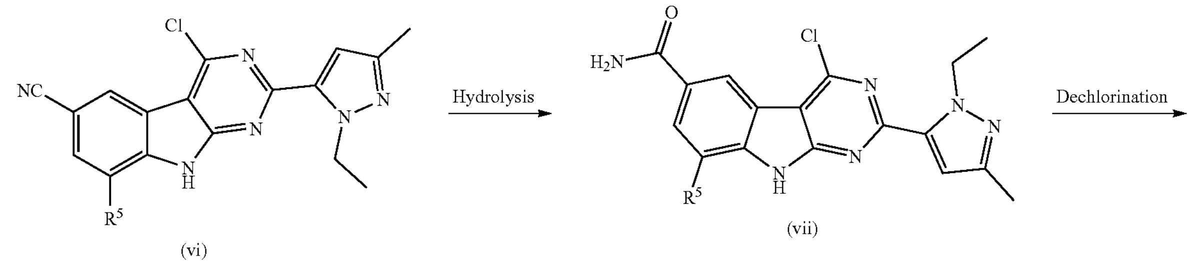
(vi) (vii)
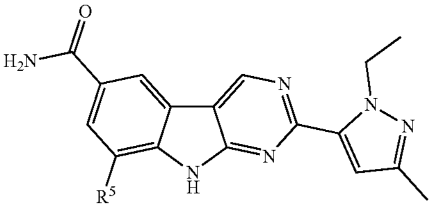
(viii)
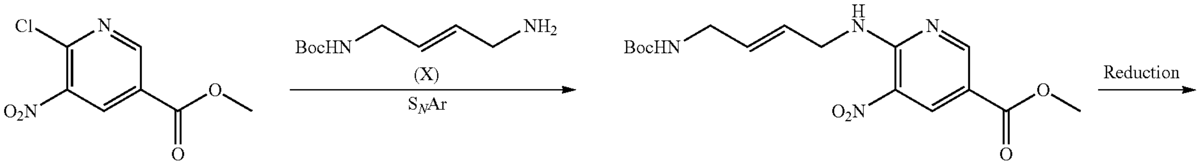
(ix) (xi)
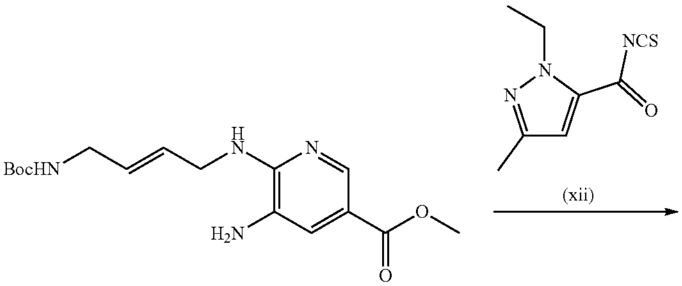
(xii)
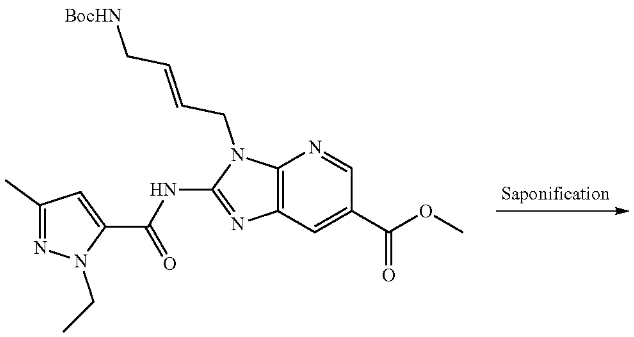
(xiii)

-continued
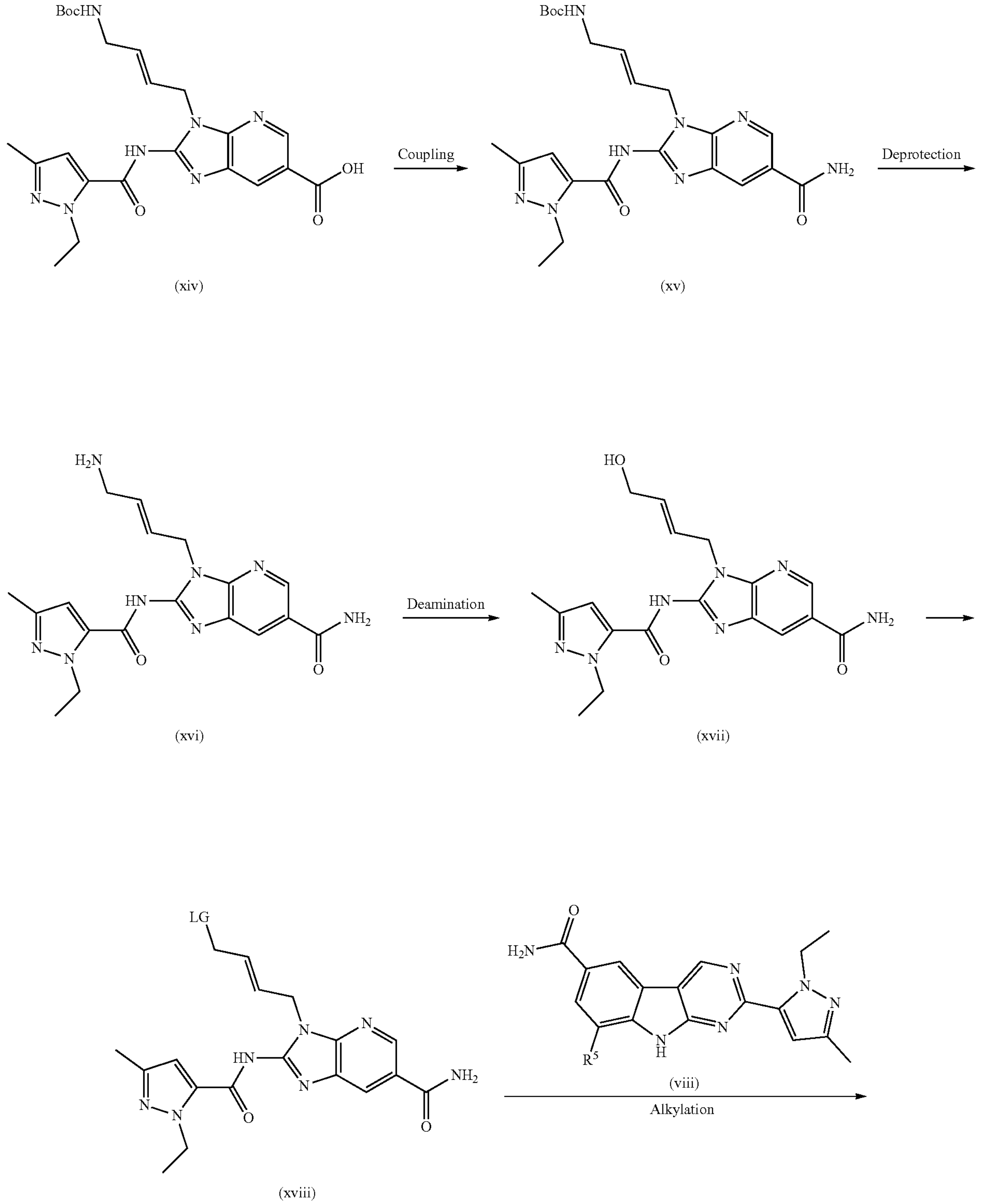
(xiv) (xv)
(xvi) (xvii)
(xviii) (viii)

-continued

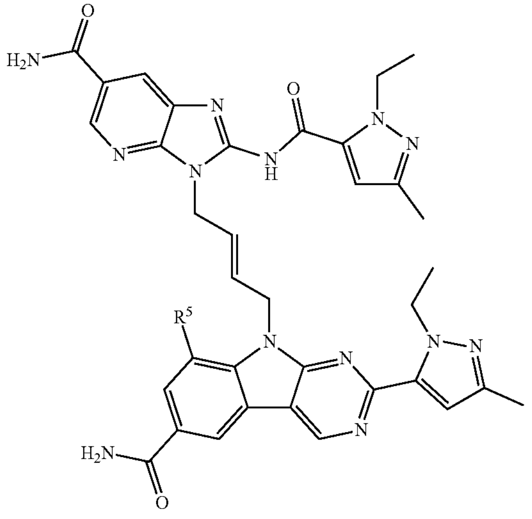

(xiv)
Formula (II)

LG is a suitable leaving group that is selected from halogens or pseudohalogens.

For example, compounds of Formula (II) can be formed as shown in Scheme II, wherein $R^5$ is defined as described herein. Compound (i) can be reduced followed by acetylation to give compound (ii); compound (ii) can be reacted with malononitrile followed by treatment with basic methanol to give compound (iii); compound (iii) can be condensed with aldehyde (iv) to give compound (v); compound (v) can react with $POCl_3$ to give compound (vi); compound (vi) can be hydrolyzed to give compound (vii); compound (vii) can be dechlorinated to give compound (viii). Compound (ix) can be substituted by compound (x) to give compound (xi); compound (xi) can be reduced to give compound (xii); compound (xii) can be acylated to give compound (xiii); compound (xiii) can be saponified to give compound (xiv); compound (xiv) can be coupled to give compound (xv); compound (xv) can be deprotected to give compound (xvi); compound (xvi) can be deaminated to give compound (xvii); the hydroxyl group on compound (xvii) can be transformed to a leaving group to give compound (xviii); compound (xviii) can be reacted with compound (viii) to furnish compound (xiv) [i.e., Formula (II)].

Scheme III

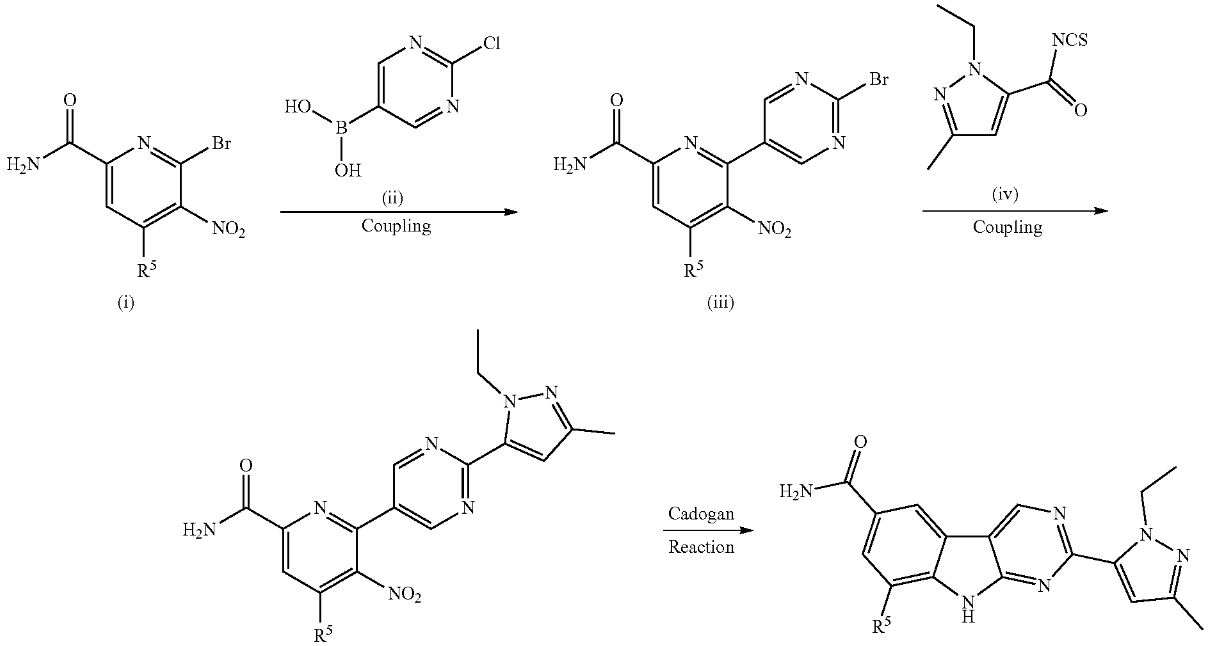

(i) (ii) (iii) (iv) (v) (viii)

-continued
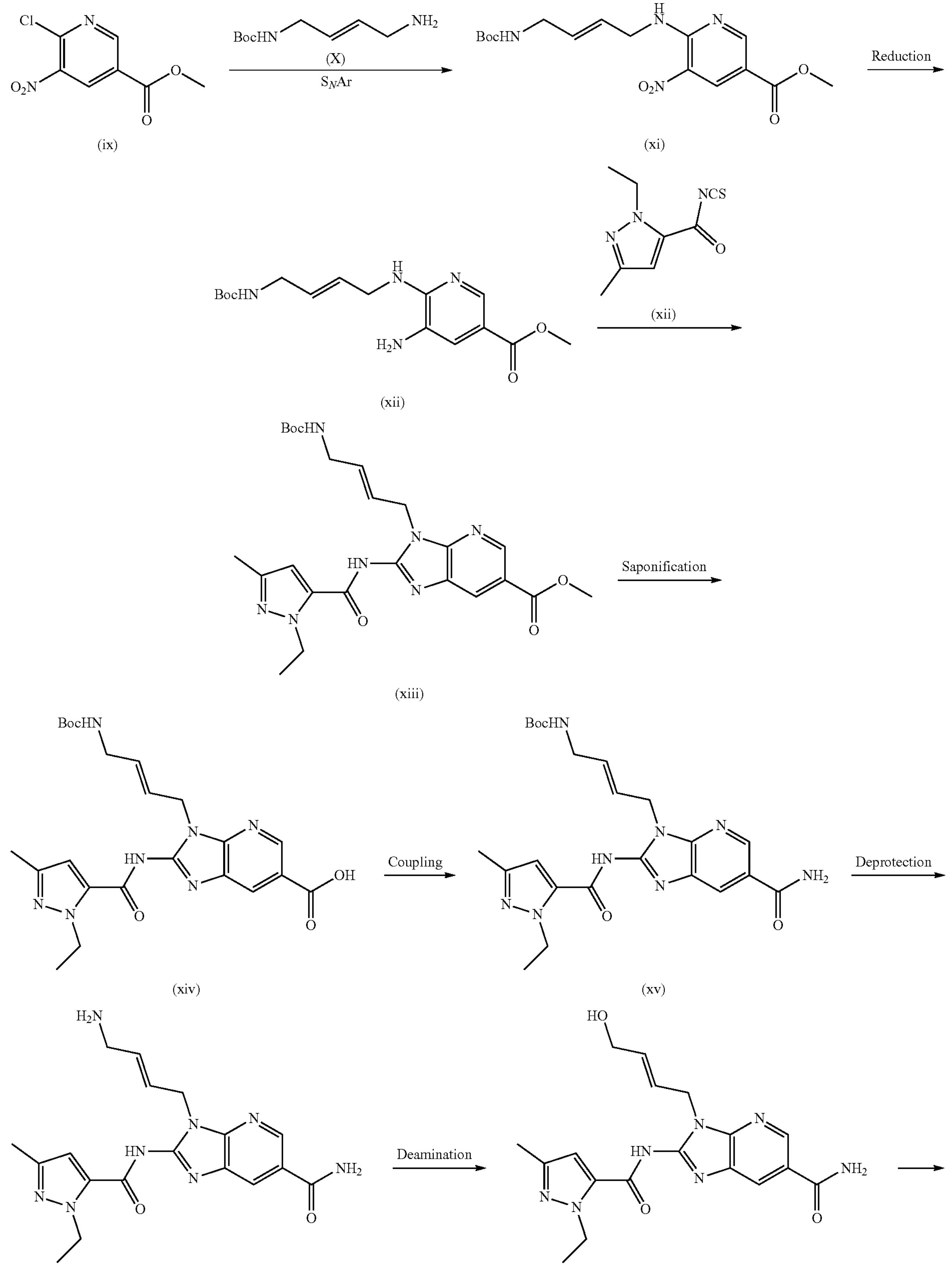
(ix) (xi) (xii) (xiii) (xiv) (xv) (xvii) (xviii)

-continued

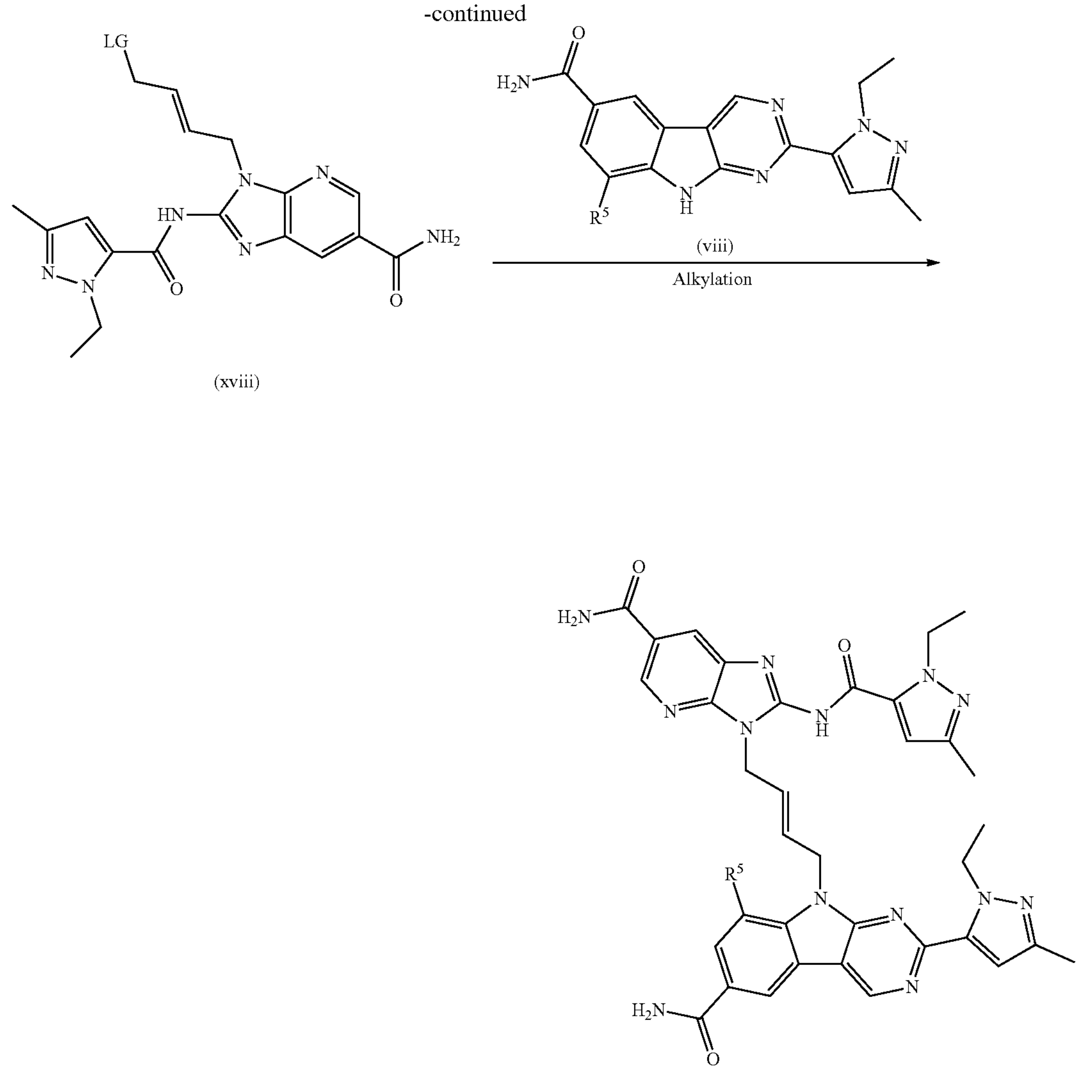

(xviii)

(xiv)
Formula (II)

LG is a suitable leaving group that is selected from halogens or pseudohalogens.

For example, compounds of Formula (II) can be formed as shown in Scheme III, wherein $R^5$ is defined as described herein. Compound (i) can be coupled with compound (ii) with transition metal catalyzed reaction to give compound (iii); compound (iii) can be coupled with compound (iv) with transition metal catalyzed reaction to give compound (v); compound (v) can be intramolecularly arylated through a Cadogan reaction to give compound (viii). Compound (xviii) can be obtained through the method illustrated in Scheme II, then reacted with compound (viii) to give compound (xiv) [i.e., Formula (II)].

Abbreviations

NMR nuclear magnetic resonance
DMSO dimethyl sulfoxide
LC-MS liquid chromatograph mass spectrometer
HPLC high performance liquid chromatography
UV ultraviolet
PE petroleum ether
EA ethyl acetate
Boc t-butoxycarbonyl
DCM dichloromethane
HATU 1-[bis(dimethylamino)methylene]-1H-1,2,3-triazolo[4,5-b]pyridinium 3-oxid hexafluorophosphate
DIPEA, DIEA N,N-diisopropylethylamine
DMF N,N-dimethylformamide
Et ethyl
Ac acetyl
THF tetrahydrofuran
Bu butyl
MTBE methyl tert-butyl ether
dppf 1,1'-ferrocenediyl-bis(diphenylphosphine)
IPA isopropanol
TFA trifluoroacetic acid Example 1-AA Tert-butyl (E)-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)methyl)carbamate

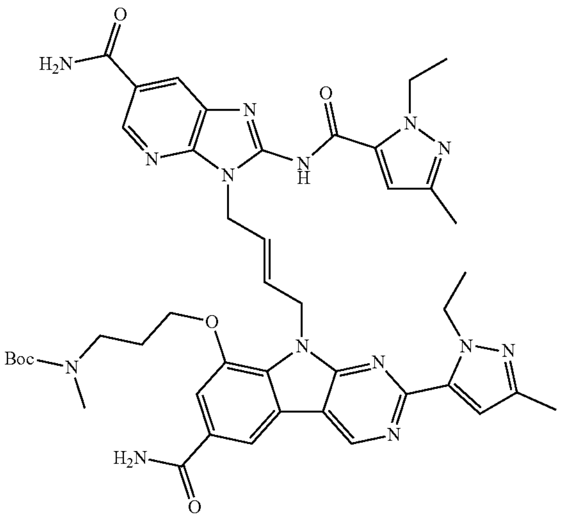 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN(C)C(=O)OC(C)(C)C)c21]

Step 1: 1-ethyl-3-methyl-1H-pyrazole-5-carbonyl isothiocyanate

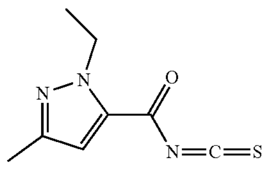

To a solution of 1-ethyl-3-methyl-1H-pyrazole-5-carboxylic acid (12.7 g, 82.5 mmol) and N,N-dimethylformamide (0.1 mL) in dichloromethane (150 mL) under nitrogen was added oxalyl chloride (10.5 g, 82.5 mmol) dropwise and then the mixture was stirred at 0° C. for 1 h. The solvent was evaporated under vacuum and the crude was co-evaporated twice with dichloromethane (50 mL×2). The crude material was dissolved in anhydrous acetone (20 mL) then dropwise added into a solution of KSCN (8.0 g, 82.5 mmol) in acetone (100 mL) at 0° C. The mixture was stirred for 10 min at 0° C. Additional KSCN (1.6 g) was added and the mixture was stirred for 20 min. Hexane (100 mL) was added to the reaction mixture and the biphasic mixture was concentrated in vacuo to one third of the volume. The process of hexanes addition (200 mL) and concentration was repeated twice, then hexanes (200 mL) was added and the solid was removed by filtration. The solid was rinsed with hexanes (50 mL). The combined filtrate was concentrated and the residue was purified by column chromatography (PE/EtOAc=6/1) to give the title compound (10.0 g, 62%).

Step 2: methyl (E)-6-((4-((tert-butoxycarbonyl)amino)but-2-en-1-yl)amino)-5-nitronicotinate

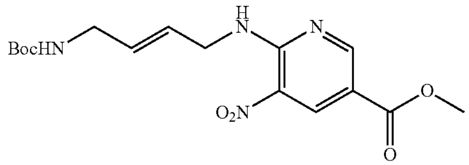 [SMILES: COC(=O)c1cnc(NC/C=C/CNC(=O)OC(C)(C)C)c([N+](=O)[O-])c1]

A solution of methyl 6-chloro-5-nitronicotinate (2.4 g, 11 mmol), tert-butyl (E)-(4-aminobut-2-en-1-yl)carbamate (2.06 g, 11 mmol) and N,N-diisopropylethylamine (2.84 g, 22 mmol) in ethanol (60 mL) was stirred at 55° C. for 2 h. The mixture was cooled to room temperature and concentrated under reduced pressure. The residue was dissolved in ethyl acetate (150 mL), successively washed with water (50 mL) and brine (50 mL), dried over $Na_2SO_4$, filtered and concentrated. The residue was purified by column chromatography (PE/EtOAc=5/1) to give the title compound (3.3 g, 82%). $^1H$ NMR (400 MHz, DMSO-d6) δ 9.06 (s, 1H), 8.90 (d, J=1.8 Hz, 1H), 8.74 (d, J=2.0 Hz, 1H), 6.96 (s, 1H), 5.72-5.51 (m, 2H), 4.22 (s, 2H), 3.85 (s, 3H), 3.51 (s, 2H), 1.35 (s, 9H). LC-MS $(M+H)^+$=367.1.

Step 3: methyl (E)-5-amino-6-((4-((tert-butoxycarbonyl)amino)but-2-en-1-yl)amino)nicotinate

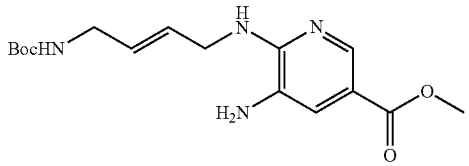

To a solution of methyl (E)-6-((4-((tert-butoxycarbonyl)amino)but-2-en-1-yl)amino)-5-nitronicotinate (3.3 g, 9.0 mmol) in methanol (60 mL) was added ammonia water (25%, 1 mL) and a solution of $Na_2S_2O_4$ (15.7 g, 90 mmol) in water (60 mL) at 0° C. and the mixture was stirred at room temperature for 4 h. The mixture was diluted with water (200 mL) and extracted with ethyl acetate (150 mL×4). The combined organic layer was washed with brine (100 mL), dried over $Na_2SO_4$, filtered and concentrated to give the title compound (1.8 g, 59%). $^1H$ NMR (400 MHz, DMSO-d6) δ 8.02 (s, 1H), 7.15 (s, 1H), 6.97 (s, 1H), 6.49 (s, 1H), 5.63-5.57 (m, 2H), 4.99 (s, 2H), 4.02 (s, 2H), 3.74 (s, 3H), 3.53 (s, 2H), 1.36 (s, 9H). LC-MS $(M+H)^+$=337.2.

Step 4: methyl (E)-3-(4-((tert-butoxycarbonyl) amino)but-2-en-1-yl)-2-(1-ethyl-3-methyl-1H-pyrazole-5-carboxamido)-3H-imidazo[4,5-b]pyridine-6-carboxylate

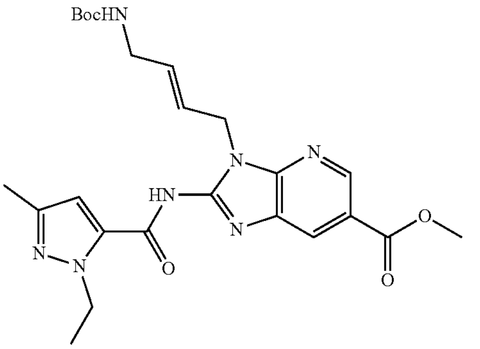

To a solution of methyl (E)-5-amino-6-((4-((tert-butoxycarbonyl)amino)but-2-en-1-yl)amino)nicotinate (1.8 g, 5.34 mmol) in N,N-dimethylformamide (20 mL) was added a solution of 1-ethyl-3-methyl-1H-pyrazole-5-carbonyl isothiocyanate (937 mg, 4.81 mmol) in 1,4-dioxane (10 mL) dropwise slowly over a period of 20 min. The mixture was stirred at room temperature for 15 min, then N-(3-dimethylaminopropyl)-N'-ethylcarbodiimide hydrochloride (1.54 g, 8.01 mmol) and triethylamine (1.35 g, 13.35 mmol) was added. The mixture was stirred at room temperature for overnight. The mixture was poured to water and extracted with ethyl acetate (100 mL×4). The combined organic layer was washed with brine (100 mL), dried over $Na_2SO_4$, filtered and concentrated. The residue was purified by column chromatography (DCM/MeOH=150/1 to 80/1, contains 0.1% ammonia water) to give the title compound (940 mg, 35%). $^1$H NMR (400 MHz, DMSO-d6) δ 12.93 (s, 1H), 8.81 (s, 1H), 8.17 (s, 1H), 6.94 (s, 1H), 6.71 (s, 1H), 5.76-5.64 (m, 2H), 4.79 (s, 2H), 4.60 (d, J=6.9 Hz, 2H), 3.90 (s, 3H), 3.50 (s, 2H), 2.19 (s, 3H), 1.43-1.28 (m, 12H). LC-MS $(M+H)^+$ =498.2.

Step 5: (E)-3-(4-((tert-butoxycarbonyl)amino)but-2-en-1-yl)-2-(1-ethyl-3-methyl-1H-pyrazole-5-carboxamido)-3H-imidazo[4,5-b]pyridine-6-carboxylic acid

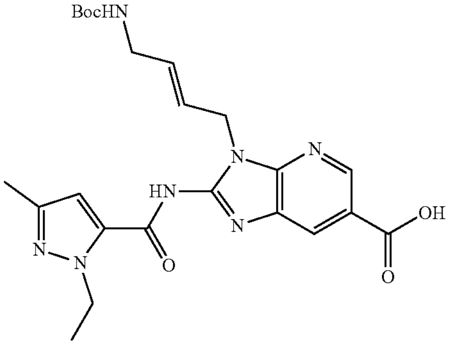 [SMILES: CCn1nc(C)cc1C(=O)Nc1nc2cc(C(=O)O)cnc2n1C/C=C/CNC(=O)OC(C)(C)C]

To a solution of methyl (E)-3-(4-((tert-butoxycarbonyl) amino)but-2-en-1-yl)-2-(1-ethyl-3-methyl-1H-pyrazole-5-carboxamido)-3H-imidazo[4,5-b]pyridine-6-carboxylate (760 mg, 1.53 mmol) in methanol (30 mL) was added a solution of NaOH (122 mg, 3.07 mmol) in water (3 mL) and the mixture was stirred at 70° C. for overnight. The mixture was neutralized with HCl (1 N) to pH 7 and then concentrated. The residue was dissolved in methanol (10 mL) and solid was filtered off. The filtrate was concentrated to give the title compound (700 mg, 94%). $^1$H NMR (400 MHz, DMSO-d6) δ 13.25 (s, 1H), 12.92 (s, 1H), 8.79 (s, 1H), 8.17 (s, 1H), 6.95 (s, 1H), 6.71 (s, 1H), 5.73-5.64 (m, 2H), 4.79 (s, 2H), 4.60 (d, J=7.0 Hz, 2H), 3.50 (s, 2H), 2.19 (s, 3H), 1.43-1.10 (m, 12H). LC-MS $(M+H)^+$=484.2.

Step 6: tert-butyl (E)-(4-(6-carbamoyl-2-(1-ethyl-3-methyl-1H-pyrazole-5-carboxamido)-3H-imidazo[4,5-b]pyridin-3-yl)but-2-en-1-yl)carbamate

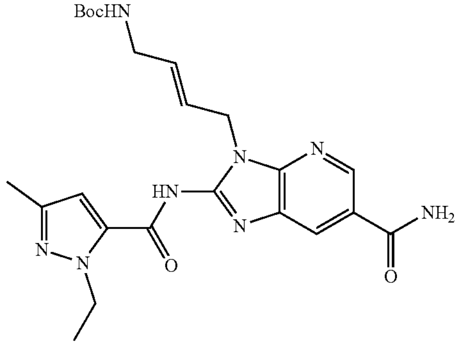 [SMILES: CCn1nc(C)cc1C(=O)Nc1nc2cc(C(N)=O)cnc2n1C/C=C/CNC(=O)OC(C)(C)C]

To a mixture of (E)-3-(4-((tert-butoxycarbonyl)amino) but-2-en-1-yl)-2-(1-ethyl-3-methyl-1H-pyrazole-5-carboxamido)-3H-imidazo[4,5-b]pyridine-6-carboxylic acid (700 mg, 1.45 mmol), HATU (581 mg, 1.53 mmol), $NH_4Cl$ (409 mg, 7.65 mmol) and DIPEA (395 mg, 3.06 mmol) in N,N-dimethylformamide (8 mL) was stirred at room temperature for overnight. The mixture was poured to water (80 mL) and extracted with ethyl acetate (80 mL×3). The combined organic layer was washed with brine (50 mL), dried over $Na_2SO_4$, filtered and concentrated to give the title compound (560 mg, 76%). $^1$H NMR (400 MHz, DMSO-d6) δ 12.90 (s, 1H), 8.76 (s, 1H), 8.16 (d, J=12.6 Hz, 2H), 7.56 (s, 1H), 6.94 (s, 1H), 6.70 (s, 1H), 5.77-5.64 (m, 2H), 4.79 (s, 2H), 4.61 (d, J=6.0 Hz, 2H), 3.51 (s, 2H), 2.19 (s, 3H), 1.44-1.18 (m, 12H). LC-MS $(M+H)^+$=483.2.

Step 7: (E)-3-(4-aminobut-2-en-1-yl)-2-(1-ethyl-3-methyl-1H-pyrazole-5-carboxamido)-3H-imidazo[4,5-b]pyridine-6-carboxamide hydrochloride

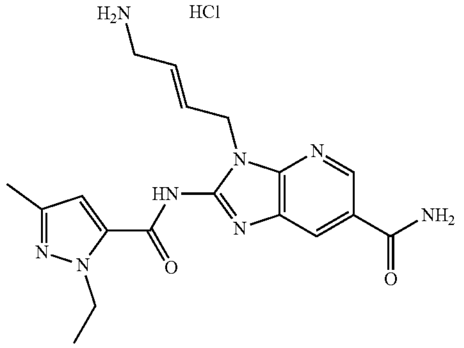 [SMILES: Cl ; CCn1nc(C)cc1C(=O)Nc1nc2cc(C(N)=O)cnc2n1C/C=C/CN]

To a solution of tert-butyl (E)-(4-(6-carbamoyl-2-(1-ethyl-3-methyl-1H-pyrazole-5-carboxamido)-3H-imidazo[4,5-b]pyridin-3-yl)but-2-en-1-yl)carbamate (560 mg, 1.16 mmol) in dichloromethane (10 mL) was added a HCl solution in 1,4-dioxane (3 mL, 4 M) and the mixture was stirred at room temperature for 2 h. The precipitate was collected by filtration and dried under vacuum to give the title compound (440 mg, 91%). $^1$H NMR (400 MHz, DMSO-d6) δ 8.77 (s, 1H), 8.21-8.16 (m, 2H), 7.90 (s, 3H), 7.58 (s, 1H), 6.73 (s, 1H), 6.05 (s, 1H), 5.68 (s, 1H), 4.86 (s, 2H), 4.60 (d, J=7.4 Hz, 2H), 3.43 (s, 2H), 2.19 (s, 3H), 1.38-1.36 (m, 3H). LC-MS $(M+H)^+$=383.2.

Step 8: (E)-2-(1-ethyl-3-methyl-1H-pyrazole-5-carboxamido)-3-(4-hydroxybut-2-en-1-yl)-3H-imidazo[4,5-b]pyridine-6-carboxamide

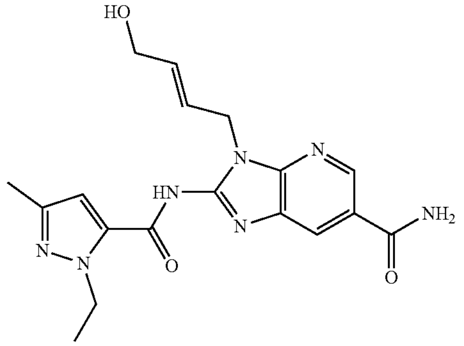 [SMILES: CCn1nc(C)cc1C(=O)Nc1nc2cc(C(N)=O)cnc2n1C/C=C/CO]

To a suspension of (E)-3-(4-aminobut-2-en-1-yl)-2-(1-ethyl-3-methyl-1H-pyrazole-5-carboxamido)-3H-imidazo[4,5-b]pyridine-6-carboxamide hydrochloride (440 mg, 1.05 mmol) in water (5 mL) was added KBr (276 mg, 2.32 mmol) and $NaNO_2$ (160 mg, 2.32 mmol) and the mixture was stirred at 70° C. for 2 h. After being cooled to room temperature, the precipitate was collected by filtration and dried to give the title compound (400 mg, 99%). $^1$H NMR (400 MHz, DMSO-d6) δ 8.75 (s, 1H), 8.16 (s, 2H), 7.52 (s, 1H), 6.69 (s, 1H), 5.82-5.75 (m, 2H), 4.81 (s, 2H), 4.61 (s, 2H), 3.90 (s, 1H), 3.39 (s, 2H), 2.18 (s, 3H), 1.35 (s, 3H). LC-MS $(M+H)^+$=384.2.

Step 9: (E)-3-(4-bromobut-2-en-1-yl)-2-(1-ethyl-3-methyl-1H-pyrazole-5-carboxamido)-3H-imidazo[4,5-b]pyridine-6-carboxamide

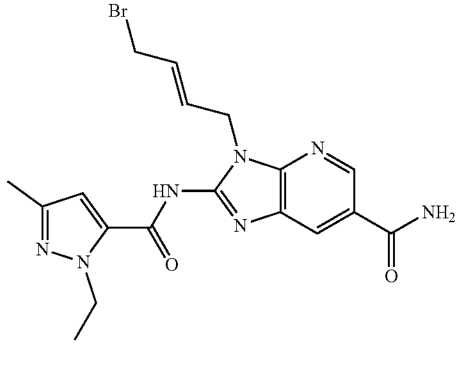 [SMILES: CCn1nc(C)cc1C(=O)Nc1nc2cc(C(N)=O)cnc2n1C/C=C/CBr]

To a solution of (E)-2-(1-ethyl-3-methyl-1H-pyrazole-5-carboxamido)-3-(4-hydroxybut-2-en-1-yl)-3H-imidazo[4,5-b]pyridine-6-carboxamide (400 mg, 1.04 mmol) in THF (30 mL) was added a solution of $PBr_3$ in dichloromethane (4 mL, 1 M) and the mixture was stirred at room temperature for overnight. The mixture was concentrated and the residue was treated with an aqueous solution of $NaHCO_3$ (1 g in 50 mL water). The solid was collected by filtration and the filtrate was extracted with ethyl acetate (50 mL). The organic layer was combined with the solid, concentrated under vacuum and purified by column chromatography (DCM/MeOH=50/1 to 20/1) to give the title compound (190 mg, 41%). $^1$H NMR (400 MHz, DMSO-d6) δ 12.92 (s, 1H), 8.75 (s, 1H), 8.16 (d, J=14.9 Hz, 2H), 7.55 (s, 1H), 6.73 (s, 1H), 6.05 (s, 1H), 5.90 (d, J=6.8 Hz, 1H), 4.85 (s, 2H), 4.60 (d, J=6.5 Hz, 2H), 4.13 (d, J=7.2 Hz, 2H), 2.18 (s, 3H), 1.36 (s, 3H). LC-MS $(M+H)^+$=446.1, 448.1.

Step 10: 1-ethyl-3-methyl-1H-pyrazole & 1-ethyl-5-methyl-1H-pyrazole

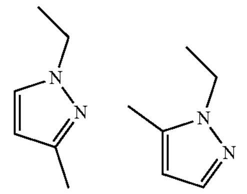

To a solution of 3-methyl-1H-pyrazole (50 g, 609 mmol) in DMF (300 mL) was added NaH (60%, 26.8 g, 670 mmol) in portions. The mixture was stirred at 0° C. for 30 min. To the mixture was added EtI (105 g, 673 mmol). The mixture was stirred at room temperature for overnight. The mixture was diluted with water (1000 mL), extracted with EtOAc (800 mL×3). The combined organic layer was washed with brine (1000 mL×3), dried over $Na_2SO_4$, filtered and concentrated to give the title compounds (62 g, 93%) as a mixture. LC-MS $(M+H)^+$=111.1.

Step 11: (1-ethyl-3-methyl-1H-pyrazol-5-yl)boronic acid

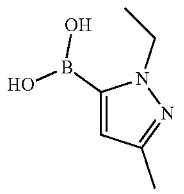

To a solution of a mixture of 1-ethyl-3-methyl-1H-pyrazole and 1-ethyl-5-methyl-1H-pyrazole (3.5 g, 31.5 mmol) in THF (50 mL) was added n-BuLi (2.5 M, 4.0 mL, 10 mmol) dropwise at −78° C. The mixture was stirred at −78° C. for 1 h. To the mixture was added triisopropyl borate (1.9 g, 10 mmol). The mixture was stirred at −78° C. for 1 h then warmed to room temperature, diluted with saturated $NH_4Cl$ solution (10 mL) then extracted with THF (30 mL×2). The combined organic layer was washed with brine (20 mL), dried over $Na_2SO_4$, filtered and concentrated. The residue was triturated with MTBE (50 mL). The solid was collected by filtration and dried under vacuum to give the title compound (0.7 g, 14%). LC-MS $(M+H)^+$=155.1.

Step 12: 3-bromo-5-fluoro-4-nitrobenzamide

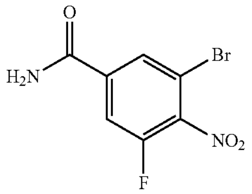 [SMILES: NC(=O)c1cc(F)c([N+](=O)[O-])c(Br)c1]

A mixture of methyl 3-bromo-5-fluoro-4-nitrobenzoate (5.0 g, 18 mmol) in ammonium hydroxide (25%, 100 mL) was stirred at room temperature for overnight. The solid was collected by filtration, washed with water (50 mL) and dried under vacuum to give the title compound (4.0 g, 84%). LC-MS $(M+H)^+$=262.9, 264.9.

Step 13: tert-butyl (33-bro no-5-carbamoyl-2-nitrophenoxy)propyl)(methyl)carbamate

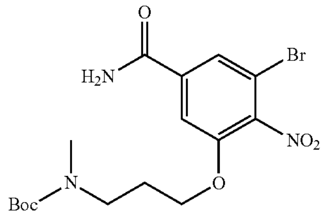 [SMILES: CN(CCCOc1cc(C(N)=O)cc(Br)c1[N+](=O)[O-])C(=O)OC(C)(C)C]

To a solution of tert-butyl (3-hydroxypropyl)methyl)carbamate (7.0 g, 37 mmol) in THF (150 mL) was added NaH (60%, 2.8 g, 70 mmol) in portions. The mixture was stirred at room temperature for 30 min. To the mixture was added 3-bromo-5-fluoro-4-nitrobenzamide (8.0 g, 30.4 mmol). The mixture was stirred at 60° C. for 1 h. The mixture was cooled to room temperature then diluted with water (100 mL), extracted with EtOAc (100 mL×3). The combined organic layer was washed with brine (100 mL), dried over $Na_2SO_4$, filtered and concentrated. The residue was purified by silica gel column chromatography (PE/EtOAc=1/1) to give the title compound (12 g, 92%). LC-MS $(M+H)^+$=432.1.

Step 14: tert-butyl (3-(5-carbamoyl-3-(2-chloropyrimidin-5-yl)-2-nitrophenoxy)propyl)(methyl)carbamate

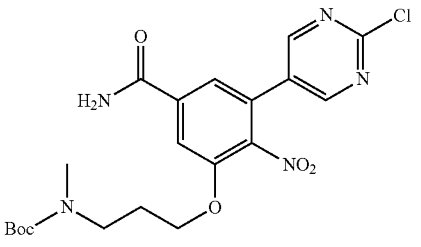 [SMILES: CN(CCCOc1cc(C(N)=O)cc(-c2cnc(Cl)nc2)c1[N+](=O)[O-])C(=O)OC(C)(C)C]

To a mixture of tert-butyl (3-(3-bromo-5-carbamoyl-2-nitrophenoxy)propyl)(methyl) carbamate (12 g, 27.8 mmol) and (2-chloropyrimidin-5-yl)boronic acid (4.8 g, 30.3 mmol) in dioxane (200 mL) and water (40 mL) was added $K_2CO_3$ (7.7 g, 55.7 mmol) and Pd(dppf)$Cl_2$ (700 mg, 0.96 mmol). The mixture was stirred at 80° C. for 2 h under $N_2$. The mixture was cooled to room temperature and partitioned between EtOAc (300 mL) and water (200 mL). The organic layer was separated, washed with brine (100 mL), dried over $Na_2SO_4$, filtered and concentrated. The residue was purified by silica gel column chromatography (PE/EtOAc=1/1) to give the title compound (4.5 g, 34%). LC-MS $(M+H)^+$=466.1.

Step 15: tert-butyl (3-(5-carbamoyl-3-(2-(1-ethyl-3-methyl-1H-pyrazol-5-yl)pyrimidin-5-yl)-2-nitrophenoxy)propyl)(methyl)carbamate

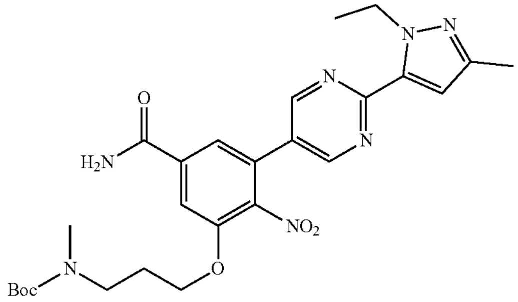 [SMILES: CCn1nc(C)cc1-c1ncc(-c2cc(C(N)=O)cc(OCCCN(C)C(=O)OC(C)(C)C)c2[N+](=O)[O-])cn1]

To a mixture of tert-butyl (3-(5-carbamoyl-3-(2-chloropyrimidin-5-yl)-2-nitrophenoxy)propyl)(methyl)carbamate (4.5 g, 9.7 mmol) and (1-ethyl-3-methyl-1H-pyrazol-5-yl) boronic acid (1.5 g, 9.7 mmol) in dioxane (50 mL) and water (10 mL) was added $K_2CO_3$ (4.0 g, 29 mmol) and Pd(dppf) $Cl_2$ (350 mg, 0.5 mmol). The mixture was stirred at 90° C. for 2 h under $N_2$. The mixture was cooled to room temperature, diluted with water (30 mL) then extracted with EtOAc (30 mL×3). The combined organic layer was washed with brine (30 mL), dried over $Na_2SO_4$, filtered and concentrated. The residue was purified by silica gel column chromatography (EtOAc) to give the title compound (4.5 g, 86%). LC-MS $(M+H)^+$=540.2.

Step 16: tert-butyl (3-((6-carbamoyl-2-(1-ethyl-3-methyl-1H-pyrazol-5-yl)-9H-pyrimido[4,5-b]indol-8-yl)oxy)propyl)(methyl)carbamate

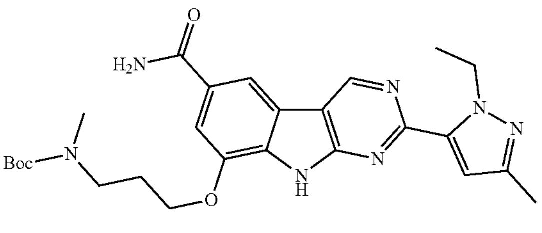 [SMILES: CCn1nc(C)cc1-c1ncc2c(n1)[nH]c1c(OCCCN(C)C(=O)OC(C)(C)C)cc(C(N)=O)cc12]

To a mixture of tert-butyl (3-(5-carbamoyl-3-(2-(1-ethyl-3-methyl-1H-pyrazol-5-yl)pyrimidin-5-yl)-2-nitrophenoxy) propyl)methyl)carbamate (4.5 g, 8.3 mmol) in 1,2-dichlorobenzene (40 mL) was added 1,2-bis (diphenylphosphaneyl)ethane (6.3 g, 16 mmol). The mixture was stirred at 160° C. for 8 h under $N_2$. The mixture was cooled to room temperature and poured into petroleum ether (250 mL), The solid was collected by filtration and purified by silica gel column chromatography (DCM/MeOH=15/1) to give the title compound (700 mg, 16%). LC-MS $(M+H)^+$=508.3.

Step 17: tert-butyl (E)-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)(methyl) carbamate

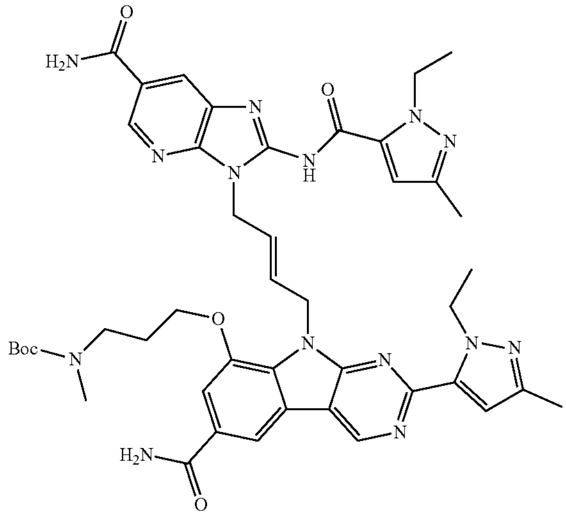 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN(C)C(=O)OC(C)(C)C)c21]

A mixture of tert-butyl (3-((6-carbamoyl-2-(1-ethyl-3-methyl-1H-pyrazol-5-yl)-9H-pyrimido[4,5-b]indol-8-yl) oxy)propyl)methyl)carbamate (11 mg, 0.02 mmol), (E)-3-(4-bromobut-2-en-1-yl)-2-(1-ethyl-3-methyl-1H-pyrazole-5-carboxamido)-3H-imidazo[4,5-b]pyridine-6-carboxamide (12 mg, 0.024 mmol) and $K_2CO_3$ (6 mg, 0.04 mmol) in N,N-dimethylformamide (0.5 mL) was stirred at 70° C. for 2 h. The solvent was evaporated and the residue was purified by prep-TLC (DCM/MeOH=10/1, contains 0.1% ammonia water) to give Example 1-AA (6 mg, 34%). $^1$H NMR (400 MHz, $CD_3OD$) δ 9.32 (s, 1H), 8.67 (s, 1H), 8.32 (s, 1H), 8.13 (s, 1H), 7.58 (s, 1H), 6.84 (s, 1H), 6.36 (s, 1H), 6.06 (s, 1H), 5.75 (s, 1H), 5.41 (s, 2H), 4.81 (s, 2H), 4.70 (s, 2H), 4.47 (s, 2H), 4.08 (s, 2H), 2.79 (s, 3H), 2.27 (s, 3H), 2.09 (s, 3H), 1.92 (s, 2H), 1.40 (s, 9H), 1.27 (d, J=14.4 Hz, 6H). LC-MS $(M+H)^+$=873.4.

Example 1-AB (E)-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-8-(3-(methylamino)propoxy)-9H-pyrimido[4,5-b]indole-6-carboxamide

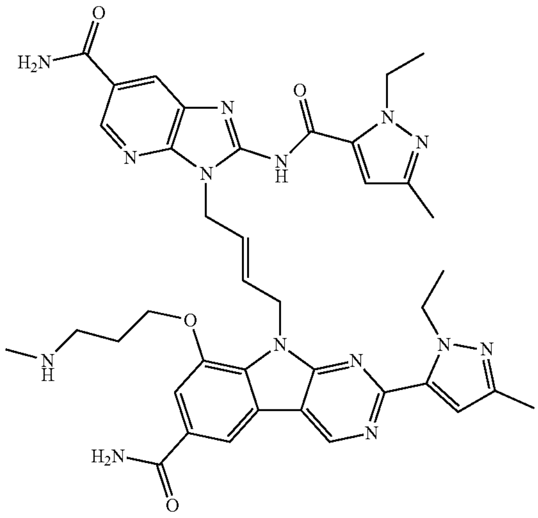

To a solution of tert-butyl (E)-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl(methyl)carbamate (6 mg, 0.007 mmol) in dichloromethane (1 mL) was added a HCl solution in 1,4-dioxane (4 M, 0.5 mL) and the mixture was stirred for 2 h. The mixture was concentrated and the residue was purified by prep-HPLC to give Example 1-AB (1.0 mg, 18%). $^1$H NMR (400 MHz, $CD_3OD$) δ 9.32 (s, 1H), 8.57 (s, 1H), 8.31 (s, 1H), 8.11 (s, 1H), 7.52 (s, 1H), 6.84 (s, 1H), 6.36 (s, 1H), 6.01-5.89 (m, 1H), 5.81-5.72 (m, 1H), 5.40-5.25 (m, 2H), 4.83-4.69 (m, 4H), 4.52-4.42 (m, 2H), 4.10-4.01 (m, 2H), 2.89-2.79 (m, 2H), 2.58 (s, 3H), 2.27 (s, 3H), 2.12 (s, 3H), 2.02-1.89 (m, 2H), 1.46-1.36 (m, 3H), 1.31-1.20 (m, 3H). LC-MS $(M+H)^+$=773.7.

Example 2-AA tert-butyl (E)-4-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)piperazine-1-carboxylate

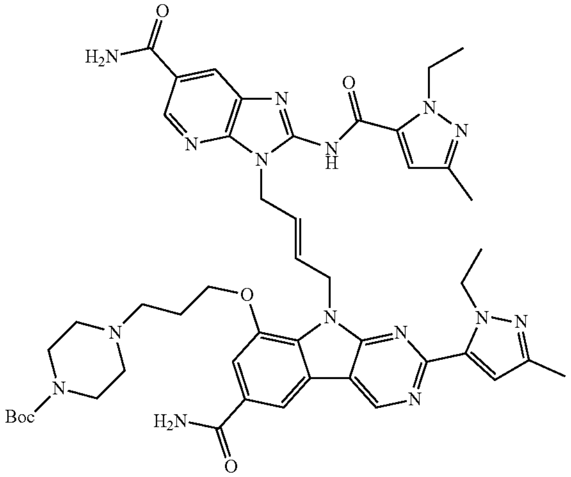 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN3CCN(C(=O)OC(C)(C)C)CC3)c21]

Step 1: tert-butyl 4-(3-(3-bromo-5-carbamoyl-2-nitrophenoxy)propyl)piperazine-1-carboxylate

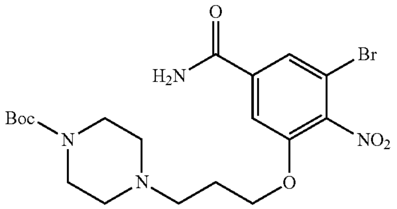 [SMILES: CC(C)(C)OC(=O)N1CCN(CCCOc2cc(C(N)=O)cc(Br)c2[N+](=O)[O-])CC1]

The title compound (10.0 g, 60%) was prepared in a manner similar to that in Example 1-AA step 13 from tert-butyl 4-(3-hydroxypropyl)piperazine-1-carboxylate and 3-bromo-5-fluoro-4-nitrobenzamide. LC-MS $(M+H)^+$ =487.1.

Step 2: tert-butyl 4-(3-(5-carbamoyl-3-(2-chloropyrimidin-5-yl)-2-nitrophenoxy)propyl) piperazine-1-carboxylate

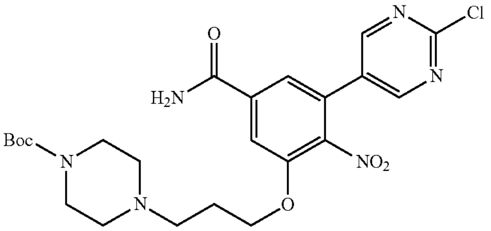 [SMILES: CC(C)(C)OC(=O)N1CCN(CCCOc2cc(C(N)=O)cc(-c3cnc(Cl)nc3)c2[N+](=O)[O-])CC1]

The title compound (3.0 g, 28%) was prepared in a manner similar to that in Example 1-AA step 14 from tert-butyl 4-(3-(3-bromo-5-carbamoyl-2-nitrophenoxy)propyl)piperazine-1-carboxylate and (2-chloropyrimidin-5-yl) boronic acid. LC-MS $(M+H)^+$=521.2.

Step 3: tert-butyl 4-(3-(5-carbamoyl-3-(2-(1-ethyl-3-methyl-1H-pyrazol-5-yl)pyrimidin-5-yl)-2-nitrophenoxy)propyl)piperazine-1-carboxylate

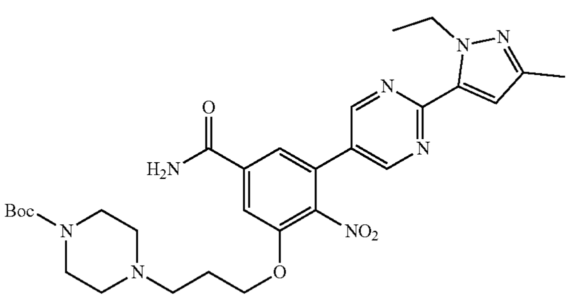 [SMILES: CCn1nc(C)cc1-c1ncc(-c2cc(C(N)=O)cc(OCCCN3CCN(C(=O)OC(C)(C)C)CC3)c2[N+](=O)[O-])cn1]

The title compound (2.3 g, 65%) was prepared in a manner similar to that in Example 1-AA step 15 from tert-butyl 4-(3-(5-carbamoyl-3-(2-chloropyrimidin-5-yl)-2-nitrophenoxy)propyl) piperazine-1-carboxylate and (1-ethyl-3-methyl-1H-pyrazol-5-yl)boronic. LC-MS $(M+H)^+$=595.3.

Step 4: tert-butyl 4-(3-((6-carbamoyl-2-(1-ethyl-3-methyl-1H-pyrazol-5-yl)-9H-pyrimido[4,5-b]indol-8-yl)oxy)propyl)piperazine-1-carboxylate

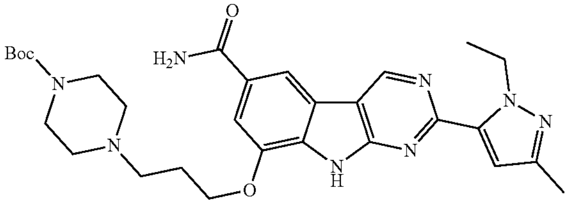 [SMILES: CCn1nc(C)cc1-c1ncc2c(n1)[nH]c1c(OCCCN3CCN(C(=O)OC(C)(C)C)CC3)cc(C(N)=O)cc12]

The title compound (500 mg, 23%) was prepared in a manner similar to that in Example 1-AA step 16 from tert-butyl 4-(3-(5-carbamoyl-3-(2-(1-ethyl-3-methyl-1H-pyrazol-5-yl)pyrimidin-5-yl)-2-nitrophenoxy)propyl)piperazine-1-carboxylate and 1,2-bis(diphenylphosphaneyl) ethane. LC-MS $(M+H)^+$=563.3.

Step 5: tert-butyl (E)-4-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)piperazine-1-carboxylate

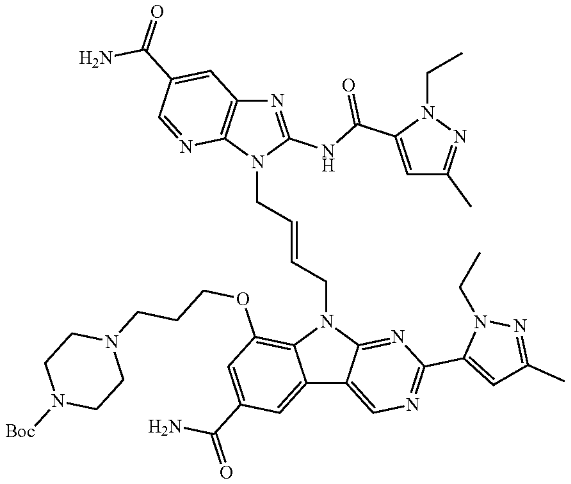 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN3CCN(C(=O)OC(C)(C)C)CC3)c21]

Example 2-AA (280 mg, 34%) was prepared in a manner similar to that in Example 1-AA step 17 from tert-butyl 4-(3-((6-carbamoyl-2-(1-ethyl-3-methyl-1H-pyrazol-5-yl)-9H-pyrimido[4,5-b]indol-8-yl)oxy)propyl)piperazine-1-carboxylate and (E)-3-(4-bromobut-2-en-1-yl)-2-(1-ethyl-3-methyl-1H-pyrazole-5-carboxamido)-3H-imidazo[4,5-b]pyridine-6-carboxamide. $^1$H NMR (400 MHz, $CD_3OD$) δ 9.21 (s, 1H), 8.65 (s, 1H), 8.23 (s, 1H), 8.10 (s, 1H), 7.51 (s, 1H), 6.75 (s, 1H), 6.31 (s, 1H), 6.04 (d, J=14.5 Hz, 1H), 5.68 (d, J=15.0 Hz, 1H), 5.31 (s, 2H), 4.75 (s, 2H), 4.66-4.64 (m, 2H), 4.46-4.44 (m, 2H), 4.09 (s, 2H), 3.49 (s, 4H), 2.69-2.61 (m, 6H), 2.22 (s, 3H), 2.06 (s, 3H), 1.97 (s, 2H), 1.47 (s, 9H), 1.35 (s, 3H), 1.24 (s, 3H). LC-MS $(M+H)^+$=928.5.

Example 2-AB-HCl (E)-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-8-(3-(piperazin-1-yl)propoxy)-9H-pyrimido[4,5-b]indole-6-carboxamide hydrochloride

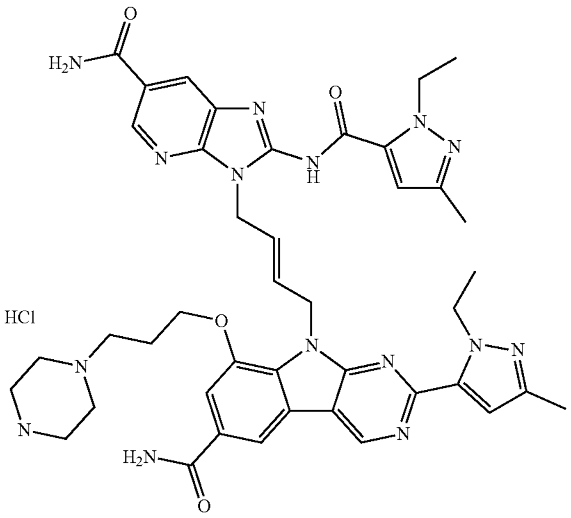 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN3CCNCC3)c21 ; Cl]

Example 2-AB-HCl (200 mg, 77%) was prepared in a manner similar to that in Example 1-AB from tert-butyl (E)-4-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)piperazine-1-carboxylate. $^1$H NMR (400 MHz, $CD_3OD$) δ 9.59 (s, 1H), 8.76 (s, 1H), 8.45 (s, 1H), 8.21 (s, 1H), 7.74 (s, 1H), 7.06 (s, 1H), 6.64 (s, 1H), 6.21 (d, J=15.1 Hz, 1H), 5.69 (d, J=15.1 Hz, 1H), 5.52-5.45 (m, 2H), 4.90 (2H under water peak), 4.72-4.62 (m, 4H), 4.36-4.30 (m, 2H), 4.00-3.49 (m, 10H), 2.45-2.34 (m, 5H), 2.27 (s, 3H), 1.48-1.35 (m, 6H). LC-MS $(M+H)^+$=828.5.

Example 1-AC (E)-8-(3-(2-(aminooxy-N-methylacetamido)propoxy)-9-(4-(6-carbamoyl-2-(1-ethyl-3-methyl-1H-pyrazole-5-carboxamido)-3H-imidazo[4,5-b]pyridin-3-yl)but-2-en-1-yl-2-(1-ethyl-3-methyl-1H-pyrazol-5-yl-9H-pyrimido[4,5-b]indole-6-carboxamide

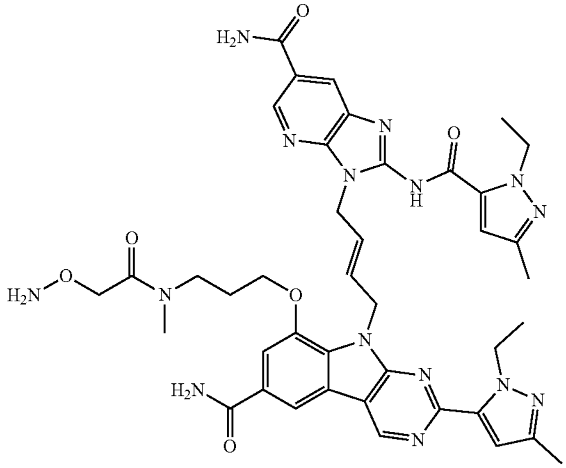 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN(C)C(=O)CON)c21]

Step 1: tert-butyl (E)-(2-((3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)(methyl)amino)-2-oxoethoxy)carbamate

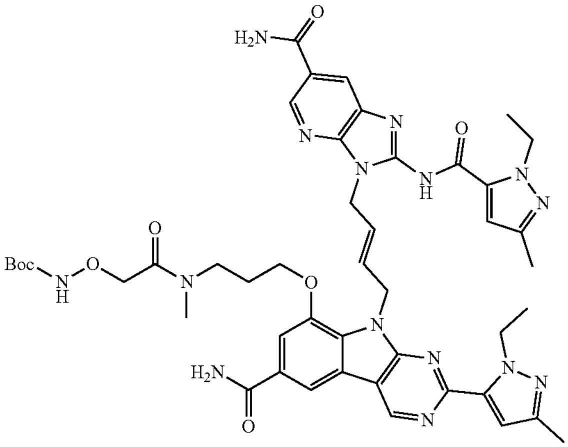 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN(C)C(=O)CONC(=O)OC(C)(C)C)c21]

To a mixture of (E)-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-8-(3-(methylamino)propoxy)-9H-pyrimido[4,5-b]indole-6-carboxamide (90 mg, 0.116 mmol), 2-(((tert-butoxycarbonyl)amino)oxy)acetic acid (33 mg, 0.175 mmol) and DIEA (30 mg, 0.233 mmol) in DMF (5 mL) was added HATU (66 mg, 0.175 mmol). The mixture was stirred at room temperature for 5 h. The mixture was diluted with water, extracted with DCM/IPA (3/1, 60 mL×2), dried over $Na_2SO_4$, filtered and concentrated. The residue was triturated with EtOAc to give the title compound (60 mg, 55%). LC-MS $(M+H)^+$=946.

Step 2: (E)-8-(3-(2-(aminooxy)-N-methylacetamido)propoxy)-9-(4-(6-carbamoyl-2-(i-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl-9H-pyrimido[4,5-b]indole-6-carboxamide

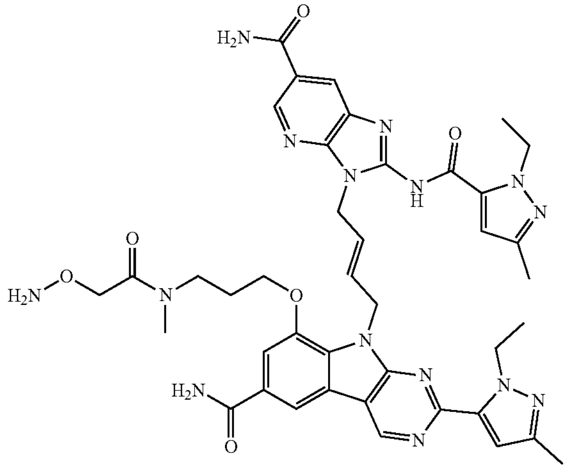 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN(C)C(=O)CON)c21]

To a mixture of tert-butyl (E)-(2-((3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl(methyl)amino)-2-oxoethoxy)carbamate (60 mg, 0.0635 mmol) in DCM/MeOH (8 mL/4 mL) was added a solution of 4 M HCl in dioxane (2.0 mL). The mixture was stirred at room temperature for overnight. The mixture was concentrated to dryness and the residue was purified by prep-HPLC to give Example 1-AC (18 mg, 33%). $^1$HNMR (400 MHz, $CD_3OD$) δ 9.26 (s, 1H), 8.65 (s, 1H), 8.30-8.23 (m, 1H), 8.11 (s, 1H), 7.55-7.47 (m, 1H), 6.83-6.76 (m, 1H), 6.40-6.31 (m, 1H), 6.06 (d, J=15.6 Hz, 1H), 5.78-5.55 (m, 1H), 5.41-5.35 (m, 2H), 4.82-4.58 (m, 4H), 4.52-4.39 (m, 2H), 4.36-4.30 (m, 2H), 4.16-3.96 (m, 2H), 3.45-3.32 (m, 2H), 2.88 (s, 3H), 2.25 (s, 3H), 2.15-1.84 (m, 5H), 1.39 (t, J=6.8 Hz, 3H), 1.23 (t, J=6.8 Hz, 3H). LC-MS $(M+H)^+$=846.5.

Example 2-AC (E)-8-(3-(4-(2-(aminooxy)acetyl)piperazin-1-yl)propoxy)-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indole-6-carboxamide

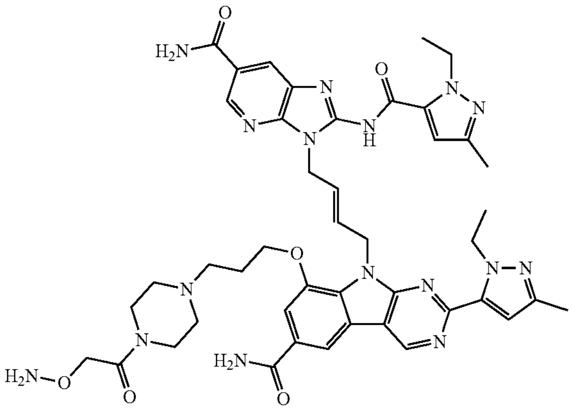 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN3CCN(C(=O)CON)CC3)c21]

Step 1: tert-butyl (E)-(2-(4-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)piperazin-1-yl)-2-oxoethoxy)carbamate

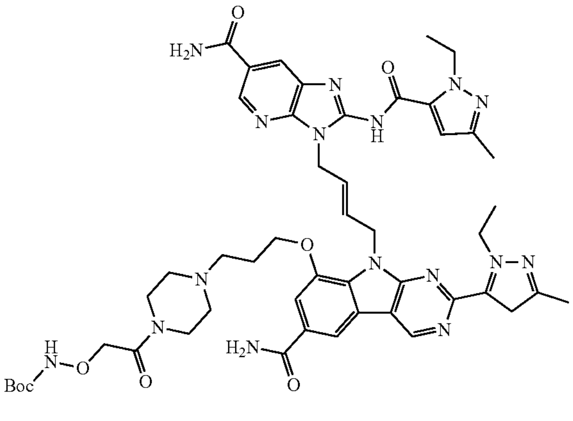

To a mixture of (E)-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-8-(3-(piperazin-1-yl)propoxy)-9H-pyrimido[4,5-b]indole-6-carboxamide hydrochloride (80 mg, 0.1 mmol), 2-(((tert-butoxycarbonyl)amino)oxy)acetic acid (29 mg, 0.15 mmol) and DIEA (52 mg, 0.4 mmol) in DMF (5 mL) was added HATU (57 mg, 0.15 mmol). The mixture was stirred at room temperature for 15 h. The mixture was diluted with water, extracted with DCM/IPA (3/1, 60 mL×2), dried over $Na_2SO_4$, filtered and concentrated. The residue was triturated with EA/PE to give the title compound (90 mg, 90%). LC-MS $(M+H)^+$=1001.

Step 2: (E)-8-(3-(4-(2-(aminooxy)acetyl)piperazin-1-yl)propoxy)-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indole-6-carboxamide

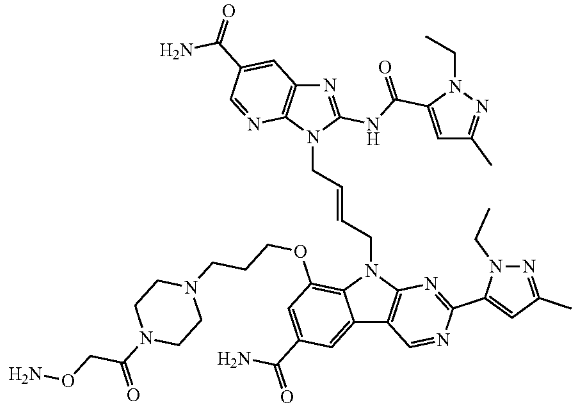 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN3CCN(C(=O)CON)CC3)c21]

To a mixture of tert-butyl (E)-(2-(4-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)piperazin-1-yl)-2-oxoethoxy) carbamate (90 mg, 0.09 mmol) in DCM/MeOH (8 mL/4 mL) was added a solution of 4 M HCl in dioxane (2.0 mL). The mixture was stirred at room temperature for overnight, concentrated to dryness and the residue was purified by prep-HPLC to give Example 2-AC (20 mg, 25%). S $^1$H NMR (400 MHz, $CD_3OD$) δ 9.31 (s, 1H), 8.68 (s, 1H), 8.29 (s, 1H), 8.14 (s, 1H), 7.55 (s, 1H), 6.83 (s, 1H), 6.34 (s, 1H), 6.10-5.95 (m, 1H), 5.80-5.65 (m, 1H), 5.40-5.32 (m, 2H), 4.82-4.65 (m, 4H), 4.62-4.35 (m, 4H), 4.16-4.04 (m, 2H), 3.65-3.52 (m, 2H), 3.48-3.37 (m, 2H), 2.55-2.32 (m, 6H), 2.26 (s, 3H), 2.08 (s, 3H), 1.95-1.80 (m, 2H), 1.45-1.20 (m, 6H). LC-MS $(M+H)^+$=901.5.

Example 3-AA tert-butyl (E)-(4-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)butyl)(methyl)carbamate

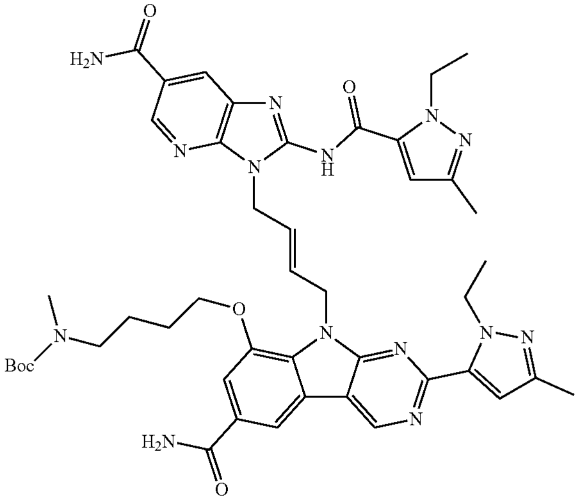 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCCN(C)C(=O)OC(C)(C)C)c21]

Step 1: tert-butyl (4-(3-bromo-5-carbamoyl-2-nitrophenoxy)butyl)(methyl)carbamate

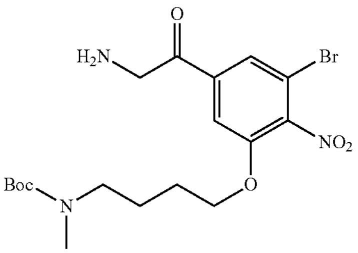 [SMILES: CN(CCCCOc1cc(C(=O)CN)cc(Br)c1[N+](=O)[O-])C(=O)OC(C)(C)C]

The title compound (4.56 g, 68%) was prepared in a manner similar to that in Example 1-AA step 13 from tert-butyl N-(4-hydroxybutyl)-N-methylcarbamate and 3-bromo-5-fluoro-4-nitrobenzamide. LC-MS $(M-Boc+H)^+$=348.0.

Step 2: tert-butyl (4-(5-carbamoyl-3-(2-chloropyrimidin-5-yl)-2-nitrophenoxy)butyl)(methyl)carbamate

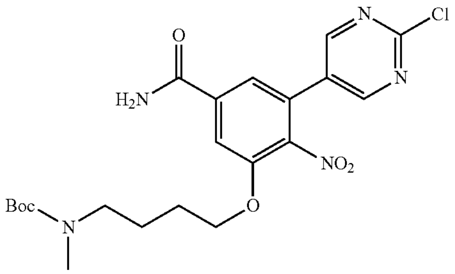 [SMILES: CN(CCCCOc1cc(C(N)=O)cc(-c2cnc(Cl)nc2)c1[N+](=O)[O-])C(=O)OC(C)(C)C]

The title compound (388 mg, 28%) was prepared in a manner similar to that in Example 1-AA step 14 from tert-butyl 4-(3-bromo-5-carbamoyl-2-nitrophenoxy)butyl (methyl)carbamate and (2-chloropyrimidin-5-yl)boronic acid. LC-MS $(M-Boc+H)^+=380.1$.

Step 3: tert-butyl (4-(5-carbamoyl-3-(2-(1-ethyl-3-methyl-1H-pyrazol-5-yl)pyrimidin-5-yl)-2-nitrophenoxy)butyl)(methyl)carbamate

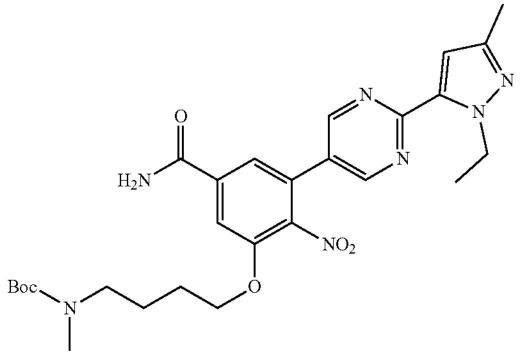 [SMILES: CCn1nc(C)cc1-c1ncc(-c2cc(C(N)=O)cc(OCCCCN(C)C(=O)OC(C)(C)C)c2[N+](=O)[O-])cn1]

The title compound (194 mg, 43%) was prepared in a manner similar to that in Example 1-AA step 15 from tert-butyl 4-(5-carbamoyl-3-(2-chloropyrimidin-5-yl)-2-nitrophenoxy)butyl(methyl)carbamate and (1-ethyl-3-methyl-1H-pyrazol-5-yl)boronic acid. LC-MS $(M+H)^+=554.4$.

Step 4: tert-butyl (4-(6-carbamoyl-2-(1-ethyl-3-methyl-1H-pyrazol-5-yl)-9H-pyrimido[4,5-b]indol-8-yloxy)butyl)(methyl)carbamate

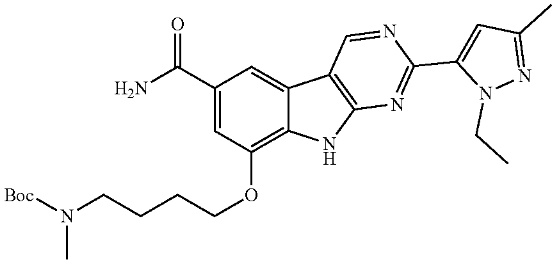 [SMILES: CCn1nc(C)cc1-c1ncc2c(n1)[nH]c1c(OCCCCN(C)C(=O)OC(C)(C)C)cc(C(N)=O)cc12]

The title compound (100 mg, 6%) was prepared in a manner similar to that in Example 1-AA step 16 from tert-butyl (4-(5-carbamoyl-3-(2-(1-ethyl-3-methyl-1H-pyrazol-5-yl)pyrimidin-5-yl)-2-nitrophenoxy)butyl)methyl)carbamate and 1,2-bis(diphenylphosphaneyl)ethane. $^1H$ NMR (400 MHz, DMSO-$d_6$) 12.69 (s, 1H), 9.51 (s, 1H), 8.42 (s, 1H), 8.04 (s, 1H), 7.64 (s, 1H), 7.35 (s, 1H), 6.80 (s, 1H), 4.85-4.75 (m, 2H), 4.31-4.24 (m, 2H), 3.32-3.25 (m, 2H), 2.80 (s, 3H), 2.23 (s, 3H), 1.88-1.71 (m, 4H), 1.43-1.31 (m, 12H). LC-MS $(M+H)^+=522.4$.

Step 5: tert-butyl (E)-(4-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)butyl)(methyl) carbamate

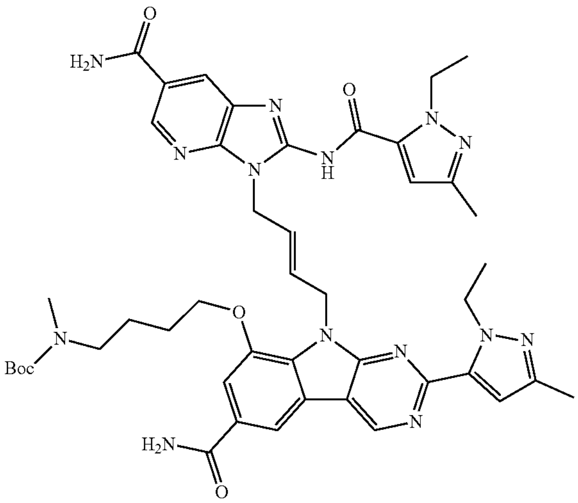 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCCN(C)C(=O)OC(C)(C)C)c21]

Example 3-AA (120 mg, 68%) was prepared in a manner similar to that in Example 1-AA step 17 from tert-butyl (4-(6-carbamoyl-2-(1-ethyl-3-methyl-1H-pyrazol-5-yl)-9H-pyrimido[4,5-b]indol-8-yloxy)butyl)(methyl)carbamate and (E)-3-(4-bromobut-2-en-1-yl)-2-(1-ethyl-3-methyl-1H-pyrazole-5-carboxamido)-3H-imidazo[4,5-b]pyridine-6-carboxamide. $^1H$ NMR (400 MHz, DMSO-d6) δ 12.84 (s, 1H), 9.46 (s, 1H), 8.66 (d, J=1.9 Hz, 1H), 8.41 (d, J=1.3 Hz, 1H), 8.13 (s, 1H), 8.09 (d, J=1.8 Hz, 1H), 8.03 (s, 1H), 7.59 (s, 1H), 7.53 (s, 1H), 7.38 (s, 1H), 6.77 (d, J=0.4 Hz, 1H), 6.40 (s, 1H), 5.99-5.93 (m, 1H), 5.74 (s, 1H), 5.25 (s, 2H), 4.70 (d, J=5.5 Hz, 2H), 4.60 (q, J=7.1 Hz, 2H), 4.45 (q, J=7.3 Hz, 2H), 4.09 (t, J=6.1 Hz, 2H), 3.07 (t, J=6.6 Hz, 2H), 2.69 (s, 3H), 2.21-2.14 (m, 3H), 2.05 (s, 3H), 1.60-1.50 (m, 4H), 1.32-1.29 (m, 9H), 1.25 (t, J=7.1 Hz, 4H), 1.20 (t, J=7.1 Hz, 3H). LC-MS $(M+H)^+=887.6$.

Example 3-AB-HCl (E)-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-8-(4-(methylamino)butoxy)-9H-pyrimido[4,5-b]indole-6-carboxamide hydrochloride

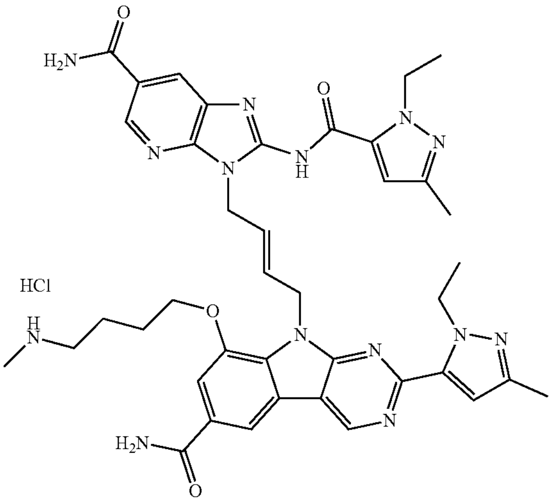

Example 3-AB-HCl (80 mg, 78%) was prepared in a manner similar to that in Example 1-AB from tert-butyl (E)-(4-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)butyl)methyl)carbamate. $^{1}H$ NMR (400 MHz, DMSO-d6) δ 9.48 (s, 1H), 8.71 (s, 1H), 8.54 (s, 2H), 8.45 (s, 1H), 8.21-8.01 (m, 3H), 7.64-7.56 (m, 2H), 7.42 (s, 1H), 6.79 (s, 1H), 6.40 (s, 1H), 5.04-5.94 (m, 1H), 5.75-5.65 (m, 1H), 5.31-5.22 (m, 2H), 4.77-4.70 (m, 2H), 4.65-4.55 (m, 2H), 4.49-4.39 (m, 2H), 4.18-4.08 (m, 2H), 2.89-2.79 (m, 2H), 2.19 (s, 3H), 2.10-1.98 (m, 5H), 1.76-1.67 (m, 5H), 1.28-1.16 (m, 6H). LC-MS $(M+H)^{+}$=787.5.

Example 4-AA tert-butyl (E)-3-(2-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)ethyl)azetidine-1-carboxylate

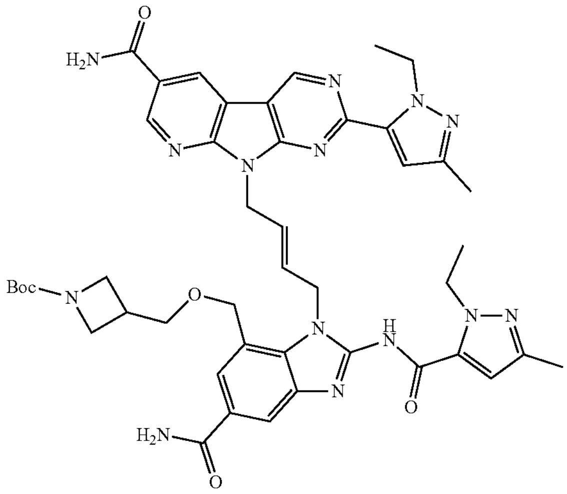 [SMILES: CCn1nc(C)cc1C(=O)Nc1nc2cc(C(N)=O)cc(COCC3CN(C(=O)OC(C)(C)C)C3)c2n1C/C=C/Cn1c2ncc(C(N)=O)cc2c2cnc(-c3cc(C)nn3CC)nc21]

Step 1: tert-butyl 3-(2-(3-bromo-5-carbamoyl-2-nitrophenoxy)ethyl)azetidine-1-carboxylate

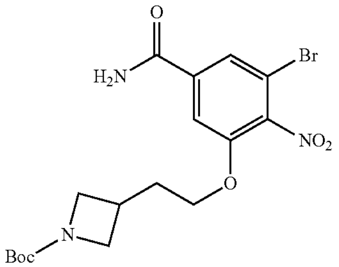 [SMILES: CC(C)(C)OC(=O)N1CC(CCOc2cc(C(N)=O)cc(Br)c2[N+](=O)[O-])C1]

The title compound (6.88 g, 91%) was prepared in a manner similar to that in Example 1-AA step 13 from 3-bromo-5-fluoro-4-nitrobenzamide and tert-butyl 3-(2-hydroxyethyl)azetidine-1-carboxylate. LC-MS $(M-Boc+H)^{+}$=343.9.

Step 2: tert-butyl 3-(2-(5-carbamoyl-3-(2-chloropyrimidin-5-yl)-2-nitrophenoxy)ethyl)azetidine-1-carboxylate

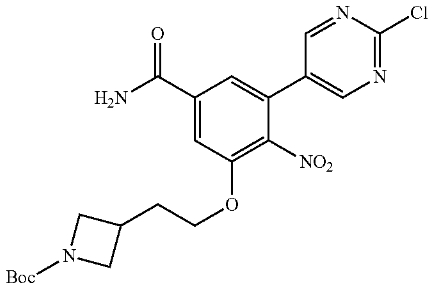 [SMILES: CC(C)(C)OC(=O)N1CC(CCOc2cc(C(N)=O)cc(-c3cnc(Cl)nc3)c2[N+](=O)[O-])C1]

The title compound (556 mg, 28%) was prepared in a manner similar to that in Example 1-AA step 14 from tert-butyl 3-(2-(3-bromo-5-carbamoyl-2-nitrophenoxy)ethyl)azetidine-1-carboxylate and 2-chloropyrimidin-5-ylboronic acid. LC-MS (M−Boc+H)$^+$=378.1.

Step 3: tert-butyl 3-(2-(5-carbamoyl-3-(2-(1-ethyl-3-methyl-1H-pyrazol-5-yl)pyrimidin-5-yl)-2-nitrophenoxy)ethyl)azetidine-1-carboxylate

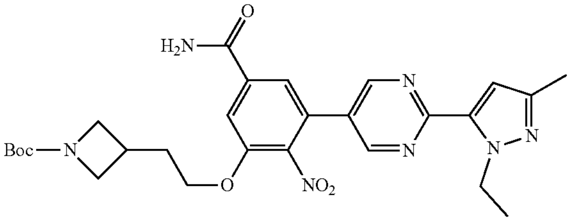 [SMILES: CCn1nc(C)cc1-c1ncc(-c2cc(C(N)=O)cc(OCCC3CN(C(=O)OC(C)(C)C)C3)c2[N+](=O)[O-])cn1]

The title compound (230 mg, 36%) was prepared in a manner similar to that in Example 1-AA step 15 from tert-butyl 3-(2-(5-carbamoyl-3-(2-chloropyrimidin-5-yl)-2-nitrophenoxy)ethyl)azetidine-1-carboxylate and 1-ethyl-3-methyl-1H-pyrazol-5-yl boronic acid. LC-MS (M+H)$^+$ =552.3.

Step 4: tert-butyl 3-(2-((6-carbamoyl-2-(1-ethyl-3-methyl-1H-pyrazol-5-yl)-9H-pyrimido[4,5-b]indol-8-yl)oxy)ethyl)azetidine-1-carboxylate

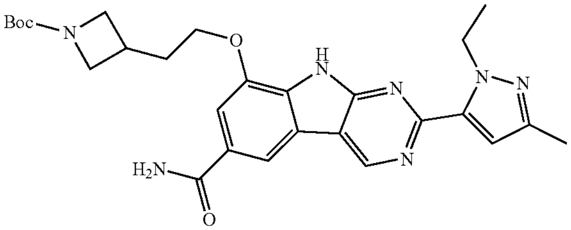 [SMILES: CCn1nc(C)cc1-c1ncc2c(n1)[nH]c1c(OCCC3CN(C(=O)OC(C)(C)C)C3)cc(C(N)=O)cc12]

The title compound (101 mg, 6%) was prepared in a manner similar to that in Example 1-AA step 16 from tert-butyl 3-(2-(5-carbamoyl-3-(2-(1-ethyl-3-methyl-1H-pyrazol-5-yl)pyrimidin-5-yl)-2-nitrophenoxy)ethyl)azetidine-1-carboxylate. $^1$H NMR (300 MHz, DMSO-$d_6$) δ 12.67 (s, 1H), 9.52 (s, 1H), 8.43 (s, 1H), 8.04 (s, 1H), 7.64 (s, 1H), 7.36 (s, 1H), 6.82 (s, 1H), 4.88-4.75 (m, 2H), 4.31-4.21 (m, 2H), 4.04-3.93 (m, 2H), 3.72-3.61 (m, 2H), 3.00-2.85 (m, 1H), 2.24 (s, 3H), 2.20-2.05 (m, 2H), 1.44-1.33 (m, 12H). LC-MS (M+H)$^+$=520.3.

Step 5: tert-butyl (E)-3-(2-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)ethyl)azetidine-1-carboxylate

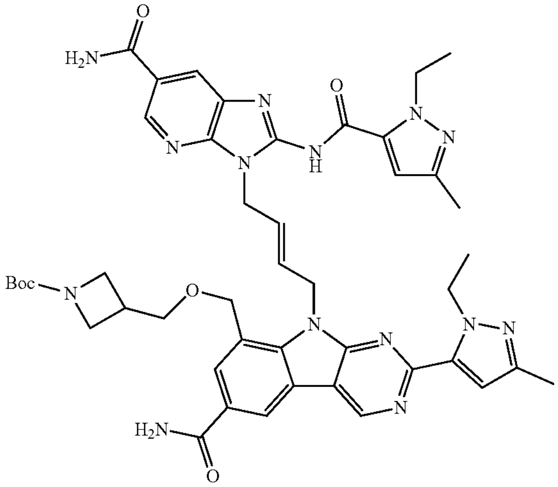 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(COCC3CN(C(=O)OC(C)(C)C)C3)c21]

Example 4-AA (100 mg, 56%) was prepared in a manner similar to that in Example 1-AA step 17 from tert-butyl 3-(2-((6-carbamoyl-2-(1-ethyl-3-methyl-1H-pyrazol-5-yl)-9H-pyrimido[4,5-b]indol-8-yl)oxy)ethyl)azetidine-1-carboxylate and (E)-3-(4-bromobut-2-en-1-yl)-2-(1-ethyl-3-methyl-1H-pyrazole-5-carboxamido)-3H-imidazo[4,5-b]pyridine-6-carboxamide. $^1$H NMR (400 MHz, DMSO-d6) δ 12.84 (s, 1H), 9.47 (s, 1H), 8.66 (d, J=1.9 Hz, 1H), 8.41 (d, J=1.3 Hz, 1H), 8.12 (s, 1H), 8.09 (d, J=1.9 Hz, 1H), 8.02 (s, 1H), 7.59 (d, J=1.2 Hz, 1H), 7.53 (s, 1H), 7.39 (s, 1H), 6.77 (d, J=0.5 Hz, 1H), 6.41 (s, 1H), 6.03-5.92 (m, 1H), 5.73-5.68 (m, 1H), 5.24 (d, J=4.7 Hz, 2H), 4.72 (d, J=5.3 Hz, 2H), 4.60 (q, J=6.8 Hz, 2H), 4.51-4.43 (m, 2H), 4.04 (t, J=6.3 Hz, 2H), 3.85 (s, 2H), 3.45 (s, 2H), 2.18 (s, 3H), 2.05 (s, 3H), 1.91-1.89 (m, 2H), 1.34 (s, 9H), 1.27-1.19 (m, 7H). LC-MS (M+H)$^+$=885.6.

Example 4-AB: (E)-8-(2-(azetidin-3-yl)ethoxy)-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indole-6-carboxamide

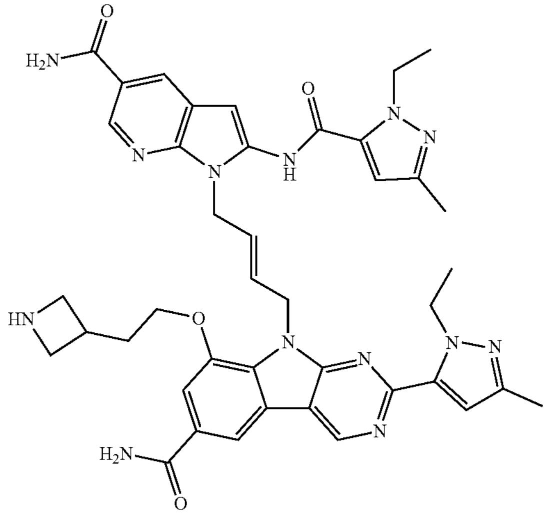 [SMILES: CCn1nc(C)cc1C(=O)Nc1cc2cc(C(N)=O)cnc2n1C/C=C/Cn1c2nc(-c3cc(C)nn3CC)ncc2c2cc(C(N)=O)cc(OCCC3CNC3)c21]

Example 4-AB (40 mg, 46%) was prepared in a manner similar to that in Example 1-AB from tert-butyl (E)-3-(2-((6-carbamoyl-9-(4-(6-carbamoyl-2-(1-ethyl-3-methyl-1H-pyrazole-5-carboxamido)-3H-imidazo[4,5-b]pyridin-3-yl) but-2-en-1-yl)-2-(1-ethyl-3-methyl-1H-pyrazol-5-yl)-9H-pyrimido[4,5-b]indol-8-yl)oxy)ethyl)azetidine-1-carboxylate. $^1$H NMR (400 MHz, DMSO-d6) δ 9.49 (s, 1H), 8.57 (s, 1H), 8.43 (s, 1H), 8.30 (s, 1H), 8.08-8.03 (m, 3H), 7.56 (s, 1H), 7.48-4.35 (m, 2H), 6.84 (s, 1H), 6.35 (s, 1H), 5.90-5.80 (m, 2H), 5.28-5.17 (m, 2H), 4.81-4.63 (m, 4H), 4.50-4.40 (m, 2H), 4.05-3.91 (m, 4H), 3.61-3.50 (m, 2H), 2.81-2.74 (m, 1H), 2.22 (s, 3H), 2.06 (s, 3H), 1.93 (s, 2H), 1.36-1.29 (m, 3H), 1.22-1.15 (m, 3H). LC-MS $(M+H)^+$=785.7.

Example 5-AA: tert-butyl (E)-3-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)azetidine-1-carboxylate

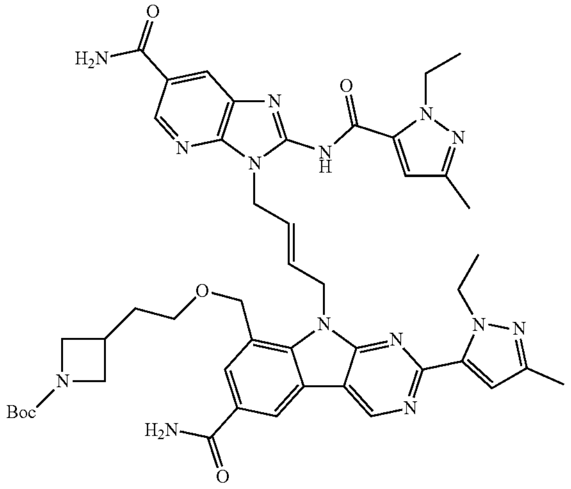 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(COCCC3CN(C(=O)OC(C)(C)C)C3)c21]

Step 1: tert-butyl 3-(3-(3-bromo-5-carbamoyl-2-nitrophenoxy)propyl)azetidine-1-carboxylate

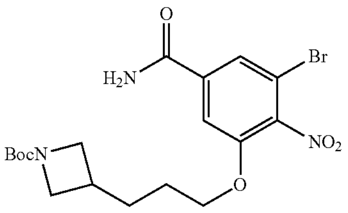 [SMILES: CC(C)(C)OC(=O)N1CC(CCCOc2cc(C(N)=O)cc(Br)c2[N+](=O)[O-])C1]

The title compound (2.82 g, 96%) was prepared in a manner similar to that in Example 1-AA step 13 from 3-bromo-5-fluoro-4-nitrobenzamide and tert-butyl 3-(3-hydroxypropyl)azetidine-1-carboxylate. LC-MS $(M-Boc+H)^+$=358.1.

Step 2: tert-butyl 3-(3-(5-carbamoyl-3-(2-chloropyrimidin-5-yl)-2-nitrophenoxy)propyl)azetidine-1-carboxylate

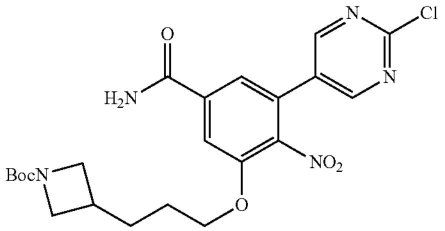 [SMILES: CC(C)(C)OC(=O)N1CC(CCCOc2cc(C(N)=O)cc(-c3cnc(Cl)nc3)c2[N+](=O)[O-])C1]

The title compound (174 mg, 92%) was prepared in a manner similar to that in Example 1-AA step 14 from tert-butyl 3-(3-(3-bromo-5-carbamoyl-2-nitrophenoxy)propyl)azetidine-1-carboxylate and 2-chloropyrimidin-5-ylboronic acid. LC-MS $(M-Boc+H)^+$=392.0.

Step 3: tert-butyl 3-(3-(5-carbamoyl-3-(2-(1-ethyl-3-methyl-1H-pyrazol-5-yl)pyrimidin-5-yl)-2-nitrophenoxy)propyl)azetidine-1-carboxylate

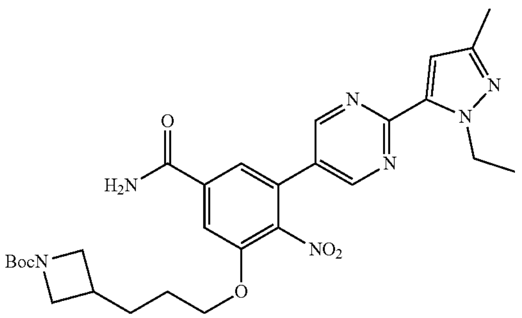 [SMILES: CCn1nc(C)cc1-c1ncc(-c2cc(C(N)=O)cc(OCCCC3CN(C(=O)OC(C)(C)C)C3)c2[N+](=O)[O-])cn1]

The title compound (171 mg, 86%) was prepared in a manner similar to that in Example 1-AA step 15 from tert-butyl 3-(3-(5-carbamoyl-3-(2-chloropyrimidin-5-yl)-2-nitrophenoxy)propyl)azetidine-1-carboxylate and 1-ethyl-3-methyl-1H-pyrazol-5-yl boronic acid. LC-MS $(M+H)^+$=566.3.

Step 4: tert-butyl 3-(3-((6-carbamoyl-2-(1-ethyl-3-methyl-1H-pyrazol-5-yl)-9H-pyrimido[4,5-b]indol-8-yl)oxy)propyl)azetidine-1-carboxylate

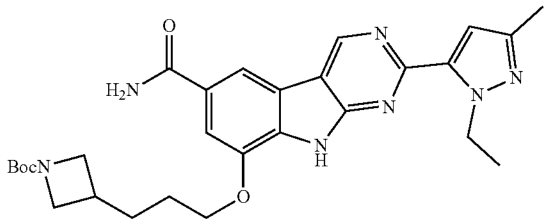 [SMILES: CCn1nc(C)cc1-c1ncc2c(n1)[nH]c1c(OCCCC3CN(C(=O)OC(C)(C)C)C3)cc(C(N)=O)cc12]

The title compound (99 mg, 7%) was prepared in a manner similar to that in Example 1-AA step 16 from tert-butyl 3-(3-(5-carbamoyl-3-(2-(1-ethyl-3-methyl-1H-pyrazol-5-yl)pyrimidin-5-yl)-2-nitrophenoxy)propyl)azetidine-1-carboxylate. $^1$H NMR (400 MHz, DMSO-$d_6$) δ 12.71 (s, 1H), 9.53 (s, 1H), 8.42 (s, 1H), 8.04 (s, 1H), 7.63 (s, 1H), 7.35 (s, 1H), 6.81 (s, 1H), 4.88-4.75 (m, 2H), 4.29-4.19 (m, 2H), 4.01-3.90 (m, 2H), 3.59-3.49 (m, 2H), 2.66-2.56 (m, 1H), 2.24 (s, 3H), 1.88-1.80 (m, 4H), 1.44-1.33 (m, 12H). LC-MS (M+H)$^+$=534.3.

Step 5: tert-butyl (E)-3-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)azetidine-1-carboxylate

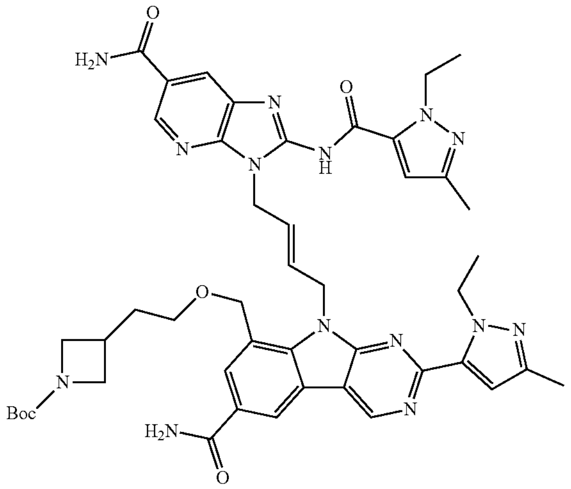 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(COCCC3CN(C(=O)OC(C)(C)C)C3)c21]

Example 5-AA (140 mg, 77%) was prepared in a manner similar to that in Example AA step 17 from tert-butyl 3-(3-((6-carbamoyl-2-(1-ethyl-3-methyl-1H-pyrazol-5-yl)-9H-pyrimido[4,5-b]indol-8-yl)oxy)propyl)azetidine-1-carboxylate and (E)-3-(4-bromobut-2-en-1-yl)-2-(1-ethyl-3-methyl-1H-pyrazole-5-carboxamido)-3H-imidazo[4,5-b]pyridine-6-carboxamide. $^1$H NMR (400 MHz, DMSO-d6) δ 12.84 (s, 1H), 9.46 (s, 1H), 8.66 (s, 1H), 8.40 (s, 1H), 8.13 (s, 1H), 8.09 (s, 1H), 8.03 (s, 1H), 7.58 (s, 1H), 7.54 (s, 1H), 7.38 (s, 1H), 6.77 (s, 1H), 6.40 (s, 1H), 5.93 (s, 1H), 5.70 (s, 1H), 5.25 (s, 2H), 4.70 (s, 2H), 4.61 (s, 2H), 4.45 (s, 2H), 4.03 (s, 2H), 3.82 (s, 2H), 2.31 (s, 2H), 2.18 (s, 3H), 2.05 (s, 3H), 1.55 (s, 4H), 1.32 (s, 9H), 1.28-1.18 (m, 7H). LC-MS (M+H)$^+$=899.7.

Example 5-AB: (E)-8-(3-(azetidin-3-yl)propoxy)-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indole-6-carboxamide

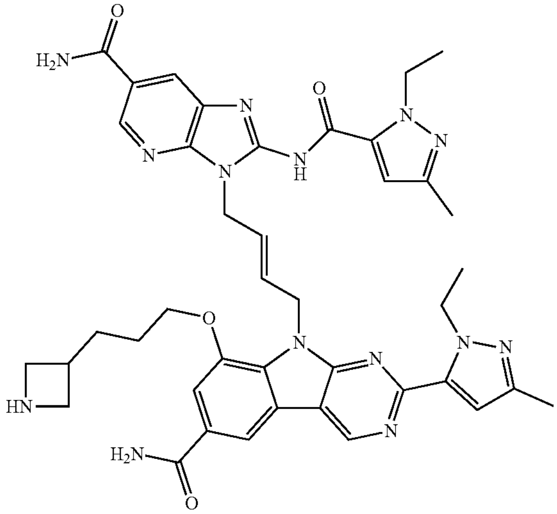 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCC3CNC3)c21]

Example 5-AB (45 mg, 36%) was prepared in a manner similar to that in Example 1-AB from tert-butyl (E)-3-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)azetidine-1-carboxylate. $^1$H NMR (400 MHz, DMSO-d6) δ 9.50 (s, 1H), 8.65 (s, 1H), 8.44 (s, 1H), 8.33 (s, 1H), 8.17 (s, 1H), 8.10 (s, 1H), 8.05 (s, 1H), 7.59 (s, 1H), 7.50 (s, 1H), 7.40 (s, 1H), 6.82 (s, 1H), 6.36 (s, 1H), 5.87 (d, J=13.5 Hz, 1H), 5.69 (d, J=15.9 Hz, 1H), 5.25 (s, 2H), 4.76-4.62 (m, 4H), 4.50-4.40 (m, 2H), 4.05-3.96 (m, 2H), 3.93-3.89 (m, 2H), 3.53-3.45 (m, 2H), 2.68-2.61 (m, 1H), 2.21 (s, 3H), 2.06 (s, 3H), 1.59-1.55 (m, 4H), 1.35-1.29 (m, 3H), 1.21-1.15 (m, 3H). LC-MS (M+H)$^+$=799.7.

Example 6-AA: tert-butyl (E)-4-(2-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)ethyl)piperidin-1-carboxylate

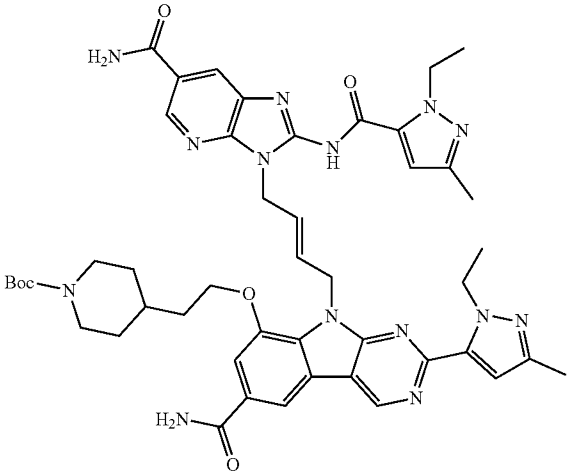 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCC3CCN(C(=O)OC(C)(C)C)CC3)c21]

Step 1: tert-butyl 4-(2-(3-bromo-5-carbamoyl-2-nitrophenoxy)ethyl)piperidine-1-carboxylate

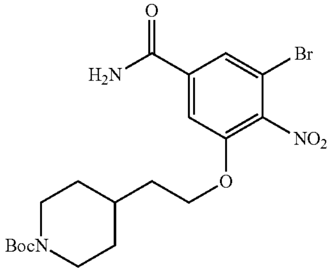 [SMILES: CC(C)(C)OC(=O)N1CCC(CCOc2cc(C(N)=O)cc(Br)c2[N+](=O)[O-])CC1]

The title compound (5.61 g, 63%) was prepared in a manner similar to that in Example 1-AA step 13 from 3-bromo-5-fluoro-4-nitrobenzamide and tert-butyl 4-(2-hydroxyethyl)piperidine-1-carboxylate. LC-MS (M−Boc+H)$^+$=372.0.

Step 2: tert-butyl 4-(2-(5-carbamoyl-3-(2-chloropyrimidin-5-yl)-2-nitrophenoxy)ethyl)piperidine-1-carboxylate

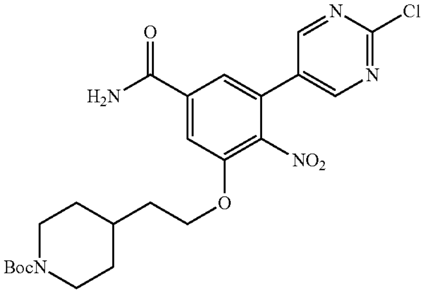 [SMILES: CC(C)(C)OC(=O)N1CCC(CCOc2cc(C(N)=O)cc(-c3cnc(Cl)nc3)c2[N+](=O)[O-])CC1]

The title compound (331 mg, 90%) was prepared in a manner similar to that in Example 1-AA step 14 from tert-butyl 4-(2-(3-bromo-5-carbamoyl-2-nitrophenoxy)ethyl)piperidine-1-carboxylate and 2-chloropyrimidin-5-ylboronic acid. LC-MS (M−Boc+H)$^+$=406.2.

Step 3: tert-butyl 4-(2-(5-carbamoyl-3-(2-(1-ethyl-3-methyl-1H-pyrazol-5-yl)pyrimidin-5-yl)-2-nitrophenoxy)ethyl)piperidin-1-carboxylate

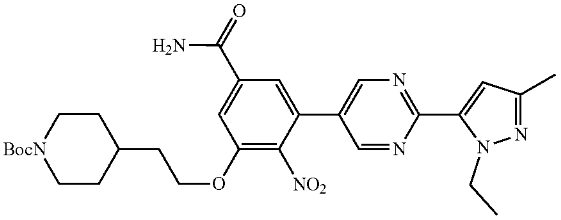 [SMILES: CCn1nc(C)cc1-c1ncc(-c2cc(C(N)=O)cc(OCCC3CCN(C(=O)OC(C)(C)C)CC3)c2[N+](=O)[O-])cn1]

The title compound (196 mg, 52%) was prepared in a manner similar to that in Example 1-AA step 15 from tert-butyl 4-(2-(5-carbamoyl-3-(2-chloropyrimidin-5-yl)-2-nitrophenoxy)ethyl)piperidine-1-carboxylate and 1-ethyl-3-methyl-1H-pyrazol-5-ylboronic acid. LC-MS (M+H)$^+$=580.3.

Step 4: tert-butyl 4-(2-((6-carbamoyl-2-(1-ethyl-3-methyl-1H-pyrazol-5-yl)-9H-pyrimido[4,5-b]indol-8-yl)oxy)ethyl)piperidine-1-carboxylate

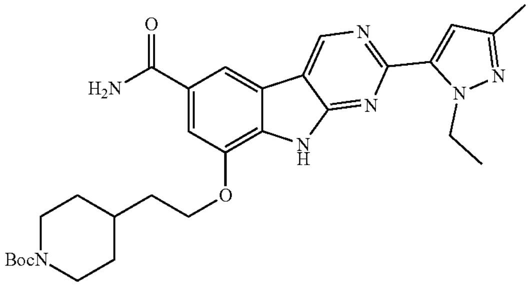 [SMILES: CCn1nc(C)cc1-c1ncc2c(n1)[nH]c1c(OCCC3CCN(C(=O)OC(C)(C)C)CC3)cc(C(N)=O)cc12]

The title compound (110 mg, 6%) was prepared in a manner similar to that in Example 1-AA step 16 from tert-butyl 4-(2-(5-carbamoyl-3-(2-(1-ethyl-3-methyl-1H-pyrazol-5-yl)pyrimidin-5-yl)-2-nitrophenoxy)ethyl)piperidine-1-carboxylate. $^1$H NMR (300 MHz, DMSO-$d_6$) δ 12.67 (s, 1H), 9.50 (s, 1H), 8.40 (s, 1H), 8.02 (s, 1H), 7.63 (s, 1H), 7.34 (s, 1H), 6.79 (s, 1H), 4.85-4.72 (m, 2H), 4.33-4.23 (m, 2H), 4.00-3.89 (m, 2H), 2.75-2.69 (m, 2H), 2.22 (s, 3H), 1.91-1.67 (m, 5H), 1.47-1.31 (m, 12H), 1.18-1.00 (m, 2H). LC-MS $(M+H)^+$=548.3.

Step 5: tert-butyl (E)-4-(2-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)ethyl)piperidine-1-carboxylate

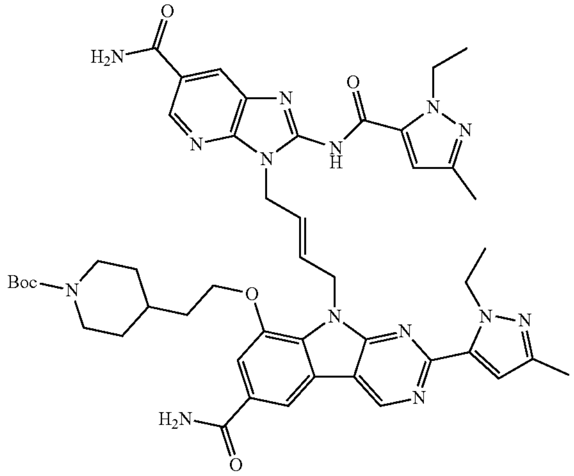 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCC3CCN(C(=O)OC(C)(C)C)CC3)c21]

Example 6-AA (140 mg, 71%) was prepared in a manner similar to that in Example 1-AA step 17 from tert-butyl 4-(2-((6-carbamoyl-2-(1-ethyl-3-methyl-1H-pyrazol-5-yl)-9H-pyrimido[4,5-b]indol-8-yl)oxy)ethyl)piperidine-1-carboxylate and (E)-3-(4-bromobut-2-en-1-yl)-2-(1-ethyl-3-methyl-1H-pyrazole-5-carboxamido)-3H-imidazo[4,5-b]pyridine-6-carboxamide. 1H NMR (400 MHz, DMSO-d6) δ 12.85 (s, I H), 9.48 (s, I H), 8.65 (d, J=1.8 Hz, 1H), 8.41 (d, J=1.2 Hz, 1H), 8.13 (s, 1H), 8.09 (d, J=1.8 Hz, 1H), 8.02 (s, 1H), 7.59 (s, 1H), 7.53 (s, 1H), 7.39 (s, 1H), 6.78 (d, J=0.5 Hz, 1H), 6.40 (s, 1H), 6.00-5.96 (m, 1H), 5.73-5.70 (m, 1H), 5.25 (s, 2H), 4.72 (s, 2H), 4.62 (d, J=7.2 Hz, 2H), 4.45 (d, J=6.9 Hz, 2H), 4.11-4.04 (m, 2H), 3.86 (s, 2H), 2.65 (s, 2H), 2.18 (s, 3H), 2.05 (s, 3H), 1.52 (s, 4H), 1.37 (s, 9H), 1.27-1.17 (m, 9H). LC-MS $(M+H)^+$=913.6.

Example 6-AB: (Ei-9-(4-(6-carbamoyl-2-(1&hl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl-8-(2-(piperidin-4-yl)ethoxy)-9H-pyrimido[4,5-b]indole-6-carboxamide

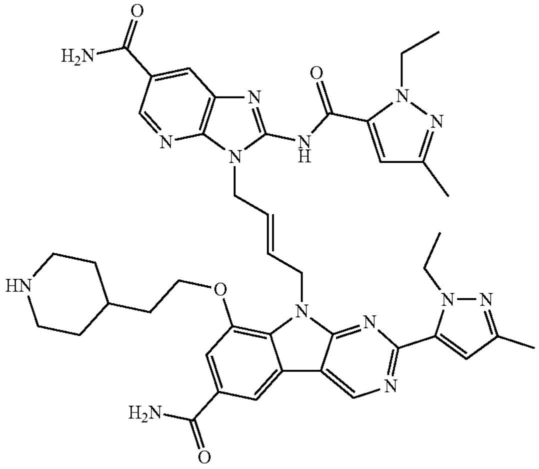 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCC3CCNCC3)c21]

Example 6-AB (90 mg, 79%) was prepared in a manner similar to that in Example 1-AB from tert-butyl (E)-4-(2-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)ethyl)piperidine-1-carboxylate. $^1$H NMR (400 MHz, DMSO-d6) δ 9.49 (s, 1H), 8.61 (s, 1H), 8.42 (s, 1H), 8.09-8.04 (m, 3H), 7.60 (s, 1H), 7.47 (s, 1H), 7.40 (s, 1H), 6.82 (s, 1H), 6.37 (s, 1H), 6.00-5.75 (m, 2H), 5.32-5.22 (m, 2H), 4.78-4.62 (m, 4H), 4.53-4.42 (m, 2H), 4.17-4.07 (m, 2H), 3.11-2.99 (m, 2H), 2.65-2.55 (m, 2H), 2.21 (s, 3H), 2.06 (s, 3H), 1.70-1.50 (m, 4H), 1.37-1.01 (m, 9H). LC-MS $(M+H)^+$=813.5.

Example 7-AA: tert-butyl (E)-4-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)piperidine-1-carboxylate

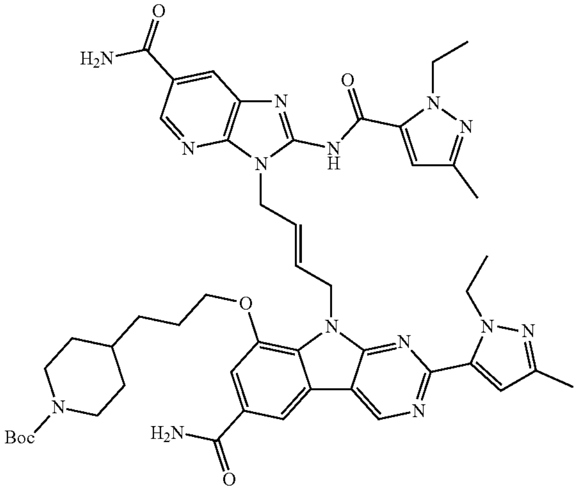 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCC3CCN(C(=O)OC(C)(C)C)CC3)c21]

Step 1: tert-butyl 4-(3-(3-bromo-5-carbamoyl-2-nitrophenoxy)propyl)piperidine-1-carboxylate

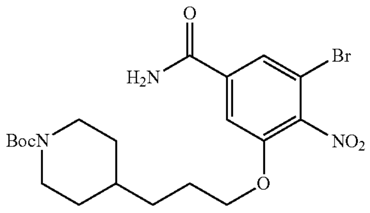 [SMILES: CC(C)(C)OC(=O)N1CCC(CCCOc2cc(C(N)=O)cc(Br)c2[N+](=O)[O-])CC1]

The title compound (7.56 g, 83%) was prepared in a manner similar to that in Example 1-AA step 13 from 3-bromo-5-fluoro-4-nitrobenzamide and tert-butyl 4-(3-hydroxypropyl)piperidine-1-carboxylate. LC-MS (M−Boc+H)$^+$=385.9.

Step 2: tert-butyl 4-(3-(5-carbamoyl-3-(2-chloropyrimidin-5-yl)-2-nitrophenoxy)propyl)piperidine-1-carboxylate

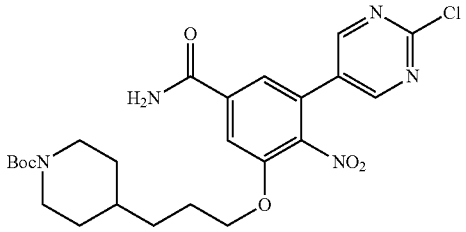 [SMILES: CC(C)(C)OC(=O)N1CCC(CCCOc2cc(C(N)=O)cc(-c3cnc(Cl)nc3)c2[N+](=O)[O-])CC1]

The title compound (358 mg, 37%) was prepared in a manner similar to that in Example 1-AA step 14 from tert-butyl 4-(3-(3-bromo-5-carbamoyl-2-nitrophenoxy)propyl)piperidine-1-carboxylate and 2-chloropyrimidin-5-yl boronic acid. LC-MS (M−Boc+H)$^+$=420.1.

Step 3: tert-butyl 4-(3-(5-carbamoyl-3-(2-(1-ethyl-3-methyl-1H-pyrazol-5-yl)pyrimidin-5-yl)-2-nitrophenoxy)propyl)piperidine-11-carboxylate

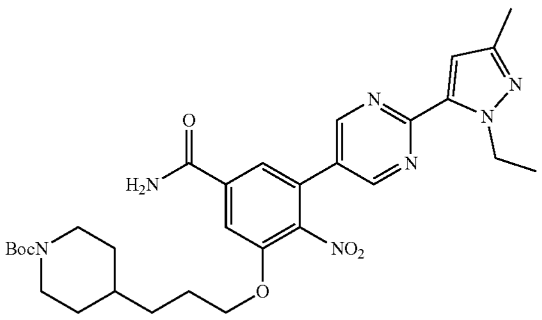 [SMILES: CCn1nc(C)cc1-c1ncc(-c2cc(C(N)=O)cc(OCCCC3CCN(C(=O)OC(C)(C)C)CC3)c2[N+](=O)[O-])cn1]

The title compound (195 mg, 48%) was prepared in a manner similar to that in Example 1-AA step 15 from tert-butyl 4-(3-(5-carbamoyl-3-(2-chloropyrimidin-5-yl)-2-nitrophenoxy)propyl)piperidine-1-carboxylate and 1-ethyl-3-methyl-1H-pyrazol-5-ylboronic acid. LC-MS (M+H)$^+$=594.4.

Step 4: tert-butyl 4-(3-((6-carbamoyl-2-(1-ethyl-3-methyl-1H-pyrazol-5-yl-9H-pyrimido[4,5-b]indol-8-yl)oxy)propyl)piperidine-1-carboxylate

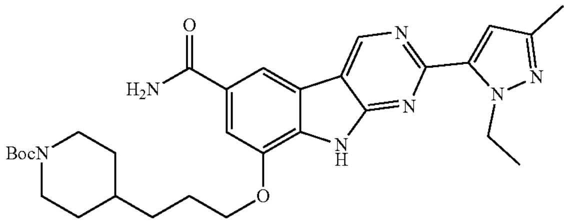 [SMILES: CCn1nc(C)cc1-c1ncc2c(n1)[nH]c1c(OCCCC3CCN(C(=O)OC(C)(C)C)CC3)cc(C(N)=O)cc12]

The title compound (97 mg, 5%) was prepared in a manner similar to that in Example 1-AA step 17 from tert-butyl 4-(3-(5-carbamoyl-3-(2-(1-ethyl-3-methyl-1H-pyrazol-5-yl)pyrimidin-5-yl)-2-nitrophenoxy)propyl)piperidine-1-carboxylate. $^1$H NMR (300 MHz, DMSO-d$_6$) δ 12.68 (s, 1H), 9.52 (s, 1H), 8.42 (s, 1H), 8.04 (s, 1H), 7.63 (s, 1H), 7.35 (s, 1H), 6.81 (s, 1H), 4.87-4.74 (m, 2H), 4.30-4.20 (m, 2H), 4.00-3.90 (m, 2H), 2.83-2.63 (m, 2H), 2.24 (s, 3H), 1.91-1.83 (m, 2H), 1.77-1.65 (m, 2H), 1.57-1.47 (m, 3H), 1.45-1.34 (m, 12H), 1.09-0.99 (m, 2H). LC-MS (M+H)$^+$=562.3.

Step 5: tert-butyl (E)-4-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl-9H-pyrimido[4,5-b]indol-8-yl)oxy)propylpiperidine-1-carboxylate

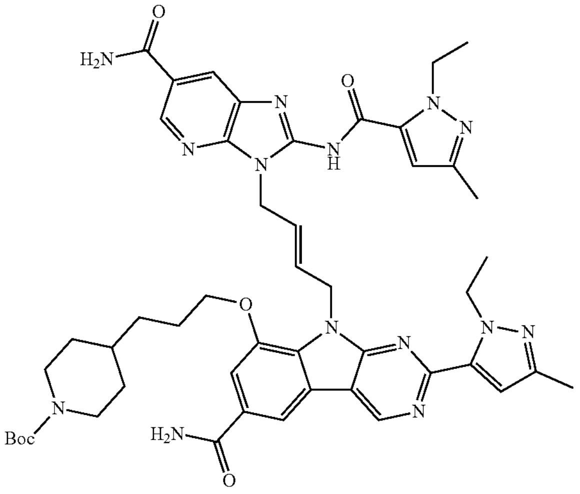 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCC3CCN(C(=O)OC(C)(C)C)CC3)c21]

Example 7-AA (110 mg, 59%) was prepared in a manner similar to that in Example 1-AA step 17 from tert-butyl 4-(3-((6-carbamoyl-2-(1-ethyl-3-methyl-1H-pyrazol-5-yl)-9H-pyrimido[4,5-b]indol-8-yl)oxy)propyl)piperidine-1-carboxylate and (E)-3-(4-bromobut-2-en-1-yl)-2-(1-ethyl-3-methyl-1H-pyrazole-5-carboxamido)-3H-imidazo[4,5-b]pyridine-6-carboxamide. $^1$H NMR (400 MHz, DMSO-d6) δ12.86 (s, 1H), 9.47 (s, 1H), 8.66 (s, 1H), 8.40 (s, 1H), 8.14 (s, 1H), 8.10 (s, 1H), 8.02 (s, 1H), 7.55 (s, 2H), 7.38 (s, 1H), 6.79 (s, 1H), 6.39 (s, 1H), 5.94 (s, 1H), 5.72 (s, 1H), 5.24 (s, 2H), 4.70 (s, 2H), 4.65 (s, 2H), 4.45 (s, 2H), 3.98 (s, 2H), 3.83 (s, 2H), 2.53 (S, 2H), 2.18 (s, 3H), 2.04 (s, 3H), 1.60-1.44 (m, 4H), 1.36 (S, 9H), 1.30-1.21 (dd, J=30.9, 4.6 Hz, 8H), 0.86 (s, 3H). LC-MS $(M+H)^+$=927.7.

Example 7-AB: (E)-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl-8-(3-(piperidin-4-yl)propoxy)-9H-pyrimido[4,5-b]indole-6-carboxamide

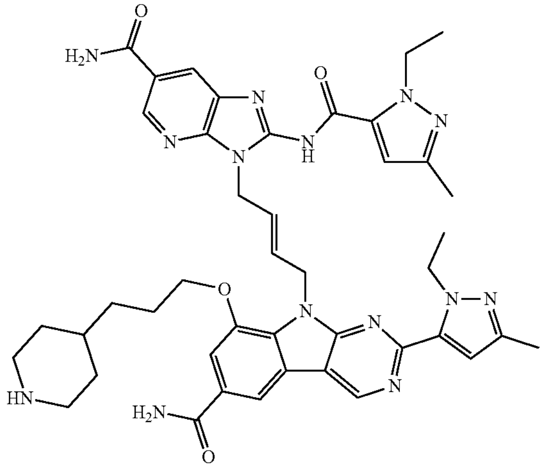 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCC3CCNCC3)c21]

Example 7-AB (45 mg, 49%) was prepared in a manner similar to that in Example 1-AB from tert-butyl (E)-4-(3-((6-carbamoyl-9-(4-(6-carbamoyl-2-(1-ethyl-3-methyl-1H-pyrazole-5-carboxamido)-3H-imidazo[4,5-b]pyridin-3-yl)but-2-en-1-yl)-2-(1-ethyl-3-methyl-1H-pyrazol-5-yl)-9H-pyrimido[4,5-b]indol-8-yl)oxy)propyl)piperidine-1-carboxylate. $^1$H NMR (400 MHz, DMSO-d6) δ 9.50 (s, 1H), 8.66 (s, 1H), 8.43 (s, 1H), 8.33 (s, 1H), 8.17 (s, 1H), 8.11 (s, 1H), 8.05 (s, 1H), 7.58 (s, 1H), 7.51 (s, 1H), 7.39 (s, 1H), 6.83 (s, 1H), 6.39 (s, 1H), 5.93 (d, J=15.3 Hz, 1H), 5.77 (d, J=15.5 Hz, 1H), 5.29-5.22 (m, 2H), 4.75-4.65 (m, 4H), 4.50-4.42 (m 2H), 4.06-4.00 (m, 2H), 3.20-3.12 (m, 2H), 2.75-2.64 (m, 2H), 2.22 (s, 3H), 2.07 (s, 3H), 1.62-1.59 (m, 4H), 1.47-1.01 (m, 11H). LC-MS $(M+H)^+$=827.7.

Biological Activity

STING Cellular Assay in THP1-Dual™ Cells

Materials

THP1-Dual™ cells were derived from the human THP-1 monocyte cell line by stable integration of two inducible reporter constructs. THP1-Dual™ cells feature the Lucia luciferase gene, a new secreted luciferase reporter gene, under the control of an ISG54 (interferon-stimulated gene) minimal promoter in conjunction with five interferon (IFN)-stimulated response elements. THP1-Dual™ cells also express a secreted embryonic alkaline phosphatase (SEAP) reporter gene driven by an IFN-β minimal promoter fused to five copies of the NF-κB consensus transcriptional response element and three copies of the c-Rel binding site. As a result, THP1-Dual™ cells allow the simultaneous study of the NF-κB pathway, by monitoring the activity of SEAP, and the interferon regulatory factor (IRF) pathway, by assessing the activity of Lucia luciferase. Both reporter proteins are readily measurable in the cell culture supernatant when using QUANTI-Blue™, a SEAP detection reagent, and QUANTI-Luc™, a Lucia luciferase detection reagent.

Distinct variants of human STING (hSTING) that affect CDN recognition and signal transduction have been identified:

R232 (R71-G230-R232-R293): the most prevalent in the human population (~60%). Referred as the "wild-type" or 232R-RGR allele2.

HAQ (H71-A230-R232-Q293): contains three non-synonymous single nucleotide substitutions; R71H, G230A and R293Q. This allele, found in ~20% of the population, is less sensitive to CDNs than the "wild-type" allele2.

Cell Maintenance

Growth Medium: RPMI 1640.2 mM L-glutamine, 25 mM HEPES, 10% heat-inactivated fetal bovine serum (30 min at 56° C.), 100 μg/mL Normocin™, Pen-Strep (100 U/mL-100 μg/mL)

1. After cells have recovered (after at least one passage), maintain and subculture the cells in growth medium. (To maintain selection pressure, add 10 μg/mL of blasticidin and 100 μg/mL of Zeocin™ to the growth medium every other passage.)
2. Pass the cells every 3 days by inoculating $7\times10^5$ cells/ml. Do not allow the cell concentration to exceed $2\times10^6$ cells/mL.

Experimental Procedure

1. Add 180 μL of cell suspension (~100,000 cells) per well of a flat-bottom 96-well plate (costar 3599).
2. Then compounds were added with serial dilutions over 10 points with a 1 nM-10 μM final concentration range in 0.1% DMSO/growth medium.
3. Incubate the plate for 24 h at 37° C., 5% $CO_2$.
4. Set the BMG PHERAstar FSX instrument with the following parameters: 50 μL of injection, end-point measurement with a 4 second start time and 0.1 second reading time.
5. Pipet 10 dL of THP1-Dual™ cell culture medium per well into a 96-well white opaque plate (Coring 3903).
6. Add 50 μL of QUANTI-Luc assay solution to each well and gently tap the plate several times to mix. Proceed immediately with the measurement.

TABLE 1

Cellular activity $EC_{50}$ (nM) for the compounds disclosed herein

| Compound No. | Cellular activity $EC_{50}$ in THP1-Dual HAQ Cells (nM) | Cellular activity $EC_{50}$ in THP1-Dual KI-hSTING-R232 Cells (nM) |
|---|---|---|
| Example 1-AA | 3.4 | 0.58 |
| Example 1-AB | 355 | 6.2 |
| Example 2-AA | 2.4 | 0.46 |
| Example 2-AB-HCl | 565 | 11 |
| Example 1-AC | 34 | 3.6 |
| Example 2-AC | 118 | 10 |
| Example 3-AA | 4.1 | 0.52 |
| Example 3-AB-HCl | 640 | 23 |
| Example 4-AA | 4.8 | 0.78 |
| Example 4-AB | 1044 | 30 |
| Example 5-AA | 39 | 1.6 |
| Example 5-AB | 862 | 27 |
| Example-6-AA | 49 | 0.90 |
| Example 6-AB | 674 | 29 |
| Example 7-AA | 28 | 1.0 |

TABLE 1-continued

Cellular activity $EC_{50}$ (nM) for the compounds disclosed herein

| Compound No. | Cellular activity $EC_{50}$ in THP1-Dual HAQ Cells (nM) | Cellular activity $EC_{50}$ in THP1-Dual KI-hSTING-R232 Cells (nM) |
|---|---|---|
| Example 7-AB | 305 | 16 |

It is to be understood that, if any prior art publication is referred to herein; such reference does not constitute an admission that the publication forms a part of the common general knowledge in the art in any country.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A compound of formula (I), (I)

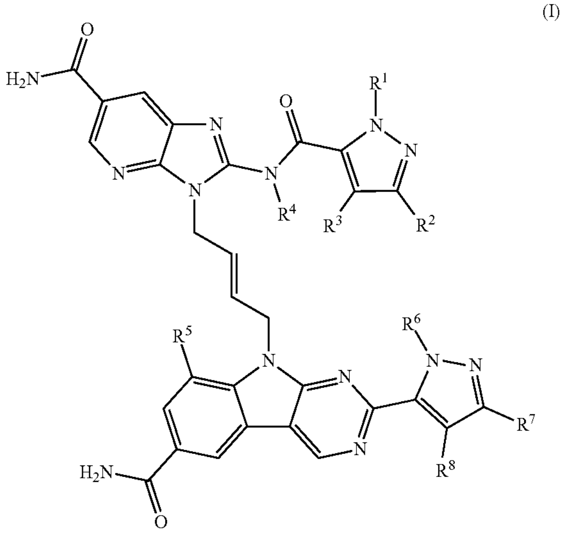

or a pharmaceutically acceptable salt or tautomer thereof, wherein:

$R^1$, $R^2$, $R^3$, $R^4$, $R^6$, $R^7$ and $R^8$, which may be the same or different, each are independently selected from hydrogen, halogen, —$C_{1-8}$alkyl, —$C_{2-8}$alkenyl, —$C_{2-8}$alkynyl, cycloalkyl, heterocyclyl, aryl, heteroaryl, —CN, —$NO_2$, —$OR^a$, —$SO_2R^a$, —C(═O)$R^a$, —C(═O)$OR^a$, —C(═O)$NR^aR^b$, —C(═$NR^a$)$NR^bR^c$, —$NR^aR^b$, —$NR^a$C(═O)$R^b$, —$NR^a$C(═O)$NR^bR^c$, —$NR^a$C(═O)$OR^b$, —$NR^a$SO$NR^bR^c$, —$NR^aSO_2NR^bR^c$, —$SO_2NR^aR^b$, or —$NR^aSO_2R^b$, each of said —$C_{1-8}$alkyl, —$C_{2-8}$alkenyl, —$C_{2-8}$alkynyl, cycloalkyl, heterocyclyl, aryl, or heteroaryl is optionally substituted with $R^d$;

$R^5$ is selected from —$R^{5a}$, —$OR^{5b}$, —$SR^{5a}$ or —$NR^{5a}R^{5b}$;

$R^{5a}$ and $R^{5b}$ are independently selected from hydrogen, —$C_{1-8}$alkyl, —C(═O)R, —$(CH_2)_{n1}$—NRR', $CH_2CH_2O)_{n1}$—NRR', —$(OH_2CH_2)_{n1}$—NRR', —$(CH_2OCH_2)_{n1}$—NRR' or

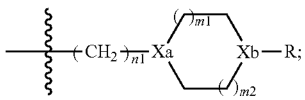

R and R' are each independently selected from hydrogen, —$C_{1-8}$alkyl, —C(═O)$OR^9$; —C(═O)—$CH_2$—$OR^9$, or —$(CH_2)_2$—$OR^9$;

$R^9$ is selected from hydrogen, —$C_{1-8}$alkyl (such as tert-butyl), or —$NR^{9a}R^{9b}$;

$R^9$ and $R^{9b}$ are each independently selected from hydrogen, —$C_{1-8}$alkyl, —$C_{2-8}$alkenyl, —$C_{2-8}$alkynyl, cycloalkyl, heterocyclyl, aryl, and heteroaryl;

Xa and Xb are independently selected from N and CH;

n1 is 1, 2, 3, 4, 5, or 6;

m1 and m2 are each independently 0, 1, or 2;

$R^a$, $R^b$ and $R^c$ are each independently selected from the group consisting of hydrogen, —$C_{1-8}$alkyl, —C(═O)$OR^e$ or —C(═O)$R^e$, wherein the —$C_{1-8}$alkyl is optionally substituted with $NR^*R^b$, —$C_{3-8}$cycloalkyl or a 4-7 membered heterocycle comprising at least one heteroatom selected from N, O and S with the remaining ring atoms being carbon; and $R^d$ and $R^e$ are each independently selected from halogen, —$C_{1-8}$alkyl, —OH, —$NH_2$, —CN, —$C_{1-8}$alkoxy, and —$C_{3-8}$cycloalkyl, wherein each of the —$C_{1-8}$alkyl, —$C_{1-8}$alkoxy and —$C_{3-8}$cycloalkyl is optionally substituted with halogen, —OH, —$NH_2$, —CN, or an oxo group.

2. The compound according to claim 1, $R^5$ is selected from

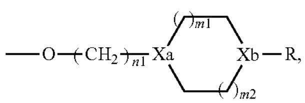

—O—$(CH_2)_{n1}$—NRR', —$(OCH_2CH_2)_{n1}$—NRR' or —O—$(CH_2OCH_2)_{n1}$—NRR'.

3. The compound according to claim 2, wherein $R^1$, $R^2$, $R^3$, $R^6$, $R^7$ and $R^8$ are each independently selected from the group consisting of hydrogen or —$C_{1-8}$alkyl.

4. The compound according to claim 1, wherein $R^4$ is hydrogen.

5. The compound according to claim 1, wherein $R^3$ and $R^8$ are hydrogen.

6. The compound according to claim 1, wherein $R^1$, $R^2$, $R^6$ and $R^7$ are each independently selected from methyl or ethyl.

7. The compound according to claim 1, wherein $R^1$ and $R^6$ are each ethyl; and/or $R^2$ and $R^7$ are each methyl.

8. The compound according to claim 1, wherein $R^5$ is selected from

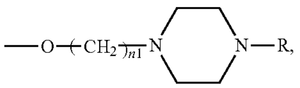

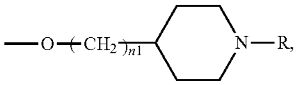

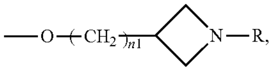

—O—$(CH_2)_{n1}$—NHR, or —$(OCH_2CH_2)_{n1}$—NHR; n1 is 2, 3 or 4; R is selected from hydrogen, $CH_3$, —C(═O)$OR^9$, or —C(═O)—$CH_2$—$OR^9$; $R^9$ is selected from hydrogen, $NH_2$, or —$C(CH_3)_3$.

9. The compound of according to claim 8, wherein R is selected from hydrogen, —$CH_3$,

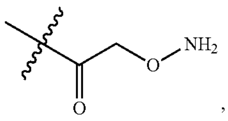
,
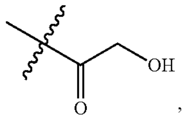
, or —C(═O)$OC(CH_3)_3$.

10. The compound according to claim 1, wherein formula (I) is (II)

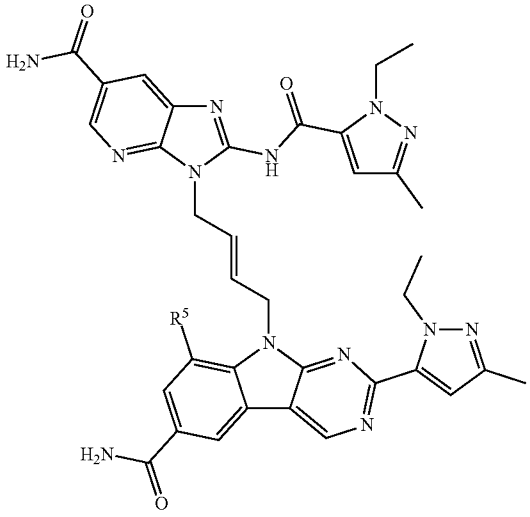
, or a pharmaceutically acceptable salt or tautomer thereof.

11. The compound according to claim 10, wherein the formula (II) is

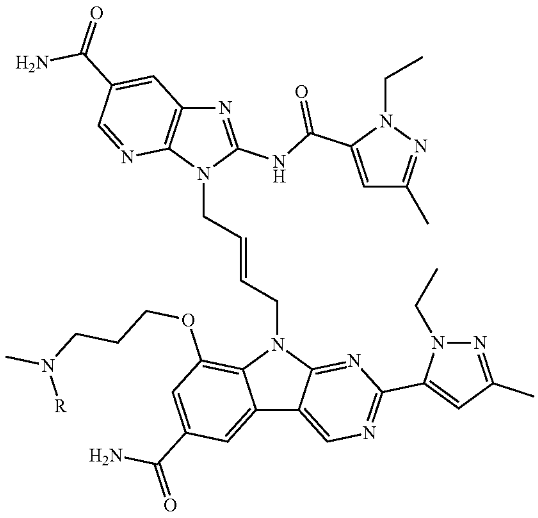
,

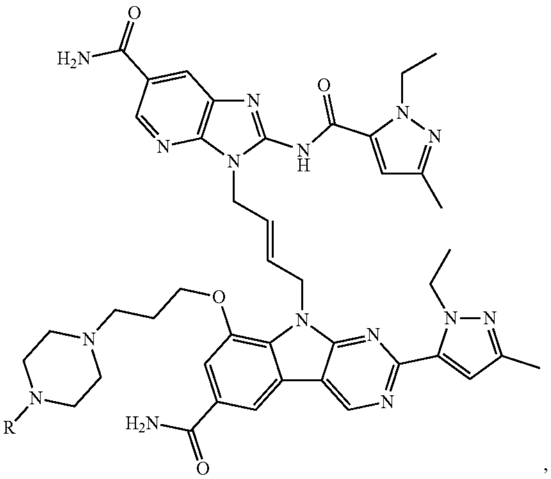
,

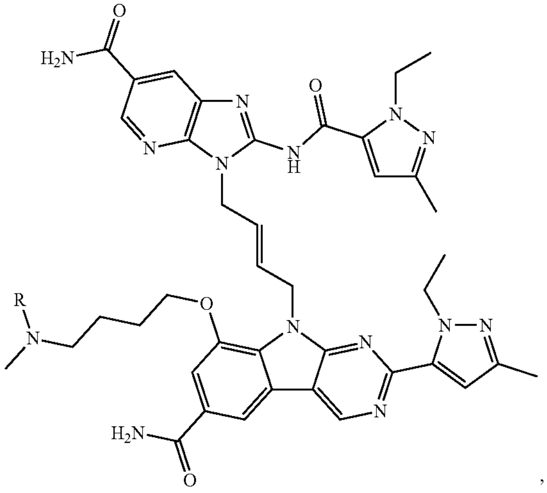
,

-continued
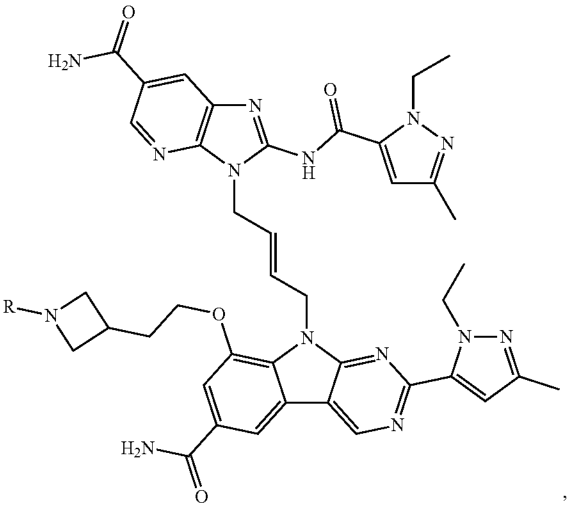
,
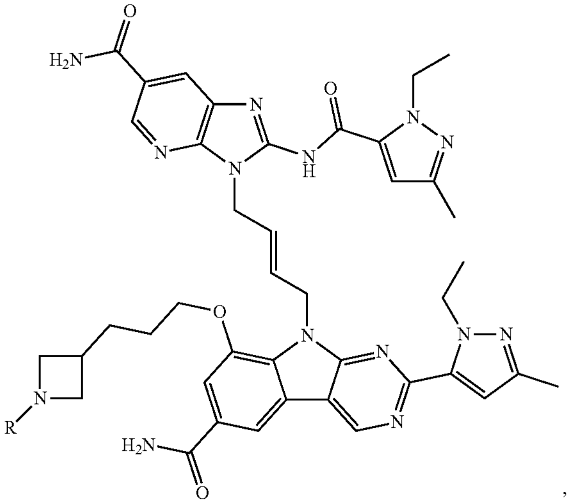
,
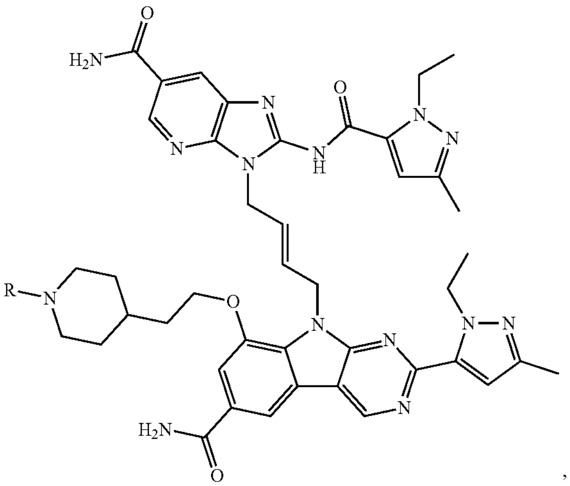
,
-continued
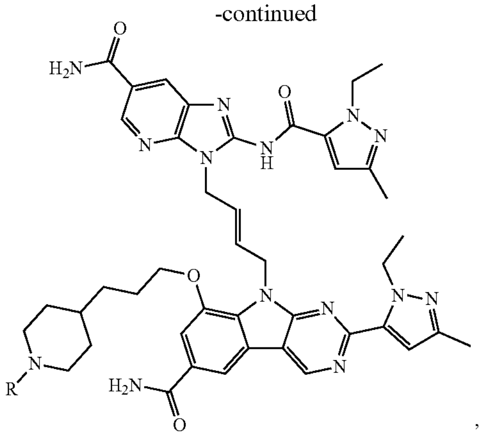
, or
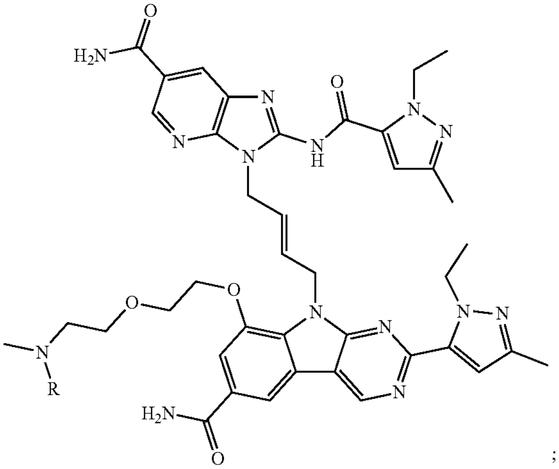
;
or a pharmaceutically acceptable salt or tautomer thereof, wherein R is selected from $CH_3$,
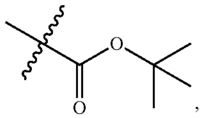
,
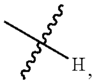
,
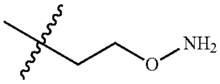
,
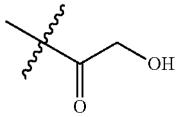
or
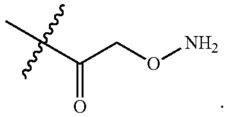
.
12. The compound according to claim 1, wherein the compound is

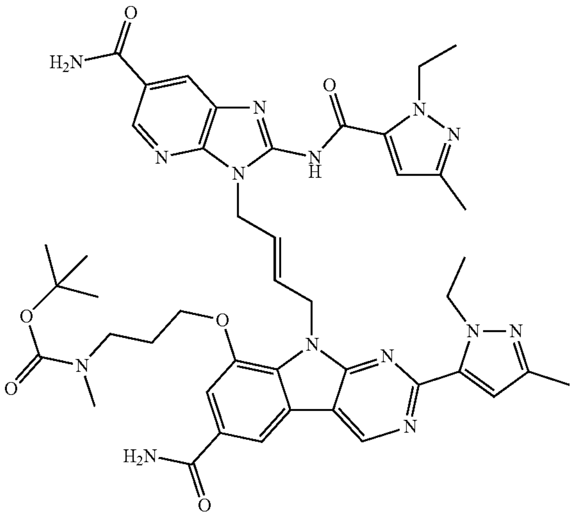 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN(C)C(=O)OC(C)(C)C)c21]
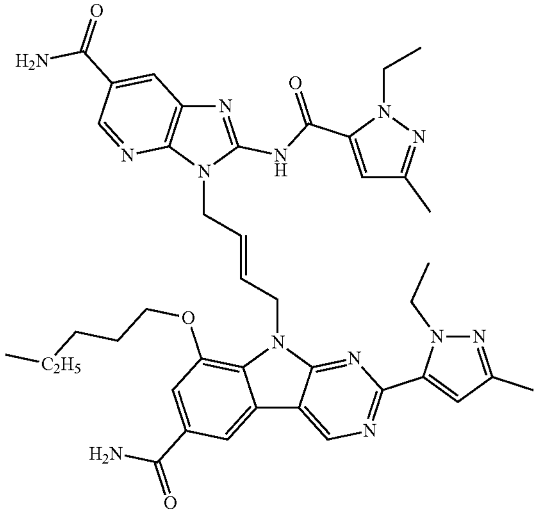
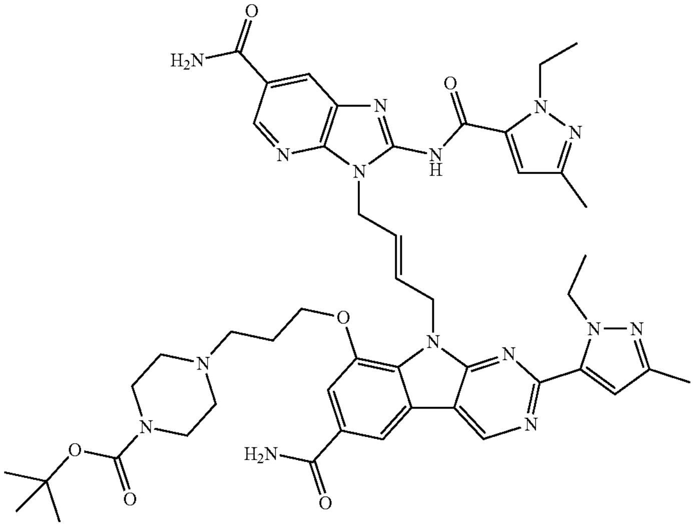 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN3CCN(C(=O)OC(C)(C)C)CC3)c21]

-continued
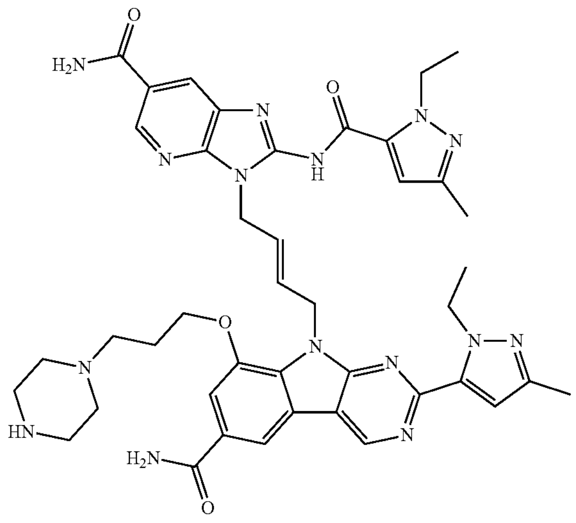
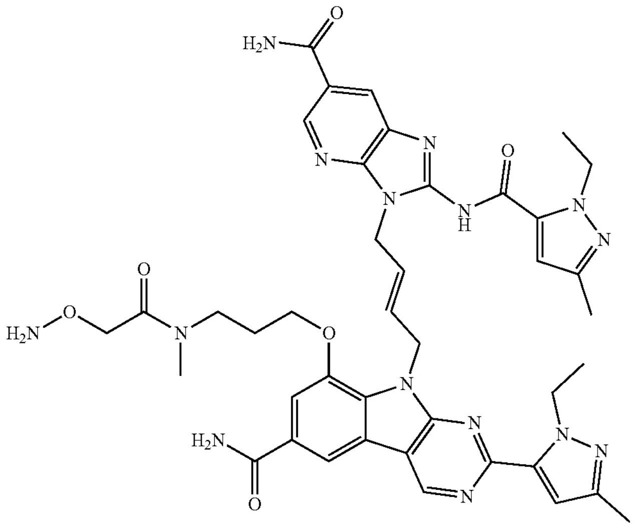 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN(C)C(=O)CON)c21]
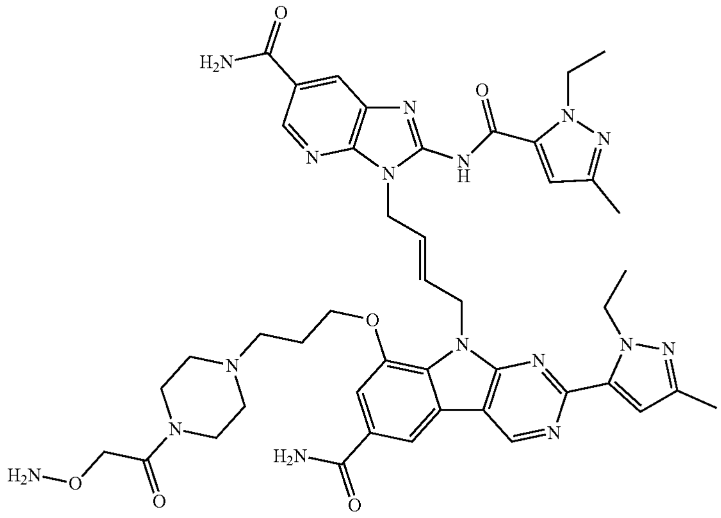 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN3CCN(C(=O)CON)CC3)c21]

-continued
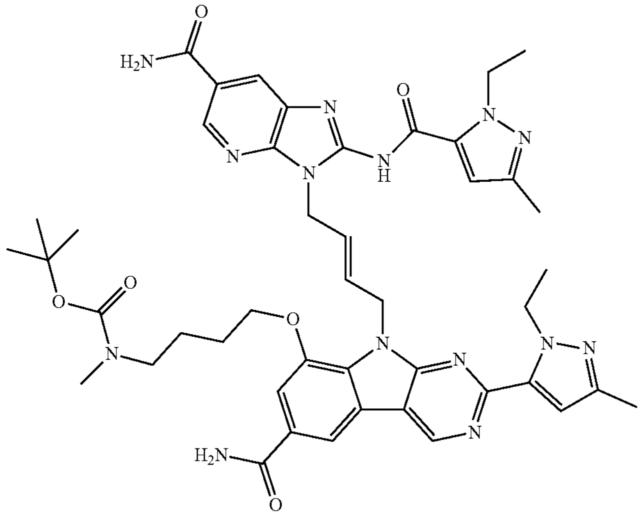 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCCN(C)C(=O)OC(C)(C)C)c21]
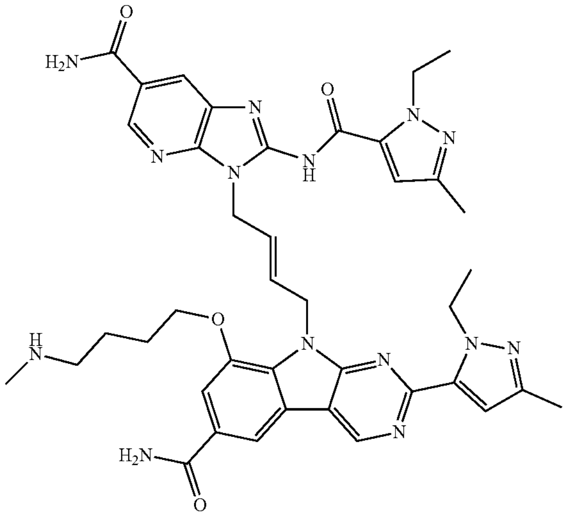
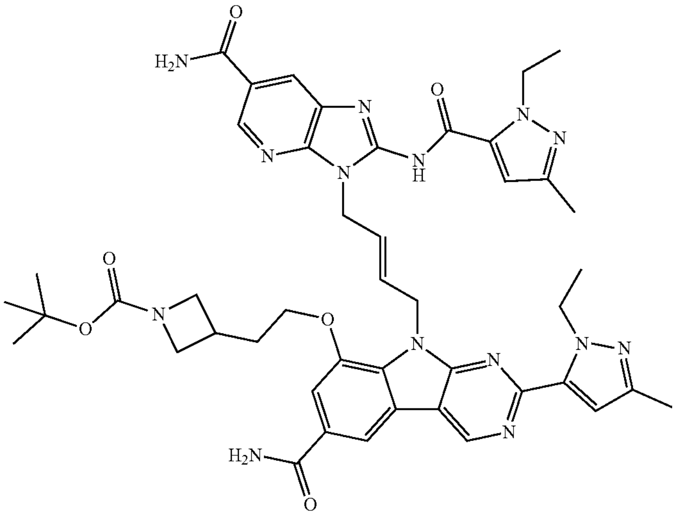 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCC3CN(C(=O)OC(C)(C)C)C3)c21]

-continued
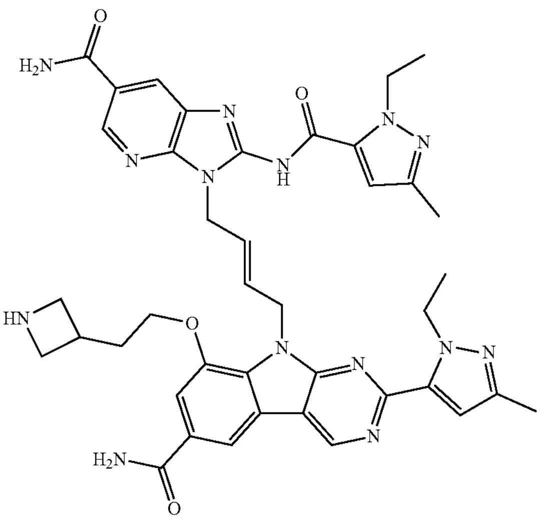 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCC3CNC3)c21]
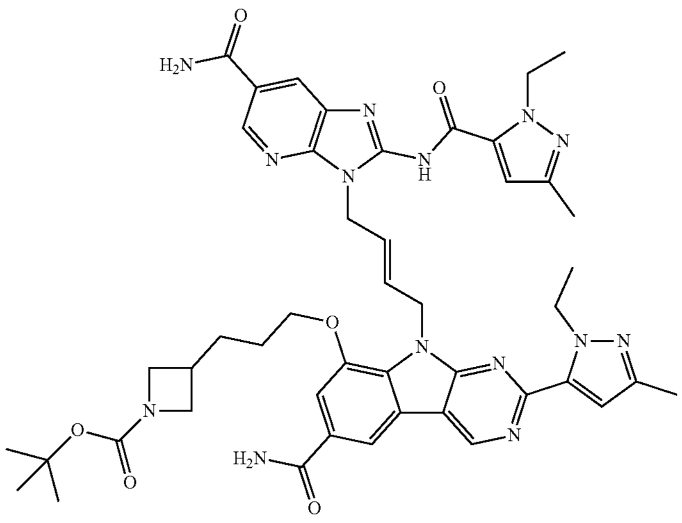 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCC3CN(C(=O)OC(C)(C)C)C3)c21]
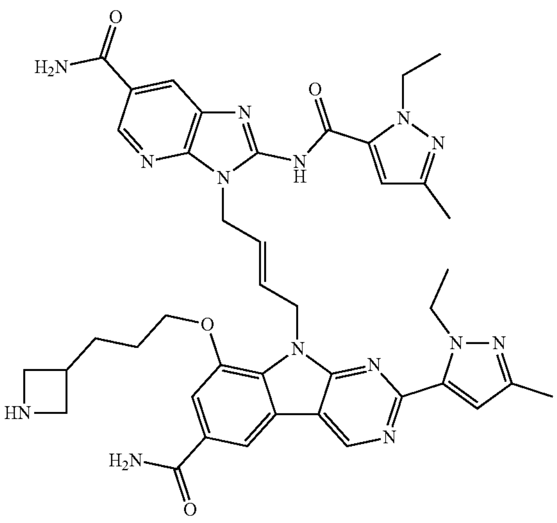 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCC3CNC3)c21]

-continued
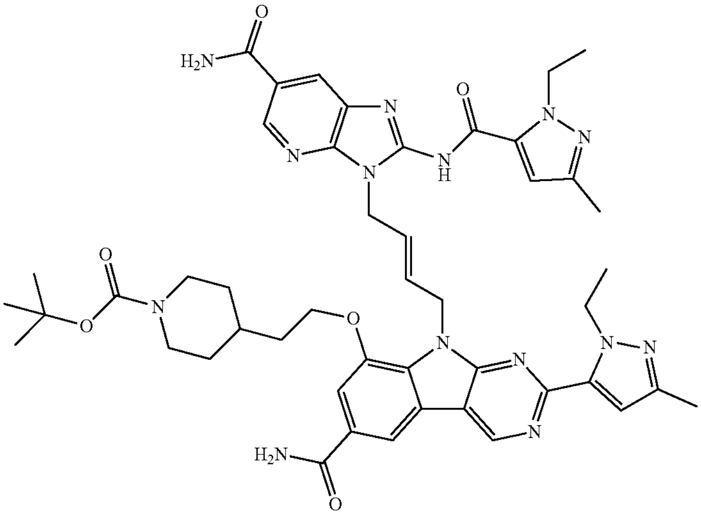 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCC3CCN(C(=O)OC(C)(C)C)CC3)c21]
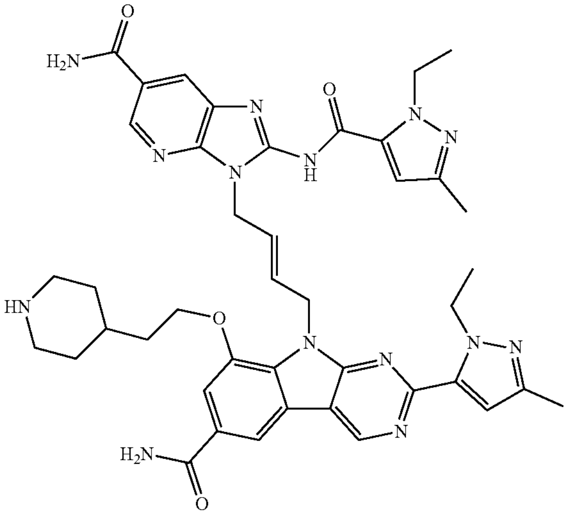 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCC3CCNCC3)c21]
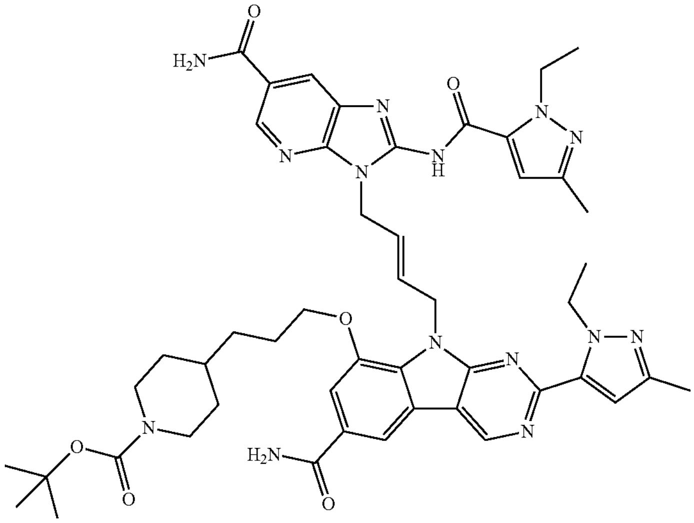 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCC3CCN(C(=O)OC(C)(C)C)CC3)c21]

-continued
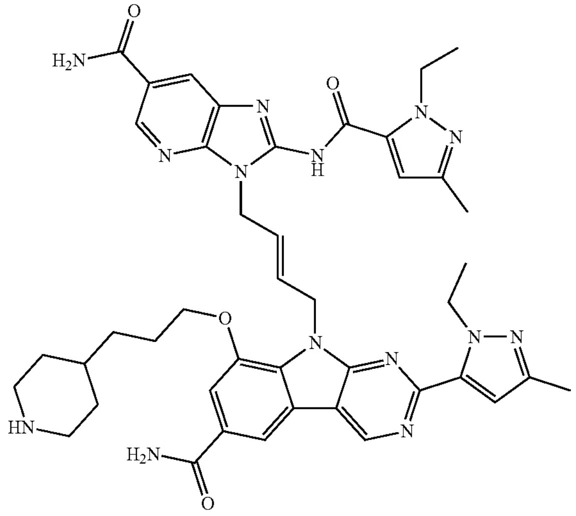 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCC3CCNCC3)c21]
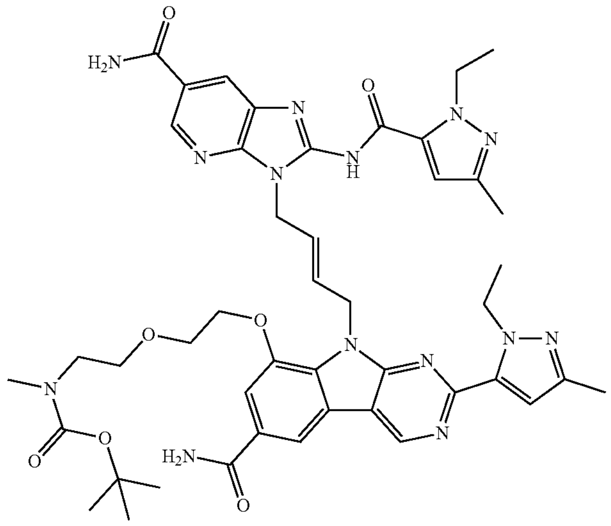
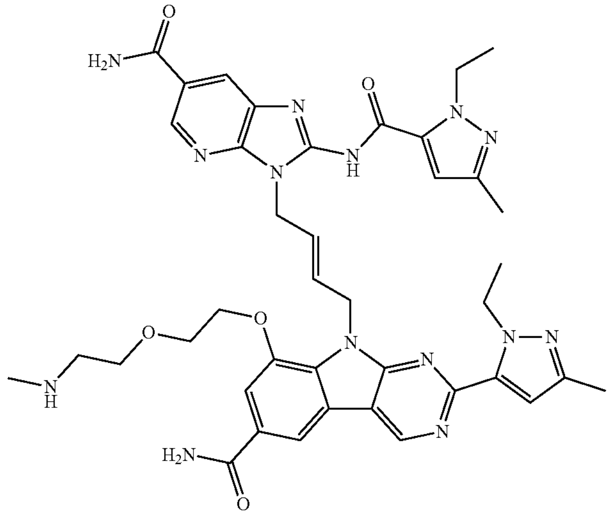

-continued
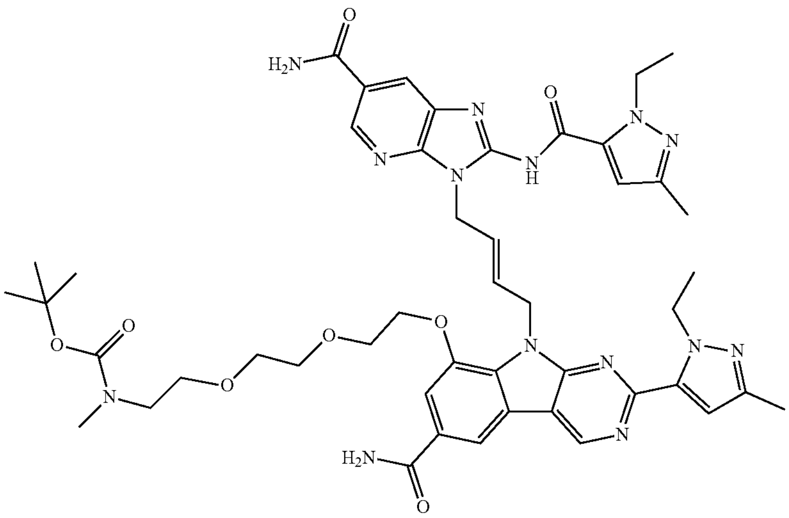 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCOCCOCCN(C)C(=O)OC(C)(C)C)c21]
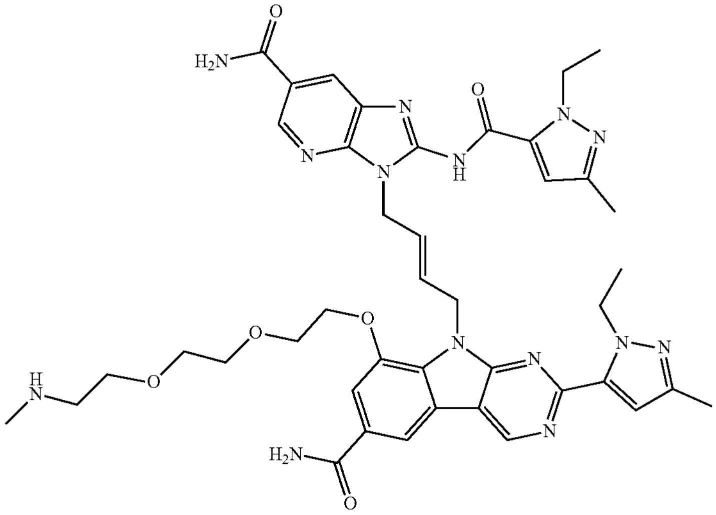
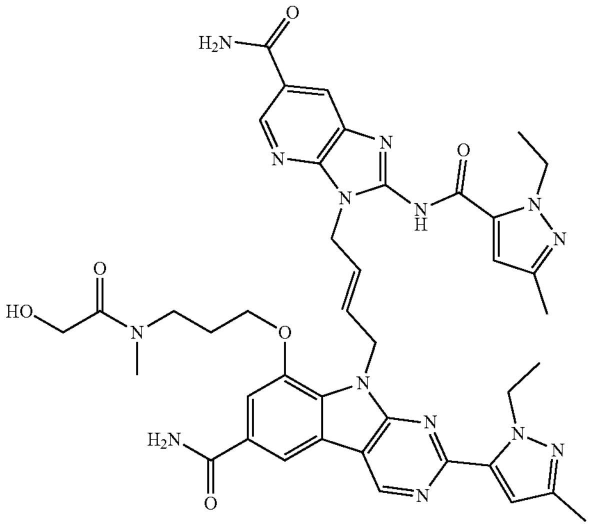 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN(C)C(=O)CO)c21]

-continued

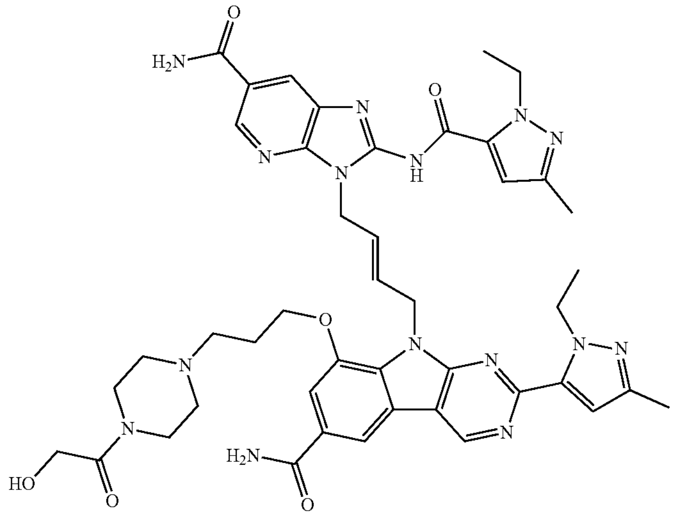 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN3CCN(C(=O)CO)CC3)c21]

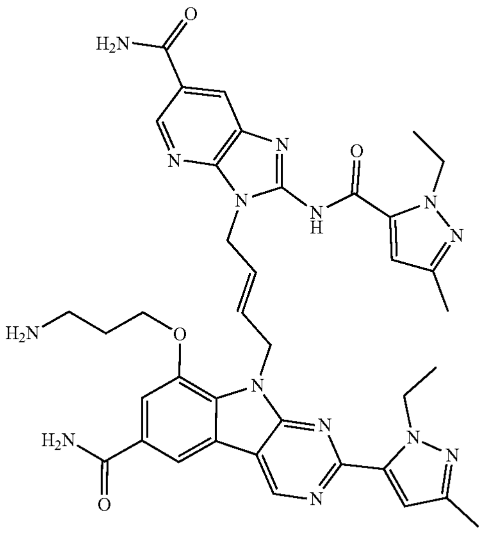 [SMILES: CCn1nc(C)cc1C(=O)Nc1nc2cc(C(N)=O)cnc2n1C/C=C/Cn1c2nc(-c3cc(C)nn3CC)ncc2c2cc(C(N)=O)cc(OCCCN)c21]

or a pharmaceutically acceptable salt or tautomer thereof.

13. A pharmaceutical composition comprising a compound of claim 1 or a pharmaceutically acceptable salt or tautomer thereof, together with a pharmaceutically acceptable excipient.

14. A method of treating a disease affected by STING modulation, comprising administering to a subject in need thereof an effective amount of a compound of claim 1 or a pharmaceutically acceptable salt or tautomer thereof.

15. The method of claim 14, wherein the disease is selected from inflammation, allergic and autoimmune diseases, infectious diseases, cancer, or pre-cancerous syndromes.

* * * * *